United States Patent
Gu

(10) Patent No.: US 10,449,184 B2
(45) Date of Patent: *Oct. 22, 2019

(54) PHARMACEUTICAL COMPOSITIONS OF THERAPEUTICALLY ACTIVE COMPOUNDS

(71) Applicant: Agios Pharmaceuticals, Inc., Cambridge, MA (US)

(72) Inventor: Chong-Hui Gu, Waban, MA (US)

(73) Assignee: Agios Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/949,750

(22) Filed: Apr. 10, 2018

(65) Prior Publication Data

US 2018/0325880 A1 Nov. 15, 2018

Related U.S. Application Data

(63) Continuation of application No. 15/125,880, filed as application No. PCT/US2015/020349 on Mar. 13, 2015, now Pat. No. 9,968,595.

(60) Provisional application No. 62/081,542, filed on Nov. 18, 2014, provisional application No. 61/953,487, filed on Mar. 14, 2014.

(51) Int. Cl.
| A61K 31/444 | (2006.01) |
| A61K 47/38 | (2006.01) |
| A61K 9/10 | (2006.01) |
| A61K 9/20 | (2006.01) |
| A61K 9/14 | (2006.01) |
| C07D 401/14 | (2006.01) |

(52) U.S. Cl.
CPC .............. *A61K 31/444* (2013.01); *A61K 9/10* (2013.01); *A61K 9/146* (2013.01); *A61K 9/2054* (2013.01); *A61K 47/38* (2013.01); *C07D 401/14* (2013.01)

(58) Field of Classification Search
CPC ........ A61K 31/444; A61K 47/38; A61K 9/10; A61K 9/146; A61K 9/2054; C07D 401/14
See application file for complete search history.

(56) References Cited

U.S. PATENT DOCUMENTS

| 2,390,529 A | 12/1945 | Friedheim |
| 3,755,322 A | 8/1973 | Winter et al. |
| 3,867,383 A | 2/1975 | Winter |
| 4,084,053 A | 4/1978 | Desai et al. |
| 5,021,421 A | 6/1991 | Hino et al. |

(Continued)

FOREIGN PATENT DOCUMENTS

| CN | 101296909 A | 10/2008 |
| CN | 101575408 A | 11/2009 |

(Continued)

OTHER PUBLICATIONS

"Study of orally administered AG-120 in subjects with advanced hematologic malignancies with an IDH1 mutation," clinicaltrials.gov retreived Feb. 6, 2017.

(Continued)

*Primary Examiner* — Savitha M Rao
(74) *Attorney, Agent, or Firm* — Goodwin Procter LLP

(57) ABSTRACT

Provided are compounds and pharmaceutical compositions useful for treating cancer and methods of treating cancer comprising administering to a subject in need thereof a compound or pharmaceutical composition described herein.

23 Claims, 13 Drawing Sheets

(56) References Cited

U.S. PATENT DOCUMENTS

| | | |
|---|---|---|
| 5,489,591 A | 2/1996 | Kobayashi et al. |
| 5,807,876 A | 9/1998 | Armistead et al. |
| 5,834,485 A | 11/1998 | Dyke et al. |
| 5,965,559 A | 10/1999 | Faull et al. |
| 5,965,569 A | 10/1999 | Camps Garcia et al. |
| 5,984,882 A | 11/1999 | Rosenschein et al. |
| 6,262,113 B1 | 7/2001 | Widdowson et al. |
| 6,274,620 B1 | 8/2001 | Labrecque et al. |
| 6,313,127 B1 | 11/2001 | Waterson et al. |
| 6,399,358 B1 | 6/2002 | Williams et al. |
| 6,576,235 B1 | 6/2003 | Williams et al. |
| 6,723,730 B2 | 4/2004 | Bakthavatchalam et al. |
| 6,783,965 B1 | 8/2004 | Sherman et al. |
| 6,979,675 B2 | 12/2005 | Tidmarsh |
| 7,173,025 B1 | 2/2007 | Stocker et al. |
| 7,858,782 B2 | 12/2010 | Tao et al. |
| 8,133,900 B2 | 3/2012 | Hood et al. |
| 8,257,741 B2 | 9/2012 | Curatolo et al. |
| 8,263,128 B2 | 9/2012 | Curatolo et al. |
| 8,337,899 B2 | 12/2012 | Curatolo et al. |
| 8,367,118 B2 | 2/2013 | Curatolo et al. |
| 8,431,159 B2 | 4/2013 | Curatolo et al. |
| 8,465,673 B2 | 6/2013 | Yasuda et al. |
| 9,474,779 B2 | 10/2016 | Lemieux et al. |
| 9,850,277 B2 | 12/2017 | Popovici-Muller et al. |
| 9,968,595 B2 | 5/2018 | Gu |
| 10,111,882 B2 | 10/2018 | Abella et al. |
| 2002/0049310 A1 | 4/2002 | Tateishi et al. |
| 2002/0188027 A1 | 12/2002 | Robinson et al. |
| 2003/0095958 A1 | 5/2003 | Bhisetti et al. |
| 2003/0109527 A1 | 6/2003 | Jin et al. |
| 2003/0207882 A1 | 11/2003 | Stocker et al. |
| 2003/0213405 A1 | 11/2003 | Harada et al. |
| 2004/0067234 A1 | 4/2004 | Einat et al. |
| 2004/0248221 A1 | 12/2004 | Stockwell |
| 2005/0261268 A1 | 11/2005 | Arnost et al. |
| 2006/0084645 A1 | 4/2006 | Pal et al. |
| 2006/0281122 A1 | 12/2006 | Bryant et al. |
| 2007/0244088 A1 | 10/2007 | Brickmann et al. |
| 2008/0132490 A1 | 6/2008 | Bergman et al. |
| 2008/0300208 A1 | 12/2008 | Einat et al. |
| 2009/0093526 A1 | 4/2009 | Miller et al. |
| 2009/0163508 A1 | 6/2009 | Kori et al. |
| 2009/0163545 A1 | 6/2009 | Goldfarb |
| 2009/0281089 A1 | 11/2009 | Gunzner et al. |
| 2009/0286752 A1 | 11/2009 | Etter et al. |
| 2010/0129350 A1 | 5/2010 | Zacharie et al. |
| 2010/0144722 A1 | 6/2010 | Alexander et al. |
| 2010/0273808 A1 | 10/2010 | Armitage et al. |
| 2010/0331307 A1 | 12/2010 | Salituro et al. |
| 2011/0073007 A1 | 3/2011 | Yasuda et al. |
| 2011/0086088 A1 | 4/2011 | Berry |
| 2011/0288065 A1 | 11/2011 | Fujihara et al. |
| 2012/0121515 A1 | 5/2012 | Deng et al. |
| 2012/0129865 A1 | 5/2012 | Wang et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0109643 A1 | 5/2013 | Riggins et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2013/0197106 A1 | 8/2013 | Fantin et al. |
| 2014/0094503 A1 | 4/2014 | Ma et al. |
| 2014/0187435 A1 | 7/2014 | Dang et al. |
| 2014/0206673 A1 | 7/2014 | Cao et al. |
| 2014/0213580 A1 | 7/2014 | Cao et al. |
| 2015/0018328 A1 | 1/2015 | Konteatis et al. |
| 2015/0031627 A1 | 1/2015 | Lemieux et al. |
| 2015/0031641 A1 | 1/2015 | Levine et al. |
| 2015/0044716 A1 | 2/2015 | Balss et al. |
| 2015/0087600 A1 | 3/2015 | Popovici-Muller et al. |
| 2015/0240286 A1 | 8/2015 | Dang et al. |
| 2015/0299115 A1 | 10/2015 | Popovici-Muller et al. |
| 2016/0130298 A1 | 5/2016 | Lemieux et al. |
| 2016/0264621 A1 | 9/2016 | Popovici-Muller et al. |
| 2016/0304556 A1 | 10/2016 | Popovici-Muller et al. |
| 2017/0007661 A1 | 1/2017 | Gu |
| 2017/0014396 A1 | 1/2017 | Gu |
| 2017/0015703 A1 | 1/2017 | Popovici-Muller et al. |
| 2017/0057994 A1 | 3/2017 | Lemieux et al. |
| 2018/0296583 A1 | 10/2018 | Agresta et al. |
| 2018/0303808 A1 | 10/2018 | Agresta |
| 2018/0303840 A1 | 10/2018 | Chopra et al. |
| 2019/0046512 A1 | 2/2019 | Amatangelo et al. |

FOREIGN PATENT DOCUMENTS

| | | |
|---|---|---|
| CN | 102659765 A | 9/2012 |
| CN | 103097340 A | 5/2013 |
| DE | 2263878 A1 | 7/1973 |
| DE | 3314663 A1 | 10/1983 |
| DE | 3512630 A1 | 10/1986 |
| EP | 0022958 A1 | 1/1981 |
| EP | 0384228 A1 | 8/1990 |
| EP | 0385237 A2 | 9/1990 |
| EP | 901786 A2 | 3/1999 |
| EP | 0945446 A1 | 9/1999 |
| EP | 1391487 A2 | 2/2004 |
| EP | 1886673 A2 | 2/2008 |
| FR | 2735127 A1 | 12/1996 |
| GB | 1033266 A | 6/1966 |
| JP | H04099768 A | 3/1992 |
| JP | H05140126 A | 6/1993 |
| JP | H09291034 A | 11/1997 |
| JP | H11158073 A | 6/1999 |
| JP | 2004107220 A | 4/2004 |
| JP | 2005264016 A | 9/2005 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2013519858 A | 5/2013 |
| MX | 2013/000614 A | 6/2013 |
| TW | 201028381 A | 8/2010 |
| WO | 1996030343 A1 | 10/1996 |
| WO | 9728128 A1 | 8/1997 |
| WO | 9728129 A1 | 8/1997 |
| WO | 1997044322 A1 | 11/1997 |
| WO | 9932463 A1 | 7/1999 |
| WO | 00002864 A1 | 1/2000 |
| WO | 2001016097 A1 | 3/2001 |
| WO | 2001019788 A2 | 3/2001 |
| WO | 2001019798 A2 | 3/2001 |
| WO | 0147897 A1 | 7/2001 |
| WO | 2001064642 A2 | 9/2001 |
| WO | 2001064643 A2 | 9/2001 |
| WO | 2002100822 A1 | 12/2002 |
| WO | 2002102313 A2 | 12/2002 |
| WO | 030016289 A1 | 2/2003 |
| WO | 2004009562 A1 | 1/2004 |
| WO | 2004046120 A2 | 6/2004 |
| WO | 2004050033 A2 | 6/2004 |
| WO | 2004073619 A2 | 9/2004 |
| WO | 2004074438 A2 | 9/2004 |
| WO | 2004089470 A2 | 10/2004 |
| WO | 2005035507 A2 | 4/2005 |
| WO | 2005060956 A1 | 7/2005 |
| WO | 2005065691 A1 | 7/2005 |
| WO | 2005103015 A1 | 11/2005 |
| WO | 2005120474 A2 | 12/2005 |
| WO | 2006034341 A2 | 3/2006 |
| WO | 2006038594 A1 | 4/2006 |
| WO | 2006070198 A1 | 7/2006 |
| WO | 2006079791 A1 | 8/2006 |
| WO | 2006/110761 A1 | 10/2006 |
| WO | 2007003934 A2 | 1/2007 |
| WO | 2007023186 A1 | 3/2007 |
| WO | 2008036835 A2 | 3/2008 |
| WO | 2008050168 A1 | 5/2008 |
| WO | 2008050186 A1 | 5/2008 |

(56) References Cited

FOREIGN PATENT DOCUMENTS

| WO | 2008052190 | A2 | | 5/2008 | |
|---|---|---|---|---|---|
| WO | 2008070661 | A1 | | 6/2008 | |
| WO | 2008073670 | A2 | | 6/2008 | |
| WO | 2008076883 | A2 | | 6/2008 | |
| WO | 2008131547 | A1 | | 11/2008 | |
| WO | 2008154026 | A1 | | 12/2008 | |
| WO | 2009013126 | A1 | | 1/2009 | |
| WO | 2009015254 | A1 | | 1/2009 | |
| WO | 2009016410 | A2 | | 2/2009 | |
| WO | 2009118567 | A2 | | 10/2009 | |
| WO | 2009126863 | A2 | | 10/2009 | |
| WO | 2009150248 | A1 | | 12/2009 | |
| WO | 2010007756 | A1 | | 1/2010 | |
| WO | WO-2010019239 | A2 | * | 2/2010 | ........... A61K 9/1635 |
| WO | 2010028099 | A1 | | 3/2010 | |
| WO | 2010105243 | A1 | | 9/2010 | |
| WO | 2010129596 | A1 | | 11/2010 | |
| WO | 2010130638 | A1 | | 11/2010 | |
| WO | 2010144338 | A1 | | 12/2010 | |
| WO | 2010144404 | A1 | | 12/2010 | |
| WO | 201105210 | A1 | | 1/2011 | |
| WO | 2011002817 | A1 | | 1/2011 | |
| WO | 2011/027249 | A2 | | 3/2011 | |
| WO | 2011032169 | A2 | | 3/2011 | |
| WO | 2011047432 | A1 | | 4/2011 | |
| WO | 2011050210 | A1 | | 4/2011 | |
| WO | 2011072174 | A1 | | 6/2011 | |
| WO | 2012006506 | A1 | | 1/2012 | |
| WO | 2012009678 | A1 | | 1/2012 | |
| WO | 2012074999 | A1 | | 6/2012 | |
| WO | 2012078288 | A2 | | 6/2012 | |
| WO | 2012092442 | A1 | | 7/2012 | |
| WO | 2012151452 | A1 | | 11/2012 | |
| WO | 2012160034 | A1 | | 11/2012 | |
| WO | 2012171337 | A1 | | 12/2012 | |
| WO | 2012171506 | A1 | | 12/2012 | |
| WO | 2012173682 | A2 | | 12/2012 | |
| WO | 2013004332 | A1 | | 1/2013 | |
| WO | 2013007708 | A1 | | 1/2013 | |
| WO | 2013016206 | A1 | | 1/2013 | |
| WO | 2013102431 | A1 | | 7/2013 | |
| WO | 2013107291 | A1 | | 7/2013 | |
| WO | 2013107405 | A1 | | 7/2013 | |
| WO | 2013133367 | A1 | | 9/2013 | |
| WO | 2014015422 | A1 | | 1/2014 | |
| WO | 2015/003360 | A2 | | 1/2015 | |
| WO | 2015127172 | A1 | | 8/2015 | |
| WO | 2015127173 | A1 | | 8/2015 | |
| WO | 2015138837 | A1 | | 9/2015 | |
| WO | 2015138839 | A1 | | 9/2015 | |
| WO | 2017066566 | A1 | | 4/2017 | |
| WO | 2017066571 | A1 | | 4/2017 | |
| WO | 2017096309 | A1 | | 6/2017 | |
| WO | 2017146795 | A1 | | 8/2017 | |

OTHER PUBLICATIONS

Birendra et al. "Evidence for clinical differentiation and differentiation syndrome in patients with acute myeloid leukemia and IDH1 mutations treated with the targeted mutant IDH1 inhibitor, AG-120," Clinical Lymphoma, Myeloma & Leukemia, 2016, 16(8):460-5.

Caunt et al. "MEK1 and MEK2 inhibitors and cancer therapy: the long and winding road," Nature Reviews Cancer, 2015, 15(10):577-592.

Dinardo et al. "Characteristics, clinical outcome, and prognostic significance of IDH mutations in AML," American Journal of Hematology, 2015, 90(8):732-736.

Dinardo et al. "Molecular profiling and relationship with clinical response in patients with IDH1 mutation-positive hematologic malignancies receiving AG-120, a first-in-class potent inhibitor of mutant IDH1, in addition to data from the completed dose escalation portion of the phase 1 study," Blood, 2015, 126:1306.

Dohner et al. "Acute myeloid leukemia," New England Journal of Medicine, 2015, 373:1136-52.

Green et al. "The prognostic significance of IDH1 mutations in younger adult patients with acute myeloid leukemia is dependent on FLT3/ITD status," Blood, 2010, 116(15):2779-2782.

Gura. "Systems for identifying new drugs are often faulty," Science, 1997, 278(5340):1041-2.

Hansen et al. "AG-120, an oral, selective, first-in-class, potent inhibitor of mutant IDH1, reduces intracellular 2HG and induces cellular differentiation in TF-1 R132H cells and primary human IDH1 mutant AML patent samples treated ex vivo," Blood, 124(21):3734.

Hemerly et al. "Identification of several novel non-p.R132 IDH1 variants in thyroid carcinomas," European Journal of Endocrinology, 2010, 163(5):747-755.

Im et al. "DNMT3A and IDH mutations in acute myeloid leukemia and other myeloid malignancies: Associations with prognosis and potential treatment strategies," Leukemia, 2014, 28:1774-1783.

Johannessen et al. "Rapid conversion of mutant IDH1 from driver to passenger in model of human gliomagenesis," Molecular Cancer Resarch, 2016, 14(10): 976-83.

Johnson et al. "Relationships between drug activity in NCI preclinical in vitro and in vivo models and early clinical trials," British Journal of Cancer, 2001, 84(10): 1424-1431.

Ramos et al. "Current approaches in the treatment of relapsed and refractory acute myeloid leukemia," Journal of Clinical Medicine, 2015, 4(4):665-695.

Wei Chao et al. Teaching Materials of the 12th Five-Year Paln for the Relevant Majors of Pharmacy in the Specialty and Polytechnic Colleges, Pharmacy (2nd edition), Henan Science and Technology Press, 2012.

Yuan et al. "Role of IDH1 gene mutation in the genesis of glioblastoma," Medical Journal of Wuhan University, 2011, 32(2):164-166.

Aghili et al. "Hydroxyglutaric aciduria and malignant brain tumor: a case report and literature review", Journal of Neuroncology, 2008. 91:233-236.

Amary et al. "Oilier disease and Maffucci syndrome are caused by somatic mosiac mutations of IDH1 and IDH2," Nature Genetics Letters, 2011, 43(12):1262-1266.

Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.

Balss, "Analysis of the IDH1 codon 132 mutation in brain tumors", Acata Neuropathol (2008) vol. 116, pp. 597-602.

Benner et al, "Evolution, language and analogy in functional genomics", Trends in Genetics (2001) vol. 17, pp. 414-418.

Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.

Bleeker et al., "IDH1 mutations at residue p. R132 (IDH1 (R132)) occur frequently in high-grade 18-22 gliomas but not in other solid tumors." Hum Muta1., Jan. 2009, vol. 30, No. 1, pp. 7-11.

Braun et al. "Triazine-based polymers: 4. MALDI-MS of triazine-based polyamines" Polymer (1996) vol. 37, No. 5, pp. 777-783.

Burger et al. "Nuclear substituted 3,4-dihydroxyphenethylamines and related derivatives," Journal of American Chemical Society, 1956, 78(17):4419-4422.

Cairns et al. "Oncogenic Isocitrate Dehydrogenase Mutations: Mechanisms, Models, and Clinical Opportunities" Cancer Discovery (2013) vol. 3, Iss 7, pp. 730-741.

Cecil Textbook of Medicine, edited by Bennet, J.C., and Plum F., 20th edition, vol. 1, 1004-1010, 1996.

Chan et al. "Multi-domain hydrogen-bond forming metal chelates: X-ray crystal structuresof dicyclopalladated 2,3-bis[6-(2-amino-4-phenylamino-1 ,3,5-triazinyl)]pyrazine(H2L) [Pd2Br2L] and 2,6-bis[6-(2-amino-4-phenylamino-1,3,5-triazinylium)]-pyridine dichloride" Chemical Communications (1996) No. 1, pp. 81-83.

Chapman et al. "Substituted aminopyrimidine protein kinase B (PknB) inhibitorsshow activity against *Mycobacterium tuberculosis*" Bioorganic Medicinal Chemistry Letters (2012) vol. 22, pp. 3349-3353.

(56) References Cited

OTHER PUBLICATIONS

Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry, 1995. vol. 32 pp. 543-545.
Dang et al., "Cancer-associated IDH1 mutations produce 2-hydroxyglutarate." Nature, 10 29-32 Dec. 2009, vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Database CA [Online] Chemical Abstracts Service, Columbus,Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes ( 2011 ), 64(4), 544-550 Coden: KZARF3; ISSN: 1561-4190, 2011.
Database CA [Online] Chemical Abstracts Service. Columbus.Ohio. US; Baibulova M. S. et al:Syntheses from pyridylguanamines_ XP002764691. retrieved from STN Database accession No. 1990:406282 * abstract* & Bai Bulova, M. S. et al: Syntheses from pyridylguanamines, Izvestiya Akademii Nauk Kazakhskoi SSR, Seriya Khimicheskaya, (5), 40-2 Coden: Ikakak; ISSN: 0002-3205, 1989.
Database CA [Online] Chemical Abstracts Service. Columbus.Ohio. US; Krimmer. Hans Peter et al: "Reaction of .beta.-mercapto .alpha.-amino acids with nitriles".XP002764690.retrieved from STN Database accession No. 1988:529623* abstract* & Krimmer. Hans Peter et al: "Reaction of .beta.-mercapto .alpha.-amino acids with nitriles".Chemiker-Zeitung â€¢ 111(12). 357-61 Coden: CMKZAT; ISSN: 0009-2894.1987.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Dermer et al., "Another Anniversary for the War on Cancer", Bio/Technology, 1994, 12:320.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Impact of Genetic Features on Treatment Decisions in AML" American Society of Hematology (2011) pp. 36-42.
Drew, MGB, et al. "Solvent extraction and lanthanide complexation studies with new terdentate ligands containing two 1, 3, 5-triazine moieties." Dalton Transactions 2 (2004): 244-251.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
Enholm, EJ., Jed M. Hastings, and Chris Edwards. "Hydrogen-Bonded Arrays Coupled by Cross-Metathesis." Synlett Feb. 2008 (2008): 203-206.
EP Search Report & Written Opinion for EP 10825706 dated Mar. 20, 2013.
European Search Report for Application No. 10751525.6 dated Dec. 14, 2012.
European Search Report for European Application No. 12799802.9 dated Sep. 24, 2014.
European Search Report for European Application No. EP 12800001.5 dated Oct. 10, 2014.
Eurpoean Search Report for EP Application No. 11763425.3 dated Sep. 23, 2013.
Extended European Search Report for PCT/CN2014081957 dated Dec. 9, 2016.

Freshney et al.,Culture of Animal Cells, A Manual of Basic Technique, Alan R. Liss, Inc., 1983, New York, p. 4.
Genetics Home Reference. "L2HGDH." accessed at <http://ghr.nlm.nih.gov/gene/L2HGDH> on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al., "Molecular Classification of Cancer: Class Discovery and Class Prediction by Gene Expression Monitoring", Science, 286, 531-537, 1999.
Hartmann et al. "Type and Frequency of IDH1 and IDH2 mutations are related to astrocytic and oligodendroglial differentiation and age: a study of 1010 diffuse gliomas" Acta Neuropathologica (2009) 118: 469-474.
Ho et al., "Triazine and pyrimidine based ROCK inhibitors with efficacy in spontaneous hypertensive rat model." Bioorganic & Medicinal Chemistry Letters (2009) vol. 19, pp. 6027-6031.
Holmes et al, 750 MHz 1H NMR spectroscopy characterisation of the complex metabolic pattern of urine from patients with inborn errors of metabolism: 2-hydroxyglutaric aciduria and maple syrup urine disease., Journal of Pharmaceutical and Biomedical Analysis (1997) vol. 15, pp. 1647-1659.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.
International Search Report for PCT/CN2013/000068 dated Apr. 25, 2013.
International Search Report for PCT/US2010053624 dated Apr. 7, 2011.
International Preliminary Report for related application No. PCT/US2010/059778 dated Jun. 21, 2012.
International Preliminary Report for related application No. PCT/US2011/067752 dated Apr. 11, 2013.
International Preliminary Report on Patentability for Application No. PCT/US2010/053623 dated Apr. 24, 2012.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 dated Sep. 13. 2011.
International Preliminary Report on Patentability for PCT/US2010/040486 dated Jan. 12, 2012.
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4- [[4-(4-pyridinyl)-1-piperazinyl]carbonyl]phenyl]-".

(56) References Cited

OTHER PUBLICATIONS

STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-1-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-1-piperazinyl)carbonyl]phenyl]-".
Struys et al, Investigations by mass isotopomer analysis of the formation of D-2-hydroxyglutarate by cultured lymphoblasts from two patients with D-2-hydroxyglutaric aciduria, FEBS letters 92004 vol. 557, pp. 115-120.
Struys et al. "Mutations in the D-2-hydroxyglutarate dehydrogenase gene cause D-2-hydroxyglutaric aciduria" American Journal of Human Genetics, 2005. 76:358-360.
Struys, EA. et al. "Measurement of Urinary D- and L-2-Hydroxyglutarate Enantiomers by Stable-Isotope-Dilution LiquidChromatography—Tandem Mass Spectrometry after Derivatization with Diacetyi-L-Tartaric Anhydride." Clinical Chemistry (2004)501391-1395.
Supplementary European Search Report for EP Application No. 10825707.2 dated Jun. 28, 2013.
Supplementary European Search Report for EP15761216 dated Oct. 5, 2017.
Supplementary Search Report for EP10794668 dated Oct. 18, 2012.
Supplimentary European Search Report for EP 10751525 dated Dec. 14, 2012.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England 18-22 Journal of Medicine, Feb. 19, 2009, vol. 360, No. 8, pp. 813-815; p. 813, p. 815, col. 1; Fig 1.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-PyrimidineDerivatives" Journal of Heterocyclic Chemistry (2010) vol. 47 pp. 1056-1061.

Wang et al. "A novel ligand N,N?-di(2-pyridyl)-2,4-diamino-6-phenyl-1,3,5-triazine (dpdapt) and its complexes: [Cu (dpdapt)Cl2] and [Cu(dpdapt)(NO3)(H2O)] Â• NO3 Â• H2O" Polyhedron, 2006. vol. 25, Issue 1. pp. 195-202.
Ward, Patrick S, "The Common Feature of Leukemia-Associated IDH1 and IDH2 Mutations Is a Neomorphic Enzyme Activity Converting [alpha]-Ketoglutarate to 2-Hydroxyglutarate" Cancer cell, vol. 17,Nr:3,pp. 225-234, 2010.
Watanabe et al., "IDH1 Mutations Are Early Events in the Development of Astrocytomas and Oligodendrogliomas". American Journal of Pathology, Apr. 2009 (published online Feb. 26, 2009, vol. 174, No. 4, pp. 1149-1153; Abstract, p. 1150, col. 1.
Written Opinion for PCT/US2010/027253 dated Aug. 19, 2010.
Written Opinion for SG 11201600185U dated Nov. 16, 2016.
Written Opinion of International Search Authority for PCT/CN2013/000009 dated Apr. 18, 2013.
Written Opinion of Search Authority for PCT/US2010/53623 dated Jan. 18, 2011.
Nritten Opinion of the International Searching Authority for PCT/US2011/067752 dated Mar. 5, 2012.
Yan et al., "IDH1 and IDH2 Mutations in Gliomas" The New England Journal of Medicine, 79 Feb. 18-22, 2009, vol. 360, No. 8, pp. 765-773.
Yrjola et al., "Discovery of novel cannabinoid receptor ligands by a virtual screening approach: Further development of 2,4,6-trisubstituted 1,3,5-triazines as CB2 agonists," European Journal of Pharmaceutical Sciences (2013) vol. 48, pp. 9-20.
Zhao et al: "Glioma-derived mutations in IDH1 dominantly inhibit IDH1 catalytic activity and induce HIF-1alpha", Science, vol. 324, No. 5924, Apr. 10, 2009 (Apr. 10, 2009), pp. 261-265.
Zheng et al. "Synthesis and antitumor evaluation of a novel series of triaminotriazine derivatives" Bioorganic & Medicinal Chemistry (2007) vol. 15, pp. 1815-1827.
Zuo et al. "Synthesis of 4-methyl-1,2,3-thiadiazole derivatives via ugi reaction and their biological activities," Journal of Agricultural and Food Chemistry, 2010, 58(5): 2755-2762.
International Preliminary Report on Patentability for PCT/US2010/053624 dated Apr. 7, 2011.
International Preliminary Report on Patentability for PCT/US2011/030692 dated Oct. 2, 2012.
International Search Report & Written Opinion for PCT/CN2013/070755 dated Apr. 25, 2013.
International Search Report and Written Opinion for Internatinal Application No. PCT/US2013/064601 dated Feb. 24, 2014.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report and Written Opinion for International Application No. PCT/US15/020349 dated Jun. 15, 2015.
International Search Report and Written Opinion for International Application No. PCT/US2014/046202 dated Sep. 30, 2014.
International Search Report and Written Opinion for International Application No. PCT/US2014/049469 dated Jan. 22, 2015.
International Search Report and Written Opinion for International Application No. PCT/US2015/020346 dated Jun. 18, 2015.
International Search Report dated Mar. 5, 2012 for related international application No. PCT/US2011/067752.
International Search Report for International Application No. PCT/CN2013/079184 dated Jan. 12, 2015.
International Search Report for International Application No. PCT/CN2013/079200 dated Jan. 12, 2015.
International Search Report for International Application No. PCT/CN2014/082869 dated Sep. 30, 2014.
International Search Report for International Application No. PCT/US2014/046204 dated Oct. 1, 2014.
International Search Report for PCT/CN2012/000841 dated Sep. 27, 2012.

(56) References Cited

OTHER PUBLICATIONS

International Search Report for PCT/CN2012/077096 dated Oct. 4, 2012.
International Search Report for PCT/CN2013/000009 dated Apr. 18, 2013.
International Search Report for PCT/US10/040486 dated Sep. 1, 2010.
International Search Report for PCT/US201/030692 dated Jul. 27, 2011.
International Search Report for PCT/US2010/027253 dated Aug. 19, 2010.
International Search Report for PCT/US2010/059778 dated Mar. 17, 2011.
International Search Report for PCT/US2010/53623 dated Jan. 18, 2011.
International Search Report for PCT/US2011044254 dated May 10, 2011.
International Search Report for PCT/US2013/064601 dated Feb. 24, 2014.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.
Jennings et al, Expression and mutagenesis of mammalian cytosolic NADP+-specific isocitrate dehydrogenase, Biochemistry (1997)vol. 36, pp. 13743-13747.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al "Ser95, Asn97, and Thr78 are important for the catalytic function of porcine NADP-dependent isocitrate dehydrogenase" Protein Science (2005) 14: pp. 140-147.
Kim et al. "Identification and Functional Characterization of a Novel, Tissue-specific NAD1-dependent Isocitrate Dehydrogenase b Subunit Isoform" JBC. Dec. 24, 1999, vol. 274 No. 52 pp. 36866-36875.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kumar et al. "Pharmaceutical solid dispersion technology: A strategy to improve dissolution of poorly water-soluable drugs," Recent Patents on Drug Delivery and Formulation, 2013, 7:111-121.
Kumar et al., "4-Anilinoquinoline triazines: A novel class of hybrid antimalarial agents" European Journal of Medicinal Chemistry (2011) vol. 46, pp. 676-690.
Kumar et al., "Synthesis and bioevaluation of hybrid 4-aminoquinoline triazines as a new class of antimalarial agents," Bioorganic & Medicinal chemistry Letters (2008) vol. 18, pp. 6530-6533.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou. "IDH1: function follows form." SciBX, 2009, 1-2.
Lowe, "Good old medicinal chemistry: what can you get away with?," Blog "In the Pipeline," entry of Nov. 2, 2010.
Lutker et al, "Crystal Polymorphism in a Carbamazepine Derivative: Oxcarbazepine". NIH Public Access. J Pharm Sci. Feb. 2010; 99(2): 794-803. doi: 10.1002/jps.21873.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
Maison, "Multicomponent synthesis of novel amino acid-nucleobase chimeras: a versatile approach to PNA-monomers," Bioorganic & Medicinal Chemistry (2000) vol. 8, pp. 1343-1360.
May et al, How many species are there on earth, Science (1988) vol. 241, p. 1441.
McRobbie et al. "MRI from Picture to Proton," Cambridge University Press, 2007, pp. 307-308.
Hashida, Design and Evaluation of Oral Administration Formulations, Jiho Inc., 1995, 172-185.
Hashida, Design and Evaluation of Oral Administration Formulations, Jiho Inc., 1995, 76-79.
Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.
Mikhaylichenko, Svetlana, et al. "Synthesis and structure of new 1, 2, 3-triazolyl substituted 1, 3, 5-triazines." European Journal of Chemistry 3.1 (2012): 1-9.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science vol. 321 (2008) pp. 1807-1812 and Supplemental Data.
Pitts et al., "Rapid Synthesis of Triazine Inhibitors of Inosine Monophosphate Dehydrogenase," Bioorganic & Medicinal Chemistry Letters (2002) vol. 12, pp. 2137-2140.
Pollard et al, "Cancer. Puzzling patterns of predisposition." Science. Apr. 10, 2009, vol. 324, 1-5,15-16, 18-22,35-38 No. 5924, pp. 192-194.
Popovici-Muller, Janeta et al. Discovery of the First Potent Inhibitors of Mutant IDH1 That Lower Tumor2-HG in Vivo. ACS Medicinal Chemistry Letters. Sep. 17, 2012 (Sep. 17, 2012), vol. 3, No. 10, 850-855.
PubChem CID 4078245 [online]; Sep. 13, 2005 [retrieved on Feb. 4, 2012]; retrieved from http://pubchem.ncbi.nim.nih.gov/; 2d-structure.
PubChem CID 4854170 [online]; Sep. 17, 2005 [retrieved on Feb. 4, 2012]; retrieved from http://pubchem.ncbi.nim.nih.gov/; 2d-structure.
Rao et al., "Polymorphism in Drugs and its Significance in Therapeutics". Journal of Scientific & Industrial Research vol. 46 Oct. 1987 pp. 450-455.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Jul. 3, 2008, CAS Registration No. 1032461-94-1.
Registry (STN) [online], Jul. 3, 2008, CAS Registration No. 1032470-22-6.
Registry (STN) [online], Jul. 4, 2008, CAS Registration No. 1032747-65-1.

(56) References Cited

OTHER PUBLICATIONS

Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Registry (STN) [online], Apr. 16, 2010, CAS Registration No. 1219379-97-1.
Reitman et al. "Isocitrate Sehydrogenase 1 and 2 Mutations in Cancer: Alterations at a Crossroads of Cellular Metabolism" Journal of the National Cancer Institute, vol. 102, No. 13, pp. 932-941 (2010).
Rohle et al. "An Inhibitor of Mutant IDH1 Delays Growth and Promotes Differentiation of Glioma Cells" Science, vol. 340, No. 6132 pp. 626-630 (2013).
Scharn et al. "Spatially Addressed Synthesis of Amino-and Amino-Oxy-Substituted 1,3,5-Triazine Arrays on Polymeric Membranes" Journal of Combinatorial Chemistry (2000) vol. 2, No. 4, pp. 361-369.
Search Report for SG 11201600185U dated Nov. 16, 2016.
Serajuddin et al. "Solid dispersion of poorly water-soluable drugs: early promises, subsequent problems, and recent breakthroughs," Journal of Pharmaceutical Sciences, 1999, 88(10):1058-1066.
Shahin et al., "Elaborate ligand-based modeling and subsequent synthetic exploration unveil new nanomora Ca2+/Calmodulin-dependent protein kinase II inhibitory leads" Bioorganic & Medicinal Chemistry (2012) vol. 20, pp. 377-400.
Shih et al. "The Role of Mutations in Epigenetic Regulators in Myeloid Malignancies" Nature Reviews Cancer (2012) vol. 12, No. 9, pp. 599-612.
Sirkanyan, S.N. et al Synthesis of new derivatives of piperazine-substituted pyrano[3,4-c]pyridines. Hayastani Kimiakan Handes 2009, vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI." Curr. Op. Biotech., 2007, 18, 4-10.
STN file CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile,3,4-dihydro-3,3-dimethyl-6-[4-(1-oxobutyl)-1-piperazinyl]-8-phenyl-", disclosed in Paronikyan et al. Armyanskii Khimicheskii Zhumal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile,3,4-dihydro-3,3-dimethyl-6-[4-(2-methyl-1-oxopropyl)-1-piperazinyl]-8-phenyl-", disclosed in Paronikyan et al. Armyanskii Khimicheskii Zhumal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhumal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile,6-[4-(2-furanylcarbonyl)-1-piperazinyl]-3,4-dihydro-3,3-dimethyl-8-phenyl-", disclosed in Paronikyan et al. Armyanskii Khimicheskii Zhumal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN file CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd., Entered STN: Jul. 3, 2008 (Jul. 3, 2008).
STN Registry. L23 Answer 1 of 3 (CAS No. 1038821-72-5), Database: ChemDB (University of Califomia Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-1-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazol)methyl]-1-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pridinyl)-I-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
Friesen et al. "Hydroxypropyl Methylcellulose Acetate Succinate-Based Spray-Dried Dispersions: An Overview," Molecular Pharmaceutics, 2008, 5(6):1003-1019.
U.S. Appl. No. 13/810,410, filed Mar. 28, 2013, Janeta Popovici-Muller.
U.S. Appl. No. 15/064,874, filed Mar. 9, 2016, Janeta Popovici-Muller.
U.S. Appl. No. 13/745,005, filed Jan. 18, 2013, Rene M. Lemieux.
U.S. Appl. No. 14/988,661, filed Jan. 5, 2016, Rene M. Lemieux.
U.S. Appl. No. 15/279,146, filed Sep. 28, 2016, Janeta Popovici-Muller.
U.S. Appl. No. 15/809,325, filed Nov. 10, 2017, Janeta Popovici-Muller.
U.S. Appl. No. 14/373,154, filed Jul. 18, 2014, Janeta Popovici-Muller.
U.S. Appl. No. 15/196,842, filed Jun. 29, 2016, Janeta Popovici-Muller.
U.S. Appl. No. 14/341,426, filed Jul. 25, 2014, Rene M. Lemieux.
U.S. Appl. No. 15/347,407, filed Nov. 9, 2016, Rene M. Lemieux.
U.S. Appl. No. 15/915,213, filed Mar. 8, 2018, Rene M. Lemieux.
U.S. Appl. No. 15/125,884, filed Sep. 13, 2016, Chong-Hui Gu.
U.S. Appl. No. 15/125,880, filed Sep. 13, 2016, Chong-Hui Gu.
U.S. Appl. No. 15/767,813, filed Apr. 12, 2018, Samuel V. Agresta.
U.S. Appl. No. 15/767,822, filed Apr. 12, 2018, Samuel V. Agresta.
U.S. Appl. No. 15/781,019, filed Jun. 1, 2018, Bin Wu.
Emadi et al. "Presence of isocitrate dehydrogenase mutations may predict clinical response to hypomethylating agents in patients with acute myeloid leukemia," American Journal of Hematology, 2015, 90(5):E77-E79.
Lazzarino et al. "Mitoxantrone and etoposide: An effective regimen for refractory or relapsed acute myelogenous leukemia," European Journal of Haematology, 1989, 43:411-416.
Shuichi et al. "Long-term follow-up of the randomized JALSG AML 201 study comparing high dose Ara-C therapy with conventional consolidation therapy in adult acute myeloid leukemia (AML)," Blood, 2008, 112(11):135.
Astellas, "Dose escalation study investigating the safety, tolerability, pharmacokinetics, pharmacodynamics of ASP2215 in patients with relapsed or refractory acute myeloid leukemia," (Astellas

(56) References Cited

OTHER PUBLICATIONS

Pharma Global Development, Inc., https://clinicaltrials.gov/ct2/history/NCT02014558?V_11=View#StudyPageTop, Dec. 12, 2013 (v1), obtained from the internet Jun. 21, 2019).

Dohner et al. "Impact of genetic features on treatment decisions in AML" ASH Education Program Book, 2011, 1:36-42.

Levis et al. "Results of a first-in-human, phase I/II trial of ASP2215, a selective, potent inhibitor of FLT3/Axl in patients with relapsed or refractory (R/R) acute myeloid leukemia," Journal of Clinical Oncology, 2015, 33(15 suppl):7003.

Shafer et al. "Update on rational tareted therapy in AML," Blood Reviews, 2016, 30:275-283.

* cited by examiner

PHARMACEUTICAL COMPOSITIONS OF THERAPEUTICALLY ACTIVE COMPOUNDS

CLAIM OF PRIORITY

This application is a continuation of U.S. Ser. No. 15/125,880, filed Sep. 13, 2016, which is a national stage application under 35 U.S.C. § 371 of International Application No. PCT/US2015/020349, filed Mar. 13, 2015, which claims priority from U.S. Ser. No. 61/953,487 filed Mar. 14, 2014, and U.S. Ser. No. 62/081,542 filed Nov. 18, 2014, each of which is incorporated herein by reference in its entirety.

BACKGROUND OF THE INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2,4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684 (1998); Geisbrecht et al., J. Biol. Chem. 274:30527-30533 (1999); Wiemann et al., Genome Res. 11:422-435 (2001); The MGC Project Team, Genome Res. 14:2121-2127 (2004); Lubec et al., Submitted (December 2008) to UniProtKB; Kullmann et al., Submitted (June 1996) to the EMBL/GenBank/DDBJ databases; and Sjoeblom et al., Science 314:268-274 (2006).

Non-mutant, e.g., wild type, IDH1 catalyzes the oxidative decarboxylation of isocitrate to α-ketoglutarate thereby reducing NAD$^+$ (NADP$^+$) to NADH (NADPH), e.g., in the forward reaction:

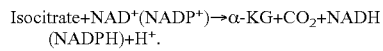

Isocitrate+NAD$^+$(NADP$^+$)→α-KG+CO$_2$+NADH (NADPH)+H$^+$.

It has been discovered that mutations of IDH1 present in certain cancer cells result in a new ability of the enzyme to catalyze the NAPH-dependent reduction of α-ketoglutarate to R(−)-2-hydroxyglutarate (2HG). The production of 2HG is believed to contribute to the formation and progression of cancer (Dang, L et al, Nature 2009, 462:739-44).

The inhibition of mutant IDH1 and its neoactivity is therefore a potential therapeutic treatment for cancer. Accordingly, there is an ongoing need for inhibitors of IDH1 mutants having alpha hydroxyl neoactivity.

PCT Publication No. WO 2013/107291 and US Publication No. US 2013/0190249 hereby incorporated by reference in their entirety, disclose compounds that inhibit IDH1 mutants (e.g., IDH1R132H or IDH1R132C). These applications additionally disclose methods for the preparation of inhibitors of mutant IDH1, pharmaceutical compositions containing these compounds, and methods for the therapy of diseases, disorders, or conditions (e.g., cancer) associated with overexpression and/or amplification of mutant IDH1.

There is a need for pharmaceutical compositions that would have properties suitable for large-scale manufacturing and formulation, as well as utility in treating advanced hematologic malignancies, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1.

SUMMARY OF INVENTION

Disclosed herein are methods of treating advanced hematologic malignancies, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising, administering to a subject in need thereof a solid dispersion or a pharmaceutical composition comprising a solid dispersion, and at least one pharmaceutically acceptable carrier. In some embodiments, the advanced hematologic malignancies are characterized by a mutant allele of IDH1, wherein the IDH1 mutation results in a new ability of the enzyme to catalyze the NAPH-dependent reduction of α-ketoglutarate to R(−)-2-hydroxyglutarate (2HG) in a patient. In one embodiment, the mutant IDH1 has an R132X mutation. In one embodiment, the R132X mutation is selected from R132H, R132C, R132L, R132V, R132S and R132G. In one embodiment, the R132X mutation is R132H or R132C. In one embodiment, the R132X mutation is R132H. In some embodiments, the advanced hematologic malignancies harbor a co-mutation, e.g., a co-mutation selected from NPM1, FLT3, TET2, CEBPA, DNMT3A, and MLL.

In one aspect, the present invention provides a method of evaluating a subject, the method comprising: acquiring, e.g., directly acquiring, a value for the level of a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1), or a pharmaceutically acceptable salt thereof; or the level of an alpha hydroxy neoactivity product, e.g., 2HG, e.g., R-2HG (2HG), in the subject, that has been treated with Compound 1, to thereby evaluate the subject.

In another aspect, the present invention provides a method of evaluating a subject, the method comprising: administering to the subject in need thereof a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1), or a pharmaceutically acceptable salt thereof; and acquiring a value for the level of Compound 1 or the level of an alpha hydroxy neoactivity product, e.g., 2HG, e.g., R-2HG (2HG), in the subject, to thereby evaluate the subject.

In some embodiments, acquiring comprises receiving a sample from the subject. In some embodiments, acquiring comprises transmitting the value to another party, e.g., the party that administered Compound 1.

In some embodiments, the value for the level of Compound 1 is acquired by analyzing the concentration of Compound 1 in a bodily fluid, e.g., blood, plasma or urine. In some embodiments, the value for the level of Compound 1 is acquired by analyzing the level of Compound 1 in bone marrow, e.g., analyzing a sample from a bone marrow biopsy and/or aspirate for the level of Compound 1.

In some embodiments, the value for the level of 2HG is acquired by analyzing the concentration of 2HG in a bodily fluid, e.g., blood, plasma or urine. In some embodiments, the value for the level of 2HG is acquired by analyzing the level of 2HG in bone marrow, e.g., analyzing a sample from a bone marrow biopsy and/or aspirate for the level of 2HG.

In some embodiments, the analysis is performed by sample analysis of bodily fluid, such as blood, plasma or urine, by e.g., a chromatographic method, e.g., mass spectroscopy, e.g. LC-MS. In some embodiments, the analysis is performed by spectroscopic analysis, e.g., magnetic resonance-based analysis, e.g., MRI and/or MRS measurement.

In some embodiments, the subject has been administered Compound 1 less than about 30 days prior to the evaluation, e.g., less than about 29 days, e.g., less than about 28 days, e.g., less than about 27 days, e.g., less than about 26 days, e.g., less than about 25 days, less than about 24 days, e.g., less than about 23 days, e.g., less than about 22 days, e.g., less than about 21 days, e.g., less than about 20 days, e.g., less than about 19 days, e.g., less than about 18 days, e.g., less than about 17 days, e.g., less than about 16 days, e.g., less than about 15 days, e.g., less than about 14 days, e.g., about 7 days, less than about 6 days, less than about 5 days, less than about 4 days, less than about 3 days, or less than 72 hours prior to the evaluation, e.g., less than 48 hours, less than 24 hours, less than 12 hours, less than 10 hours, less than 8 hours, less than 6 hours, less than 4 hours, less than 3 hours, less than 2 hours, less than 1.5 hours, less than 1 hour, less than 45 minutes, less than 30 minutes, or less than 15 minutes, prior to the evaluation.

In some embodiments, the subject has been administered, e.g., orally, Compound 1 at a dose of about 10 mg to about 3000 mg, e.g., once or twice daily, (e.g., about every 8-16 hours, e.g., about every 12 hours), or (e.g., about every 12-36 hours, e.g., about every 24 hours), e.g., at about 10 mg to about 60 mg, at about 60 mg to about 200 mg, at about 200 mg to about 500 mg, at about 500 mg to about 1200 mg, at about 1200 mg to about 2000 mg, or at about 2000 mg to about 3000 mg, e.g., at about 50 mg, at about 100 mg, at about 300 mg, at about 500 mg, at about 800 mg once or twice daily, e.g., about every 12 hours, or e.g., about every 24 hours, prior to the evaluation.

In some embodiments, the subject has or is diagnosed as having a disorder. In some embodiments, the disorder is an advanced hematologic malignancy, e.g., an advanced hematologic malignancy characterized by the presence of a mutant allele of IDH1. In some embodiments, the advanced hematologic malignancy is characterized by a mutant allele of IDH1, wherein the IDH1 mutation results in a new ability of the enzyme to catalyze the NAPH-dependent reduction of α-ketoglutarate to R(−)-2-hydroxyglutarate (2HG) in a patient. In one embodiment, the mutant IDH1 has an R132X mutation. In one embodiment, the R132X mutation is selected from R132H, R132C, R132L, R132V, R132S and R132G. In one embodiment, the R132X mutation is R132H or R132C. In one embodiment, the R132X mutation is R132H. In some embodiments, the advanced hematologic malignancy harbors a co-mutation, e.g., a co-mutation selected from NPM1, FLT3, TET2, CEBPA, DNMT3A, and MLL.

In some embodiments, the disorder is selected from acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), B-acute lymphoblastic leukemias (B-ALL), and lymphoma (e.g., T-cell lymphoma), wherein each is characterized by the presence of a mutant allele of IDH1. In some embodiments, the disorder is selected from advanced IDH1 mutation-positive relapsed and/or refractory AML (R/R AML), untreated AML, and MDS.

In some embodiments, the subject has been previously treated with one or more chemotherapeutic agent(s). In some embodiments, the chemotherapeutic agent is selected from cytarabine (Ara-C), daunorubicin, etoposide, mitoxantrone, idarubicin, 5-azacytidine, decitabine, SGN33A, sargramostim, WT-1 analog peptide vaccine, tipifarnib, MK-8242, campath, and 6 Mercaptopurine (6MP).

In another aspect, the present invention provides a method of evaluating a subject, the method comprising: acquiring, e.g., directly acquiring, a value for the level of blast cells, e.g., leukemic blast cells, e.g., myeloblasts or myeloid blasts, in the subject, that has been treated with a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1), to thereby evaluate the subject.

In another aspect, the present invention provides a method of evaluating a subject, the method comprising: administering to the subject in need thereof a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1), or a pharmaceutically acceptable salt thereof; and acquiring a value for the level of blast cells, e.g., leukemic blast cells, e.g., myeloblasts or myeloid blasts, in the subject, to thereby evaluate the subject.

In some embodiments, acquiring comprises receiving a sample from the subject. In some embodiments, acquiring comprises transmitting the value to another party, e.g., the party that administered Compound 1.

In some embodiments, the evaluation comprises acquiring a value for the level of blast cells, e.g., leukemic blast cells, e.g., myeloblasts or myeloid blasts, e.g., a blast cell count, in a sample from the subject, and comparing the value to a reference standard. In some embodiments, the reference standard is the total number of cells in the sample. In some embodiments, the sample comprises blast cells, myelocytes, neutrophils, promyelocytes, metamyelocytes, and monocytes.

In some embodiments, the value for the level of blast cells, e.g., leukemic blast cells, e.g., myeloblasts or myeloid blasts, is acquired by analyzing the bone marrow, e.g., by analyzing blast counts in bone marrow aspirates. In some embodiments, the bone marrow is analyzed, e.g., about every two weeks, e.g., (between days 12-18, e.g, on day 15), (between days 26-32, e.g., on day 29), (between days 54-60, e.g., on day 57), and then about every 50-60 days thereafter, e.g., every 56 days thereafter, e.g., on days 15, 29 and 57, and then every 56 days thereafter.

In some embodiments, the subject has been administered Compound 1 less than about 30 days prior to the evaluation, e.g., less than about 29 days, e.g., less than about 28 days, e.g., less than about 27 days, e.g., less than about 26 days, e.g., less than about 25 days, less than about 24 days, e.g., less than about 23 days, e.g., less than about 22 days, e.g., less than about 21 days, e.g., less than about 20 days, e.g., less than about 19 days, e.g., less than about 18 days, e.g., less than about 17 days, e.g., less than about 16 days, e.g., less than about 15 days, e.g., less than about 14 days, e.g., about 7 days, less than about 6 days, less than about 5 days, less than about 4 days, less than about 3 days, or less than 72 hours prior to the evaluation, e.g., less than 48 hours, less than 24 hours, less than 12 hours, less than 10 hours, less than 8 hours, less than 6 hours, less than 4 hours, less than 3 hours, less than 2 hours, less than 1.5 hours, less than 1 hour, less than 45 minutes, less than 30 minutes, or less than 15 minutes, prior to the evaluation.

In some embodiments, the subject has been administered, e.g., orally, Compound 1 at a dose of about 10 mg to about 3000 mg, e.g., once or twice daily, (e.g., about every 8-16 hours, e.g., about every 12 hours), or (e.g., about every 12-36 hours, e.g., about every 24 hours), e.g., at about 10 mg to about 60 mg, at about 60 mg to about 200 mg, at about 200 mg to about 500 mg, at about 500 mg to about 1200 mg, at about 1200 mg to about 2000 mg, or at about 2000 mg to about 3000 mg, e.g., at about 50 mg, at about 100 mg, at about 300 mg, at about 500 mg, at about 800 mg once or twice daily, e.g., about every 12 hours, or e.g., about every 24 hours, prior to the evaluation.

In some embodiments, the subject has or is diagnosed as having a disorder. In some embodiments, the disorder is an advanced hematologic malignancy, e.g., an advanced hematologic malignancy characterized by the presence of a mutant allele of IDH1. In some embodiments, the advanced hematologic malignancy is characterized by a mutant allele of IDH1, wherein the IDH1 mutation results in a new ability of the enzyme to catalyze the NAPH-dependent reduction of α-ketoglutarate to R(−)-2-hydroxyglutarate (2HG) in a patient. In one embodiment, the mutant IDH1 has an R132X mutation. In one embodiment, the R132X mutation is selected from R132H, R132C, R132L, R132V, R132S and R132G. In another aspect, the R132X mutation is R132H or R132C. In one embodiment, the R132X mutation is R132H.

In some embodiments, the advanced hematologic malignancy is characterized by a co-mutation, e.g., a co-mutation selected from NPM1, FLT3, TET2, CEBPA, DNMT3A, and MLL.

In some embodiments, the disorder is selected from acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), B-acute lymphoblastic leukemias (B-ALL), and lymphoma (e.g., T-cell lymphoma), wherein each is characterized by the presence of a mutant allele of IDH1. In some embodiments, the disorder is selected from advanced IDH1 mutation-positive relapsed and/or refractory AML (R/R AML), untreated AML, and MDS.

In some embodiments, the subject has been previously treated with one or more chemotherapeutic agent(s). In some embodiments, the chemotherapeutic agent is selected from cytarabine (Ara-C), daunorubicin, etoposide, mitoxantrone, idarubicin, 5-azacytidine, decitabine, SGN33A, sargramostim, WT-1 analog peptide vaccine, tipifarnib, MK-8242, campath, and 6 Mercaptopurine (6MP).

In another aspect, the present invention provides a method of treating a disorder in a subject, the method comprising: administering to the subject in need thereof a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1), or a pharmaceutically acceptable salt thereof, in an amount sufficient to provide a reduction in blast cells, e.g., leukemic blast cells, e.g., myeloblasts or myeloid blasts, to thereby treat the disorder.

In some embodiments, the disorder is an advanced hematologic malignancy, e.g., an advanced hematologic malignancy characterized by the presence of a mutant allele of IDH1. In some embodiments, the advanced hematologic malignancy is characterized by a mutant allele of IDH1, wherein the IDH1 mutation results in a new ability of the enzyme to catalyze the NAPH-dependent reduction of α-ketoglutarate to R(−)-2-hydroxyglutarate (2HG) in a patient. In one embodiment, the mutant IDH1 has an R132X mutation. In one embodiment, the R132X mutation is selected from R132H, R132C, R132L, R132V, R132S and R132G. In another aspect, the R132X mutation is R132H or R132C. In one embodiment, the R132X mutation is R132H.

In some embodiments, the disorder is selected from acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), B-acute lymphoblastic leukemias (B-ALL), and lymphoma (e.g., T-cell lymphoma), wherein each is characterized by the presence of a mutant allele of IDH1. In some embodiments, the disorder is selected from advanced IDH1 mutation-positive relapsed and/or refractory AML (R/R AML), untreated AML, and MDS.

In some embodiments, the subject has been previously treated with one or more chemotherapeutic agent(s). In some embodiments, the chemotherapeutic agent is selected from cytarabine (Ara-C), daunorubicin, etoposide, mitoxantrone, idarubicin, 5-azacytidine, decitabine, SGN33A, sargramostim, WT-1 analog peptide vaccine, tipifarnib, MK-8242, campath, and 6 Mercaptopurine (6MP).

In some embodiments, the reduction in blast cells, e.g., leukemic blast cells, e.g., myeloblasts or myeloid blasts, is by about at least a factor of 10, e.g., relative to a reference standard, e.g., by about at least a factor of 11, e.g., by about at least a factor of 12, e.g., by about at least a factor of 13, e.g., by about at least a factor of 14, e.g., by about at least a factor of 15, e.g., by about at least a factor of 16, e.g., by about at least a factor of 17, e.g., by about at least a factor of 18, e.g., by about at least a factor of 19, e.g., by about at least a factor of 20, relative to a reference standard.

In another embodiment, the blast cells, e.g., leukemic blast cells, e.g., myeloblasts or myeloid blasts, are reduced relative to a reference standard, e.g., to a level that is less than about 10%, e.g., less than about 9%, e.g., less than about 8%, e.g., less than about 7%, e.g., less than about 6%, e.g., less than about 5%, e.g., less than about 4%, e.g., less than about 3%, e.g., less than about 2%, e.g., complete remission (CR), relative to a reference standard.

In some embodiments, the reference standard is the level of blast cells, e.g., leukemic blast cells, e.g., myeloblasts or myeloid blasts, in the subject prior to administration of Compound 1, e.g., in an untreated subject, e.g., in a subject not previously treated with Compound 1. In some embodiments, the subject has been previously treated with one or more chemotherapeutic agent(s). In some embodiments, the chemotherapeutic agent is selected from cytarabine (Ara-C), daunorubicin, etoposide, mitoxantrone, idarubicin, 5-azacytidine, decitabine, SGN33A, sargramostim, WT-1 analog peptide vaccine, tipifarnib, MK-8242, campath, and 6 Mercaptopurine (6MP).

In some embodiments, the reference standard is the total number of cells in the sample. In some embodiments, the sample comprises blast cells, myelocytes, neutrophils, promyelocytes, metamyelocytes, and monocytes.

In some embodiments, the subject is monitored for an adverse event. In some embodiments, the adverse event, includes without limitation, febrile neutropenia, dyspnea, hypotension, mental status changes, neutropenia, increase in the level of blood uric acid, bronchopulmonary aspergilliosis, dizziness, prolonged electrocardiogram QT, fatigue, intracranial hemorrhage, hypoxia, leukocytosis, leukostasis, lung infection, metabolic acidosis, nausea, organ failure, pericardial effusion, fungal pneumonia, pyrexia, renal impairment, retinoic acid syndrome, septic shock, systemic candida, tachycardia, and vertigo.

In some embodiments, the adverse event is differentiation syndrome wherein symptoms comprise fever and/or dyspnea. In some embodiments, the subject is monitored for differentiation syndrome, and if the subject experiences differentiation syndrome is treated with steroids.

In some embodiments, the subject is monitored for an adverse event, e.g., a serious adverse event (SAE), and if an adverse event, e.g., SAE, is experienced by the patient, then treatment is modified or discontinued.

Treatment methods described herein can additionally comprise various evaluation steps prior to and/or following treatment with Compound 1. In some embodiments, prior to and/or after treatment with Compound 1, the method further comprises the step of evaluating PK and PD parameters (e.g., tissue, blood, plasma and/or urine concentration(s) of Compound 1 or 2HG). This evaluation may be achieved by sample analysis of bodily tissue or bodily fluid, such as blood, plasma or urine by e.g., mass spectroscopy, e.g. LC-MS.

Also disclosed herein are solid dispersions, comprising an inhibitor of mutant IDH1, or a pharmaceutically acceptable salt thereof, and one or more polymer(s). Also disclosed herein are processes for preparing such solid dispersions. These solid dispersions have improved solubility and enhance the exposure of the therapeutically active compound relative to neat crystalline forms of the therapeutically active compound.

Also disclosed herein is the pharmaceutical use of these solid dispersions for treating advanced hematologic malignancies, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1.

Also disclosed herein are pharmaceutical compositions, comprising the solid dispersion, and at least one pharmaceutically acceptable carrier. Also disclosed herein are processes for preparing the pharmaceutical compositions.

DETAILED DESCRIPTION OF THE INVENTION

Figure 1:
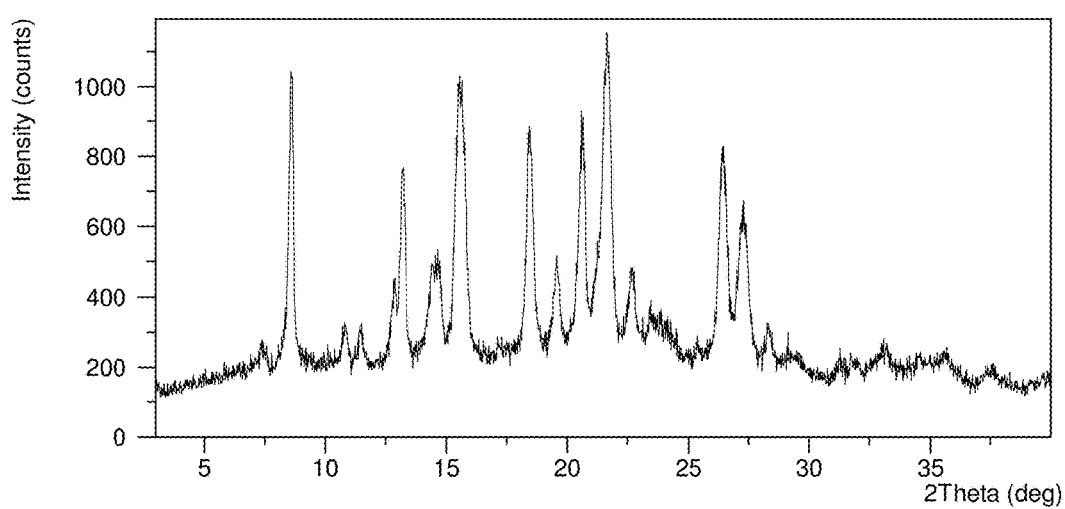
FIG. 1 is an X-ray powder diffractogram (XRPD) of Form 1.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

As used above, and throughout the description of the invention, the following terms, unless otherwise indicated, shall be understood to have the following meanings.

As used herein, the term "acquire" or "acquiring" refers to obtaining possession of a physical entity (e.g., a sample, e.g., blood sample or blood plasma sample), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood or plasma by, e.g., mass spectroscopy, e.g. LC-MS.

As used herein, "crystalline" refers to a solid having a highly regular chemical structure. In particular, a crystalline free base or salt form may be produced as one or more single crystalline forms. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of a free base or salt form is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a free base or salt form that is at least 70% crystalline. In other embodiments, substantially crystalline refers to a free base or salt form that is at least 90% crystalline.

"Form 1" or "compound 1 Form 1" may be used interchangeably, and describe the crystalline form synthesized in Example 2, in the Examples section below, and as described below, and represented by data shown in FIGS. 1, 2, and 3.

"Form 2" or "compound 1 Form 2" are used interchangeably, and describe the crystalline form synthesized in Example 3, in the Examples section below, and as described below, and represented by data shown in FIGS. 4, 5, and 6.

As used herein, "amorphous" refers to a solid material having no long range order in the position of its atoms. Amorphous solids are generally supercooled liquids in which the molecules are arranged in a random manner so that there is no well-defined arrangement and no long range order. Amorphous solids are generally isotropic, i.e., exhibit similar properties in all directions and do not have definite melting points. For example, an amorphous material is a solid material having no sharp characteristic crystalline peak(s) in its X-ray powder diffraction (XRPD) pattern (i.e., is not crystalline as determined by XRPD). Instead, one or several broad peaks (e.g., halos) appear in its XRPD pattern. Broad peaks are characteristic of an amorphous solid. An amorphous preparation of a compound described herein is substantially free of impurities and/or crystalline compound.

The term "substantially free" refers to forms and compositions that may be at least a particular weight percent free of impurities and/or crystalline compound. Particular weight percentages are 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 60% and 100% free of impurities and/or crystalline compound. In some embodiments, substantially free refers to a free base or salt form that is at least 70% pure. In other embodiments, substantially crystalline refers to a free base or salt form that is at least 90% pure. In other embodiments, substantially free of crystalline compound refers to a composition having less than about 30%, less than about 20%, less than about 15%, less than about 10%, less than about 5%, less than about 1% of crystalline compound.

As used herein, the terms "isolated" refers to forms that may be at least a particular weight percent of a particular crystalline form of a compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "elevated levels of 2HG" means 10%, 20% 30%, 50%, 75%, 100%, 200%, 500% or more 2HG than is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (i.e., an advanced solid tumor, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1), lessen the severity of the disease/disorder (i.e., an advanced solid tumor, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1) or improve the symptoms associated with the disease/disorder (i.e., an advanced solid tumor, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1.

As used herein, an amount of a compound effective to treat a disorder, or a "therapeutically effective amount" refers to an amount of the compound, which is effective, upon single or multiple dose administration to a subject, in treating a cell, or in curing, alleviating, relieving or improving a subject with a disorder beyond that expected in the absence of such treatment.

As used herein, "% w/w" is used to mean by weight as a percentage of a total weight that is used as the basis for calculating the weight percentage of an individual component. By way of example, for a bulk composition, the % w/w of an individual component may be calculated as a percentage of the total weight of all of the components of the bulk composition. By way of another example, for a single oral dosage form, the % w/w of an individual component may be calculated as a percentage of the total weight of all of the components of the single oral dosage form. For example, when the single oral dosage form is a tablet, the total weight may be the total weight of all the components of the tablet.

As used herein, the term "subject" is intended to mean human. Exemplary human subjects include a human patient (referred to as a patient) having a disorder, e.g., a disorder described herein or a normal subject.

The term "physically stable," as used herein, means that a particular free base or salt form does not change into one or more different physical forms (e.g., different solid forms as measured by XRPD, DSC, etc.) when subjected to specified conditions, e.g., room temperature ambient humidity or 40° C./75% relative humidity, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of a compound changes into one or more different physical forms when subjected to specified conditions. In some embodiments, less than about 20%, less than about 15%, less than about 10%, less than about 5%, less than about 3%, less than about 1%, less than about 0.5% of the form of a particular compound changes into one or more different physical forms of that particular compound when subjected to specified conditions. In some embodiments, no detectable amount of the particular form of a compound changes into one or more different physical forms of the compound.

The term "chemically stable," as used herein, means that the chemical structure of a particular compound, does not change into another compound (e.g., decompose) when subjected to specified conditions, e.g., room temperature ambient humidity or 40° C./75% relative humidity, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of a particular compound changes into one or more other compounds when subjected to specified conditions. In some embodiments, less than about 20%, less than about 15%, less than about 10%, less than about 5%, less than about 3%, less than about 1%, less than about 0.5% of the form of a particular compound changes into one or more other compounds when subjected to specified conditions. In some embodiments, no detectable amount of the form of a particular compound changes into one or more different physical forms of that particular compound.

The term "dispersion" refers to a disperse system in which one substance, the dispersed phase, is distributed, in discrete units, throughout a second substance (the continuous phase or vehicle). The size of the dispersed phase can vary considerably (e.g., colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline therapeutically active compound (dispersed phase) in an amorphous polymer(s) (continuous phase), or alternatively, an amorphous therapeutically active compound (dispersed phase) in an amorphous polymer (continuous phase).

The term "amorphous solid dispersion" generally refers to a solid dispersion of two or more components, usually a therapeutically active compound and polymer (or plurality of polymers), but possibly containing other components such as surfactants or other pharmaceutical excipients, where the therapeutically active compound is in the amorphous phase, and the physical stability and/or dissolution and/or solubility of the amorphous therapeutically active compound is enhanced by the other components. In some embodiments, an amorphous solid dispersion includes the polymer(s) (and optionally a surfactant) constituting the dispersed phase, and the therapeutically active compound constitutes the continuous phase. In some embodiments, an amorphous solid dispersion includes the polymer(s) (and optionally a surfactant) constituting the continuous phase, and the therapeutically active compound constitutes the dispersed phase.

An exemplary solid dispersion is a co-precipitate or a co-melt of a particular therapeutically active compound with one or more polymer(s). A "co-precipitate" is produced after dissolving a therapeutically active compound and one or more polymer(s) in a solvent or solvent mixture followed by the removal of the solvent or solvent mixture. Sometimes the one or more polymer(s) can be suspended in the solvent or solvent mixture. The solvent or solvent mixture includes organic solvents and supercritical fluids. The solvent or solvent mixture can also contain a non-volatile solvent. A "co-melt" is produced after heating a therapeutically active compound and one or more polymer(s) to melt, optionally in the presence of a solvent or solvent mixture, followed by mixing, removal of at least a portion of the solvent if applicable, and cooling to room temperature at a selected rate. In some cases, solid dispersions are prepared by adding a solution of a therapeutically active compound and solid polymers followed by mixing and removal of the solvent or solvent mixture. To remove the solvent or solvent mixture, vacuum drying, spray drying, tray drying, lyophilization, and other drying procedures may be applied. Applying any of these methods using appropriate processing parameters, according to this disclosure, would provide the particular therapeutically active compound in an amorphous state in the final solid dispersion product.

As used herein, the term "directly compressed dosage form" generally refers to a form (e.g., a tablet) that is obtained by the compression of a dry blend of powders (e.g., solid dispersion, e.g., agglomerated dispersion) that comprise a compound, e.g., a therapeutic compound (e.g., a poorly soluble therapeutic compound, e.g., compound 1, e.g., amorphous compound 1, e.g., in a solid dispersion, e.g., that also includes one or more polymer(s) and optionally one or more surfactant(s)) and optionally one or more excipients. For example, the product (e.g., solid dispersion) resulting from a process described herein can have improved properties (e.g., flowability) that allow it to be directly compressed, e.g., into an oral dosage form, e.g., tablets, or to be formulated into capsules or saches.

Pharmaceutical Compositions and Methods of Treatment

Provided is a method of treating advanced solid tumors, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 comprising administering to a subject in need thereof a pharmaceutical composition comprising: (a) a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1), or a pharmaceutically acceptable salt thereof, as part of a solid dispersion, and optionally (b) one or more pharmaceutically acceptable carrier(s).

Also provided are compositions containing Compound 1, or a pharmaceutically acceptable salt thereof, as part of a solid dispersion (e.g., an amorphous solid dispersion). Also provided are pharmaceutical compositions, comprising: (a) Compound 1, or a pharmaceutically acceptable salt thereof, as part of a solid dispersion, and (b) one or more pharmaceutically acceptable carrier(s).

These methods of treatment and pharmaceutical compositions are further illustrated by the detailed descriptions and illustrative examples given below.

Pharmaceutical compositions comprising solid dispersions of a therapeutically active compound in a matrix can provide improved chemical and physical properties and can be prepared by forming a homogeneous solution or melt of the therapeutically active compound and matrix material followed by solidifying the mixture by cooling, or removal of the solvent. Such solid dispersions of therapeutically active compounds often show enhanced bioavailability when administered orally relative to oral compositions comprising the undispersed compound.

Spray drying is the most widely used industrial process involving particle formation and drying, and can be used to produce solid dispersions of therapeutically active compounds. It is highly suited for the continuous production of dry solids in either powder, granulate or agglomerate form from liquid feedstocks as solutions, emulsions and pumpable suspensions. Therefore, spray drying is a useful process where the end-product must comply with precise quality standards regarding particle size distribution, residual moisture content, bulk density, and particle shape.

Critical quality attributes of a spray-dried dispersion include potency, related substances, residual solvent content, homogeneity, lack of crystallinity, dissolution performance, particle morphology, and bulk powder flow properties.

Critical process parameters include spray solution composition and viscosity, nozzle type and dimensions, atomization pressure, spray solution feed rate, drying gas flow rate, inlet and outlet temperatures, condenser temperature (e.g., for closed-loop drying processes), and secondary drying parameters.

In one embodiment, at least a particular percentage by weight of Compound 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of Compound 1 is crystalline, the remainder of Compound 1 is the amorphous form of Compound 1. Non-limiting examples of crystalline Compound 1 include a single crystalline form of Compound 1 or a mixture of different single crystalline forms. In some embodiments, Compound 1 is at least 90% by weight crystalline. In some other embodiments, Compound 1 is at least 95% by weight crystalline. In some other embodiments, Compound 1 is at least 99% by weight crystalline.

In another embodiment, a particular percentage by weight of the crystalline Compound 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, Compound 1 is at least 90% by weight of a single crystalline form. In another embodiment, Compound 1 is at least 95% by weight of a single crystalline form. In another embodiment, Compound 1 is at least 99% by weight of a single crystalline form.

In the following description of Compound 1, embodiments of the invention may be described with reference to a particular crystalline form of Compound 1, as characterized by one or more properties as discussed herein. The descriptions characterizing the crystalline forms may also be used to describe the mixture of different crystalline forms that may be present in a crystalline Compound 1. However, the particular crystalline forms of Compound 1 may also be characterized by one or more of the characteristics of the crystalline form as disclosed herein, with or without regard to referencing a particular crystalline form.

The crystalline forms are further illustrated by the detailed descriptions and illustrative examples given below. The XRPD peaks described in Tables 1 and 2 may vary by ±0.2 depending upon the instrument used to obtain the data.

Form 1

In one embodiment, a single crystalline form, Form 1, of the compound 1 is characterized by the X-ray powder diffraction (XRPD) pattern shown in FIG. 1, and data shown in Table 1, obtained using CuKa radiation. In a particular embodiment, the polymorph can be characterized by one or more of the peaks taken from FIG. 1, as shown in Table 1. For example, the polymorph can be characterized by one or two or three or four or five or six or seven or eight or nine of the peaks shown in Table 1.

TABLE 1

| Angle 2-Theta° | Intensity % |
| --- | --- |
| 8.6 | 90.3 |
| 13.2 | 60.0 |
| 15.6 | 85.5 |
| 18.5 | 72.5 |
| 19.6 | 31.5 |
| 20.6 | 71.6 |
| 21.6 | 100.0 |
| 26.4 | 64.2 |
| 27.3 | 45.6 |

In another embodiment, Form 1 can be characterized by the peaks identified at 2θ angles of 8.6, 15.6, 18.5, 20.6, 21.6, and 26.4°. In another embodiment, Form 1 can be characterized by the peaks identified at 2θ angles of 8.6, 15.6, 18.5, and 21.6°.

Figure 2:
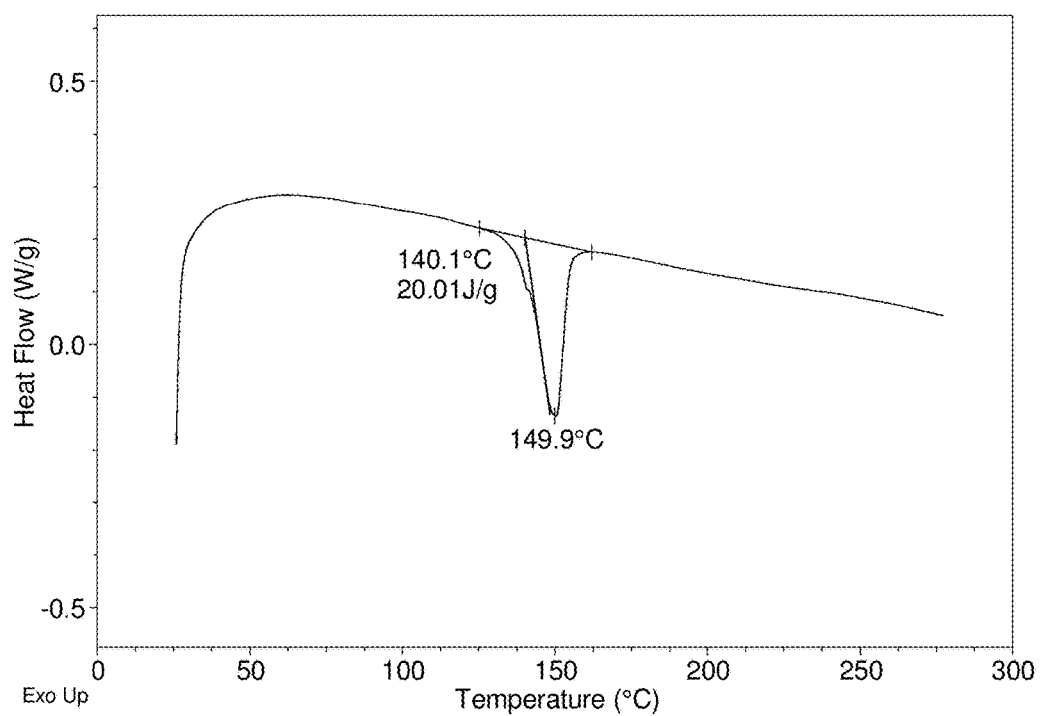
FIG. 2 is a differential scanning calorimetry (DSC) profile of Form 1.

In another embodiment, Form 1 can be characterized by the differential scanning calorimetry profile (DSC) shown in FIG. 2. The DSC graph plots the heat flow as a function of temperature from a sample, the temperature rate change being about 10° C./min. The profile is characterized by an endothermic transition with an onset temperature of about 140.1° C. with a melt at about 149.9° C.

Figure 3:
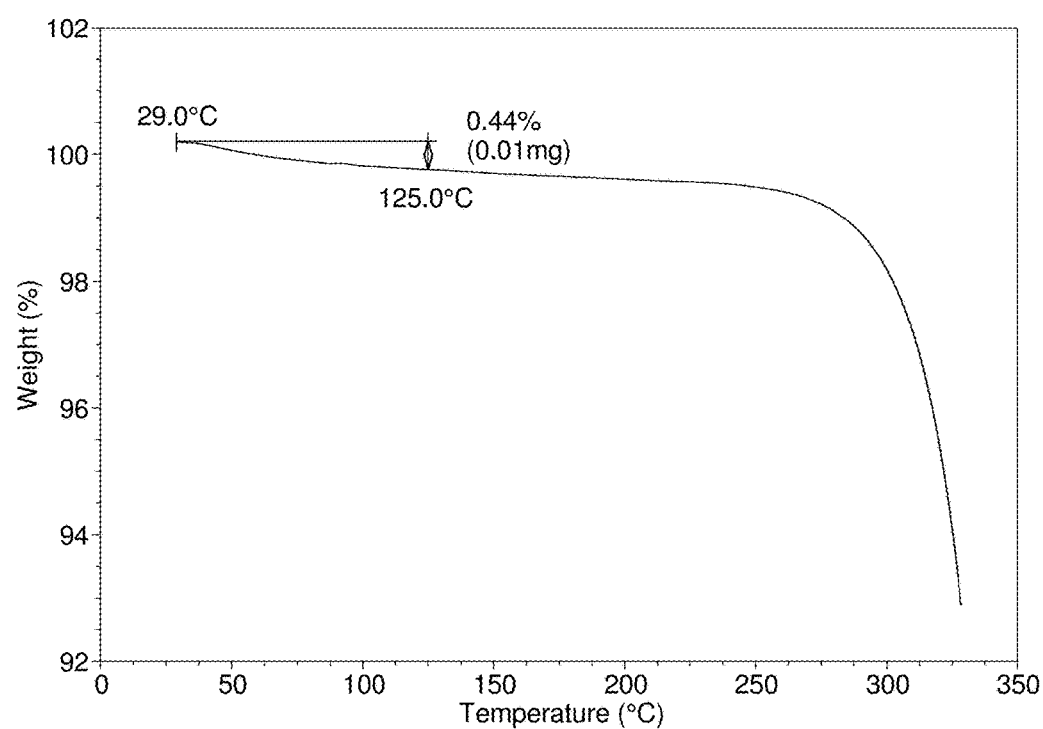
FIG. 3 is a thermal gravimetric analysis (TGA) profile of Form 1.

In another embodiment, Form 1 can be characterized by thermal gravimetric analysis (TGA) shown in FIG. 3. The TGA profile graphs the percent loss of weight of the sample as a function of temperature, the temperature rate change being about 10° C./min. The weight loss represents a loss of about 0.44% of the weight of the sample as the temperature is changed from about 29.0° C. to 125.0° C.

Form 2

Figure 4:
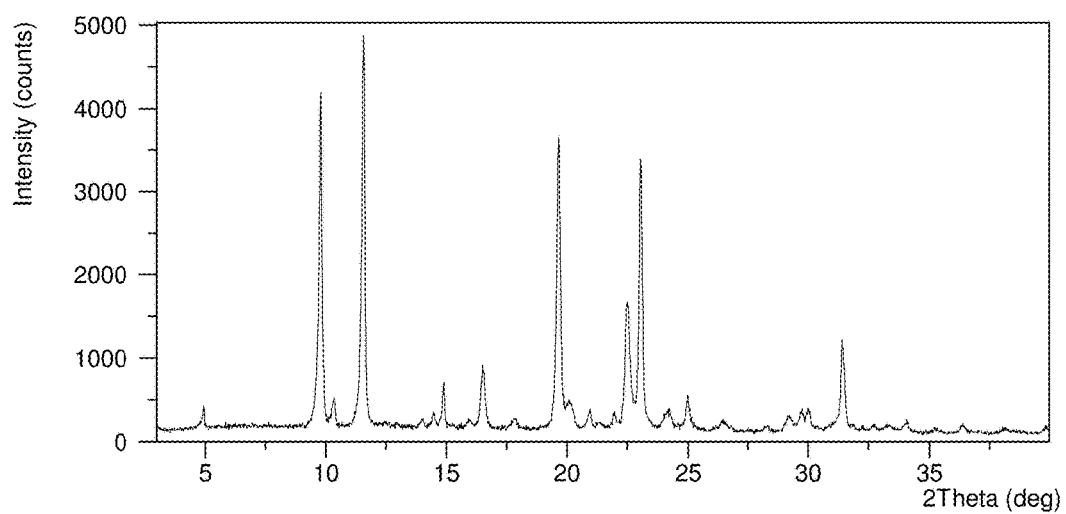
FIG. 4 is an X-ray powder diffractogram (XRPD) of Form 2.

In one embodiment, a single crystalline form, Form 2, of the compound 1 is characterized by the X-ray powder diffraction (XRPD) pattern shown in FIG. 4, and data shown in Table 2, obtained using CuKa radiation. In a particular embodiment, the polymorph can be characterized by one or more of the peaks taken from FIG. 4, as shown in Table 2. For example, the polymorph can be characterized by one or two or three or four or five or six or seven or eight or nine or ten of the peaks shown in Table 2.

TABLE 2

| Angle 2-Theta° | Intensity % |
| --- | --- |
| 9.8 | 85.6 |
| 11.6 | 100.0 |
| 14.9 | 11.4 |
| 16.5 | 15.3 |
| 19.6 | 75.2 |
| 20.1 | 7.3 |
| 22.5 | 32.6 |
| 23.0 | 69.4 |
| 25.0 | 8.9 |
| 31.4 | 22.0 |

In another embodiment, Form 2 can be characterized by the peaks identified at 2θ angles of 9.8, 11.6, 19.6, 22.5, 23.0, and 31.4°. In another embodiment, Form 2 can be characterized by the peaks identified at 2θ angles of 9.8, 11.6, 19.6, and 23.0°.

Figure 5:
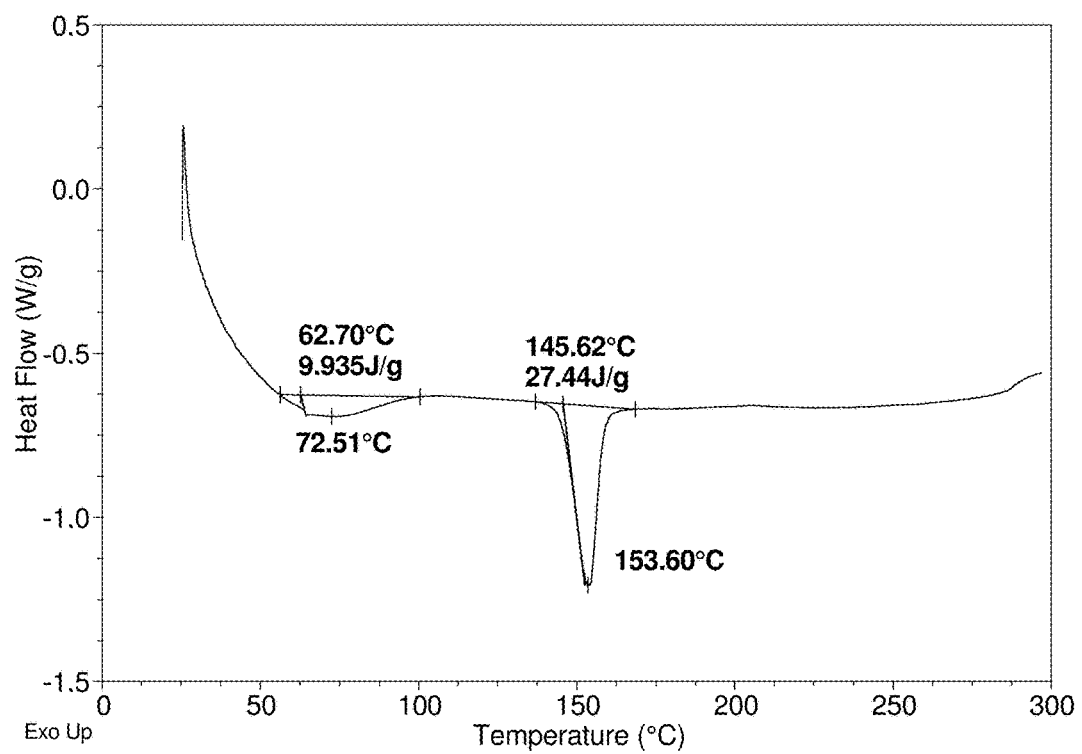
FIG. 5 is a differential scanning calorimetry (DSC) profile of Form 2.

In another embodiment, Form 2 can be characterized by the differential scanning calorimetry profile (DSC) shown in FIG. 5. The DSC graph plots the heat flow as a function of temperature from a sample, the temperature rate change being about 10° C./min. The profile is characterized by an endothermic transition with an onset temperature of about 62.7° C. with a melt at about 72.5° C., and an endothermic transition with an onset temperature of about 145.6° C. with a melt at about 153.6° C.

Figure 6:
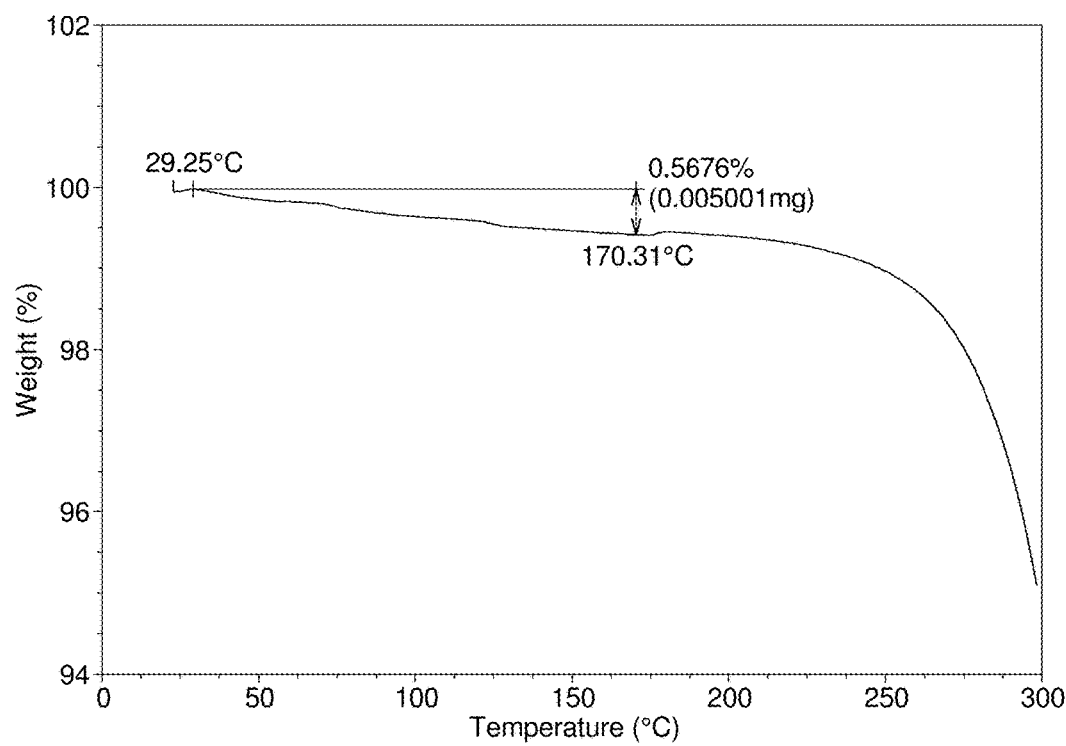
FIG. 6 is a thermal gravimetric analysis (TGA) profile of Form 2.

In another embodiment, Form 2 can be characterized by thermal gravimetric analysis (TGA) shown in FIG. 6. The TGA profile graphs the percent loss of weight of the sample as a function of temperature, the temperature rate change being about 10° C./min. The weight loss represents a loss of about 0.57% of the weight of the sample as the temperature is changed from about 29.3° C. to 170.3° C.

Other embodiments are directed to a single crystalline form of compound 1 characterized by a combination of the aforementioned characteristics of any of the single crystalline forms discussed herein. The characterization may be by any combination of one or more of the XRPD, TGA, and DSC described for a particular polymorph. For example, the single crystalline form of compound 1 may be characterized by any combination of the XRPD results regarding the position of the major peaks in a XRPD scan; and/or any combination of one or more of parameters derived from data obtained from a XRPD scan. The single crystalline form of compound 1 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of Compound 1 as determined by water sorption/desorption measurements over a range of relative humidity (e.g., 0% to 90%) may also characterize a single crystalline form of Compound 1.

Solid Dispersions

Provided are compositions, comprising Compound 1, or a pharmaceutically acceptable salt thereof, and one or more polymer(s) as part of a solid dispersion (e.g., an amorphous solid dispersion). In some embodiments, the solid dispersion comprises Compound 1, or a pharmaceutically acceptable salt thereof, and one or more polymer(s). In some embodiments, the solid dispersion comprises Compound 1, or a pharmaceutically acceptable salt thereof, one or more polymer(s), and one or more surfactant(s). In some embodiments, the solid dispersion comprises Compound 1, or a pharmaceutically acceptable salt thereof, and one polymer. In some embodiments, the solid dispersion comprises Compound 1, or a pharmaceutically acceptable salt thereof, one polymer, and a surfactant.

The solid dispersions provided herein, comprising Compound 1, or a pharmaceutically acceptable salt thereof, can enhance the solubility of Compound 1 relative to a neat crystalline form of Compound 1 (e.g., Form 1 or Form 2), and thus provide improved exposure upon oral dosing of the solid dispersion to a subject. In one embodiment, the solid dispersion comprises Compound 1, or a pharmaceutically acceptable salt thereof, one or more polymer(s), and optionally one or more solubility enhancing surfactant.

For example, the aqueous solubility of Form 1 is about 0.025 mg/mL to about 0.035 mg/mL and the aqueous solubility of Form 2 is about 0.008 mg/mL to about 0.010 mg/mL.

Form 2 has a solubility of about 0.018 mg/mL in fasted state simulated intestinal fluid (FASSIF) at a pH of 6.1 at 4 hours. In comparison, amorphous spray-dried dispersions have a solubility of about 0.05 mg/mL to about 0.50 mg/mL in FASSIF at 3 hours.

In some embodiments, the solid dispersion exhibits at least about 20%, at least about 30%, at least about 40%, at least about 50%, at least about 60%, at least about 70%, at least about 80%, or at least about 90% higher exposure of Compound 1, or a pharmaceutically acceptable salt thereof, when administered to a subject as compared to administration of in-situ amorphous Compound 1, or a pharmaceutically acceptable salt thereof. In some embodiments, the solid dispersion exhibits at least about 20%, at least about 30%, at least about 40%, at least about 50%, at least about 60%, at least about 70%, at least about 80%, or at least about 90% higher exposure of Compound 1, or a pharmaceutically acceptable salt thereof, when administered to a subject as compared to administration of neat crystalline Compound 1, or a pharmaceutically acceptable salt thereof.

In rat and monkey pharmacokinetics studies, modest exposure improvement is observed upon administration of solid dispersion oral dosage forms as compared to in-situ amorphous dosing shows. For example, a solid dispersion containing 50% w/w Compound 1 and 50% w/w Polyvinyl Acetate Phthalate (PVAP) has approximately two-fold higher exposure as compared to in-situ amorphous Compound 1 in male Sprague Dawley rats. There is no significant difference in exposure between a solid dispersion containing 70% w/w Compound 1 and 30% w/w oral dosage form as compared to in-situ amorphous Compound 1. In male cynomolgus monkeys, the exposure of a solid dispersion containing 50% w/w Compound 1 and 50% w/w hydroxypropylmethylcellulose acetate succinate, also known as hpromellose acetate succinate, (HPMCAS) shows no significant difference as compared to the in-situ amorphous Compound 1. Similarly, a solid dispersion containing 50% w/w Compound 1 and 50% w/w hydroxypropylmethylcellulose also known as hypromellose phthalate (HPMC-Phthalate) shows no significant difference as compared to the in-situ amorphous Compound 1. While in-situ amorphous therapeutic compounds are commonly used for dosing in animal studies, they are not suitable dosage forms for dosing in humans.

As described in the rat pharmacokinetics study of Example 4, Compound 1 exposure is improved when solid dispersion dosage forms are administered as compared to neat crystalline Compound 1 Form 2.

In some embodiments, at least a portion of Compound 1, or a pharmaceutically acceptable salt thereof, in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In other embodiments, the solid dispersion is substantially free of crystalline Compound 1, or a pharmaceutically acceptable salt thereof.

In some embodiments, the composition is an amorphous solid (e.g. spray dried) dispersion comprising Compound 1, or a pharmaceutically acceptable salt thereof, and a polymer. The amorphous solid dispersion can include, e.g., less than about 30%, less than about 20%, less than about 15%, less than about 10%, less than about 5%, less than about 4%, less than about 3%, less than about 2%, or less than about 1% of crystalline Compound 1, or a pharmaceutically acceptable salt thereof, e.g., be substantially free of crystalline Compound 1, or a pharmaceutically acceptable salt thereof.

In one embodiment, the solid dispersion exhibits a predetermined level of physical and/or chemical stability. E.g., the solid dispersion retains about 50%, about 60%, about 70%, about 80%, about 90%, about 95%, about 98%, or about 99%, of amorphous Compound 1, or a pharmaceutically acceptable salt thereof, when stored at 25° C. in a closed water tight container, e.g., an amber glass vial, high density polyethylene (HDPE) container or double polyethylene bags with twisted nylon tie placed in an HDPE container with desiccant.

In some embodiments, the polymer increases the chemical or physical stability (e.g., as measured by a Modulated Differential Scanning calorimeter) of Compound 1, or a pharmaceutically acceptable salt thereof, when stored (e.g., at 2-8° C., e.g. 4° C. or at room temperature) by at least about 10% (e.g., by at least about 20%, by at least about 30%, by at least about 40%, by at least about 50%, by at least about 60%, by at least about 70%, by at least about 80%, or by at least about 90%) compared to amorphous Compound 1, or a pharmaceutically acceptable salt thereof, without being in the presence of the polymer.

A solid dispersion generally exhibits a glass transition temperature, where the dispersion makes a transition from a glassy solid to a rubbery composition. In general, the higher the glass transition temperature, the greater the physical stability of the dispersion. The existence of a glass transition temperature generally indicates that at least a large portion of the composition (e.g., dispersion) is in an amorphous state. The glass transition temperature (Tg) of a solid dispersion suitable for pharmaceutical applications is generally at least about 50° C. In some embodiments, higher temperatures are preferred. Therefore, in some embodiments, a solid dispersion disclosed herein has a Tg of at least about 100° C. (e.g., at least about 100° C., at least about 105° C., at least about 110° C., at least about 115° C., at least about 120° C., at least about 125° C., at least about 130° C., at least about 135° C., at least about 140° C., at least about 150° C., at least about 160° C., at least about 170° C., at least about 175° C., at least about 180° C., or at least about 190° C.). In some embodiments, the Tg is up to about 200° C. In some embodiments, the Tg is up to about 130° C. (e.g., at least about 110° C., at least about 111° C., at least about 112° C., at least about 113° C., at least about 114° C., at least about 115° C., at least about 116° C., at least about 117° C., at least about 118° C., at least about 119° C., at least about 120° C., at least about 121° C., at least about 122° C., at least about 123° C., at least about 124° C., at least about 125° C., at least about 1216° C., at least about 127° C., at least about 128° C., at least about 129° C., or at least about 130° C.). Unless otherwise noted, the glass transition temperatures disclosed herein are measured under dry conditions.

In some embodiments the solid dispersion has a higher glass transition temperature than the glass transition temperature of amorphous Compound 1, or a pharmaceutically acceptable salt thereof, without being in the presence of the polymer(s). In some embodiments, the solid dispersion has a relaxation rate that is lower than the relaxation rate of amorphous Compound 1, or a pharmaceutically acceptable salt thereof, without being in the presence of the polymer(s).

Examples of polymers in the solid dispersion include cellulose derivatives (e.g., hydroxypropylmethylcellulose also known as hypromellose, (HPMC), hydroxypropylmethylcellulose phthalate, also known as hypromellose phthalate (HPMCP), hydroxypropylmethylcellulose acetate succinate, also known as hpromellose acetate succinate, (HPMCAS), hydroxypropylcellulose (HPC)), ethylcellulose, or cellulose acetate phthalate; polyvinylpyrrolidones (PVP); polyethylene glycols (PEG); polyvinyl alcohols (PVA); polyvinyl esters, such as Polyvinyl Acetate Phthalate (PVAP); acrylates, such as polymethacrylate (e.g., Eudragit® E); cyclodextrins (e.g., .beta.-cyclodextrin); Poly (D, L-lactide) (PLA), Poly (D,L-lactide, co-glycolide acid (PLGA); and copolymers and derivatives thereof, including for example polyvinylpyrollidone-vinyl acetate (PVP-VA), Polyvinyl caprolactam-polyvinyl, and acetate-polyethyleneglycol copolymer, Methylacrylate/methacrylic acid copolymer; Soluplus; Copovidone; and mixtures thereof.

In some embodiments, the solid dispersion includes one water-soluble polymer. In some embodiments, the solid dispersion includes one partially water-soluble polymer. In some embodiments, the polymer is a cellulose polymer.

In some embodiments, the polymer is HPMCAS (e.g., HPMCAS of different grades: HPMCAS-M, HPMCAS-MG or HPMCAS-HG). In some embodiments, the polymer is PVAP. In some embodiments, the polymer is HPMC (e.g., HPMC of different grades: HMPC60SH50, HPMCE50 or HPMCE15). In some embodiments, the polymer is HPMCP (e.g., HPMCP of different grades: e.g., HMPCP-HP55).

In some embodiments, the polymer is a pH-dependent enteric polymer. Such pH-dependent enteric polymers include, but are not limited to, cellulose derivatives (e.g., cellulose acetate phthalate (CAP)), HPMCP, HPMCAS, carboxymethylcellulose (CMC) or a salt thereof (e.g., a sodium salt such as (CMC-Na)); cellulose acetate trimellitate (CAT), hydroxypropylcellulose acetate phthalate (HP-CAP), hydroxypropylmethyl-cellulose acetate phthalate (HPMCAP), and methylcellulose acetate phthalate (MCAP), polymethacrylates (e.g., Eudragit S), or mixtures thereof.

In some embodiments, the polymer is hydroxypropylmethylcellulose acetate succinate, also known as hypromellose acetate succinate, (HPMCAS), e.g., HMPCAS-HG.

In another embodiment, the polymer(s) is an insoluble cross-linked polymer, for example a polyvinylpyrrolidone (e.g., Crospovidone). In another embodiment, the polymer(s) is polyvinylpyrrolidone (PVP).

In some embodiments, the one or more polymer(s) is present in the solid dispersion in an amount of between about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, the polymer(s) is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, the polymer(s) is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, the polymer(s) is present in the solid dispersion in an amount of from about 30% w/w to about 70% w/w. In some embodiments, the polymer(s) is present in the solid dispersion in an amount of from about 35% w/w to about 65% w/w. In some embodiments, the polymer(s) is present in the solid dispersion in an amount of from about 40% w/w to about 60% w/w. In some embodiments, the polymer(s) is present in the solid dispersion in an amount of from about 45% w/w to about 55% w/w. In some embodiments, the polymer(s) is present in the solid dispersion in an amount of about 50% w/w.

In some embodiments, Compound 1, or a pharmaceutically acceptable salt thereof, is present in the solid dispersion in an amount of from about 10% w/w and 90% w/w (e.g., between about 20% w/w and about 80% w/w; between about 30% w/w and about 70% w/w; between about 40% w/w and about 60% w/w; or between about 15% w/w and about 35% w/w). In some embodiments, Compound 1, or a pharmaceutically acceptable salt thereof, is present in the solid dispersion in an amount of from about 10% w/w to about 80% w/w, for example from about 30% w/w to about 75% w/w, or from about 40% w/w to about 65% w/w, or from about 45% w/w to about 55% w/w, for example, about 46% w/w, about 47% w/w, about 48% w/w, about 49% w/w, about 50% w/w, about 51% w/w, about 52% w/w, about 53% w/w, or about 54% w/w. In some embodiments, Compound 1, or a pharmaceutically acceptable salt thereof, is present in the solid dispersion in an amount of about 48% w/w, about 48.5% w/w, about 49% w/w, about 49.5% w/w, about 50% w/w, about 50.5% w/w, about 51% w/w, about 51.5% w/w, about 52% w/w, or about 52.5% w/w.

In some embodiments, Compound 1, or a pharmaceutically acceptable salt thereof, is present in the solid dispersion in an amount of from about 30% w/w to about 70% w/w. In some embodiments, Compound 1, or a pharmaceutically acceptable salt thereof, is present in the solid dispersion in an amount of from about 35% w/w to about 65% w/w. In some embodiments, Compound 1, or a pharmaceutically acceptable salt thereof, is present in the solid dispersion in an amount of from about 40% w/w to about 60% w/w. In some embodiments, Compound 1, or a pharmaceutically acceptable salt thereof, is present in the solid dispersion in an amount of from about 45% w/w to about 55% w/w. In some embodiments, Compound 1, or a pharmaceutically acceptable salt thereof, is present in the solid dispersion in an amount of about 50% w/w.

In another embodiment, the solid dispersion includes about 20% w/w to about 80% w/w Compound 1, or a pharmaceutically acceptable salt thereof, and about 20% w/w to about 80% of polymer(s). In another embodiment, the solid dispersion includes about 25% w/w to about 75% w/w Compound 1, or a pharmaceutically acceptable salt thereof, and about 25% w/w to about 75% of polymer(s). In another embodiment, the solid dispersion includes about 30% w/w to about 70% w/w Compound 1, or a pharmaceutically acceptable salt thereof, and about 30% w/w to about 70% of polymer(s). In another embodiment, the solid dispersion includes about 35% w/w to about 65% w/w Compound 1, or a pharmaceutically acceptable salt thereof, and about 35% w/w to about 65% of polymer(s). In another embodiment, the solid dispersion includes about 40% w/w to about 60% w/w Compound 1, or a pharmaceutically acceptable salt thereof, and about 40% w/w to about 60% of polymer(s). In another embodiment, the solid dispersion includes about 45% w/w to about 55% w/w Compound 1, or a pharmaceutically acceptable salt thereof, and about 45% w/w to about 55% of polymer(s). In another embodiment, the solid dispersion includes about 50% w/w Compound 1, or a pharmaceutically acceptable salt thereof, and about 50% w/w of polymer(s).

In another embodiment, the solid dispersion includes about 45% w/w to about 55% w/w Compound 1, or a pharmaceutically acceptable salt thereof, and about 45% w/w to about 55% w/w HPMCAS (e.g., HPMCAS-MG or HPMCAS-HG, or other grades such as LF, MF, HF, or LG) or PVAP. In another embodiment, the solid dispersion includes about 50% w/w Compound 1, or a pharmaceutically acceptable salt thereof, and about 50% w/w of HPMCAS.

In some embodiments, the solid dispersion also includes a surfactant or inert pharmaceutically acceptable substance. Examples of surfactants in the solid dispersion include sodium lauryl sulfate (SLS), vitamin E or a derivative thereof (e.g., vitamin E TPGS), Docusate Sodium, sodium dodecyl sulfate, polysorbates (such as Tween 20 and Tween 80), poloxamers (such as Poloxamer 335 and Poloxamer 407), glyceryl monooleate, Span 65, Span 25, Capryol 90, pluronic copolymers (e.g., Pluronic F108, Pluronic P-123), and mixtures thereof. In some embodiments, the surfactant is SLS. In some embodiments, the surfactant is vitamin E or a derivative thereof (e.g., vitamin E TPGS).

In some embodiments, the surfactant is present in the solid dispersion in an amount of from about 0.1% w/w to about 10% w/w, for example from about 0.5% w/w to about 2% w/w, or from about 1% w/w to about 3% w/w, from about 1% w/w to about 4% w/w, or from about 1% w/w to about 5% w/w. In some embodiments, the surfactant is present in the solid dispersion in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, or about 1% w/w. In some embodiments, the surfactant is present in the solid dispersion in an amount of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w.

Processes for Preparing Solid Dispersions

In some embodiments, the solid dispersion may be prepared according to a process described herein. In general, methods that could be used include those that involve rapid removal of solvent or solvent mixture from a mixture or cooling a molten sample. Such methods include, but are not limited to, rotational evaporation, freeze-drying (i.e., lyophilization), vacuum drying, melt congealing, and melt extrusion. One embodiment of this disclosure involves solid dispersion obtained by spray-drying. In one embodiment, the product obtained by spray drying is dried to remove the solvent or solvent mixture.

Preparations disclosed herein, e.g., a pharmaceutical composition, can be obtained by spray-drying a mixture comprising Compound 1, or a pharmaceutically acceptable salt thereof, one or more polymer(s), and an appropriate solvent or solvent mixture. Spray drying involves atomization of a liquid mixture containing, e.g., a solid and a solvent or solvent mixture, and removal of the solvent or solvent mixture. The solvent or solvent mixture can also contain a nonvolatile solvent, such as glacial acetic acid. Atomization may be done, for example, through a two-fluid or pressure or electrosonic nozzle or on a rotating disk.

Spray drying converts a liquid feed to a dried particulate form. Spray drying generally involves the atomization of a liquid feed solution into a spray of droplets and contacting the droplets with hot air or gas in a drying chamber. The sprays are generally produced by either rotary (wheel) or nozzle atomizers. Evaporation of moisture from the droplets and formation of dry particles proceed under controlled temperature and airflow conditions.

Optionally, a secondary drying process such as fluidized bed drying or vacuum drying, may be used to reduce residual solvents (and other additives, such as glacial acetic acid) to pharmaceutically acceptable levels. Typically, spray-drying involves contacting a highly dispersed liquid suspension or solution (e.g., atomized solution), and a sufficient volume of hot air or gas (e.g., nitrogen, e.g., pure nitrogen) to produce evaporation and drying of the liquid droplets. The preparation to be spray dried can be any solution, coarse suspension, slurry, colloidal dispersion, or paste that may be atomized using the selected spray-drying apparatus. In a standard procedure, the preparation is sprayed into a current of warm filtered air (or into gas, e.g., nitrogen) that evaporates the solvent and conveys the dried product to a collector (e.g., a cyclone). The spent air or gas is then exhausted with the solvent (or solvent mixture including any additives such as glacial acetic acid), (e.g., then filtered) or alternatively the spent air or gas is sent to a condenser to capture and potentially recycle the solvent or solvent mixture. For example, if a gas (e.g., nitrogen) is used, the gas is then optionally recycled, heated again and returned to the unit in a closed loop system. Commercially available types of apparatus may be used to conduct the spray-drying. For example, commercial spray dryers are manufactured by Buchi Ltd. and Niro (e.g., the PSD line of spray driers manufactured by Niro).

Spray-drying typically employs solids loads of material from about 1% to about 30% or up to about 50% (i.e., therapeutically active Compound plus and excipients), preferably at least about 10%. In some embodiments, solids loads of less than 10% may result in poor yields and unacceptably long run-times. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds., McGraw-Hill Book Co. (1984); and Marshall "Atomization and Spray-Drying" 50, Chem. Eng. Prog. Monogr. Series 2 (1954). In general, the spray-drying is conducted with an inlet temperature of from about 40° C. to about 200° C., for example, from about 70° C. to about 150° C., preferably from about 40° C. to about 60° C., about 50° C. to about 55° C., or about 80° C. to about 110° C., e.g., about 90° C. The spray-drying is generally conducted with an outlet temperature of from about 20° C. to about 100° C., for example from about 25° C. to about 30° C. (e.g., about 26° C.), about 40° C. to about 50° C., about 50° C. to about 65° C., e.g., about 56° C. to about 58° C.

Removal of the solvent or solvent mixture may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the spray-drying is fluidized spray drying (FSD). The steps in FSD can include, for example: preparing a liquid feed solution (e.g., containing Compound 1 or a pharmaceutically acceptable salt thereof, and optionally a polymer(s) and/or surfactant(s), dissolved or suspended in solvent(s)); atomizing (e.g., with a pressure nozzle, a rotary atomizer or disk, two-fluid nozzle or other atomizing methods) the feed solution upon delivery into the drying chamber of a spray dryer, e.g., operating in FSD mode; drying the feed solution in the drying chamber with heated air or a heated gas (e.g., nitrogen) to obtain a product, wherein larger particles of product separate out, e.g., drop out, while fines are carried by a stream of air or gas up to the top of the drying chamber (e.g., by natural convection) and to a cyclone, and re-introducing (e.g., at the top of the drying chamber or axially to the middle of the chamber) the fines into the drying chamber, wherein the re-introduced fines can agglomerate with newly formed product to generate an agglomerated product, wherein if the agglomerated product is large enough, it will separate out, if it is not large enough to separate out, the agglomerated product will be carried by convection to the top of the chamber and to the cyclone and re-introduced into the chamber. This process repeats until an agglomerated product that is large enough to drop out is formed. The fines can be re-introduced from the cyclone to the drying chamber via a feed pipe.

In some embodiments, rather than drying the feed solution with heated air or a heated gas, the feed solution can instead be spray congealed, e.g., the chamber is at room temperature (e.g., 21±4° C.) or is cooled, e.g., cooled gas (e.g., nitrogen) is used for the process.

FSD can further include collecting the agglomerated product in a first fluidizing chamber; which can be followed by discharging the agglomerated product from the first fluidizing chamber to a second fluidizing chamber, wherein a post-drying process can occur.

The agglomerated product (e.g., that separates out in the drying chamber) can then be transferred from the second fluidizing chamber to a third fluidizing chamber, where the agglomerated product is cooled. The agglomerated product (e.g., a solid dispersion of an amorphous compound) can then be further processed. For example, the product can be directly compressed. The product can optionally be blended with a surfactant, excipient, or pharmaceutically acceptable carrier, e.g., prior to direct compression. The product can optionally be further processed, e.g., milled, granulated, blended, and/or mixed with a melt granulate, surfactant, excipient, and/or pharmaceutically acceptable carrier.

FSD can be performed in a commercial spray dryer operating in fluidized spray dryer mode (FSD mode). FSD can be accomplished in either open cycle mode or closed cycle mode (e.g., the drying gas, e.g., nitrogen, is recycled). Examples of suitable spray dryers for use in FSD include dryers from Niro (e.g., the PSD line of spray driers manufactured by Niro: PHARMASD™; Chemical or SD line dryers). FSD can essentially be performed in any spray dryer that is configured to allow for the re-introduction of fines into the drying chamber.

Additional post drying, e.g., in a vacuum or fluidized bed dryer or a double cone or biconical post-dryer or a tumble dryer, can be performed if needed/applicable to remove further solvents. In some embodiments, a post-drying step is performed.

To remove the solvent or solvent mixture, vacuum drying, spray drying, fluidized spray drying, tray drying, lyophilization, rotovapping, and other drying procedures may be applied. Applying any of these methods using appropriate processing parameters, according to this disclosure, would provide Compound 1, or a pharmaceutically acceptable salt thereof in an amorphous state in the final solid dispersion product. Upon use of appropriate conditions (e.g., low outlet temperatures in the spray dryer, use of low boiling point solvents, use of heated gas) that result in a dispersion, e.g., powder, with desirable properties (e.g., median particle size (d50) of 40-200 microns 9 e.g., 40-150 microns), powder bulk density of >0.2 g/ml (e.g., 0.2 to 0.5 g/ml), or >0.25 g/ml, improved powder flowability (e.g., low cohesion forces, low interparticle internal friction); and/or dry powder with low OVIs (Organic Volatile Impurities), e.g., below ICH limits and/or user specifications), the dispersion can be directly compressed into a dosage form.

In some embodiments, the inlet temperature is between about 50° C. and about 200° C., e.g., between about 60° C. and about 150° C., between about 70° C. and about 100° C., between about 60° C. and about 95° C., between about 65° C. and about 85° C., between about 70° C. and about 90° C., between about 85° C. and about 95° C., or between about 70° C. and about 85° C.

In some embodiments, the outlet temperature is between about room temperature (e.g., USP room temperature (e.g., 21±4° C.)) and about 80° C., e.g., between about 25° C. and about 75° C., between about 30° C. and about 65° C., between about 35° C. and about 70° C., between about 40° C. and about 65° C., between about 45° C. and about 60° C., between about 35° C. and about 45° C., between about 35° C. and about 40° C., or between about 37° C. and about 40° C.

In some embodiments, the temperature set points of the fluidized beds (the temperature for each bed being selected independently from the temperature selected for another bed) is between about room temperature (e.g., USP room temperature (e.g., 21±4° C.)) and about 100° C., e.g., between about 30° C. and about 95° C., between about 40° C. and about 90° C., between about 50° C. and about 80° C., between about 60° C. and about 85° C., between about 65° C. and about 95° C., or between about 80° C. and about 95° C.

FSD can be performed on a mixture containing a compound of interest (e.g., a therapeutic agent (e.g., therapeutically active compound), e.g., Compound 1, or a pharmaceutically acceptable salt thereof). For example, FSD can be performed on a mixture containing Compound 1, or a pharmaceutically acceptable salt thereof (e.g., and one or more polymer(s), and optionally one or more surfactant(s), and optionally one or more additional excipients(s)) to obtain a solid dispersion of amorphous Compound 1, or a pharmaceutically acceptable salt thereof, e.g., that can be directly compressed into an oral dosage form (e.g., tablet). Alternatively, the dispersion can be blended with one or more excipients prior to compression.

In one embodiment, the process for preparing a solid dispersion of Compound 1 comprises:

a) forming a mixture of Compound 1, or a pharmaceutically acceptable salt thereof, one or more polymer(s), and one or more solvent(s); and b) rapidly removing the solvent(s) from the solution to form a solid amorphous dispersion comprising Compound 1, or a pharmaceutically acceptable salt thereof, and the one or more polymer(s). The one or more polymer(s) and one or more solvent(s) may be any of those disclosed herein.

In some embodiments, the solvent is removed by spray drying. In some embodiments the solid dispersion is tray dried using a convection tray dryer. In some embodiments, the solid dispersion is screened.

In one embodiment, Compound 1, or a pharmaceutically acceptable salt thereof, is crystalline. In another embodiment, Compound 1, or a pharmaceutically acceptable salt thereof, is amorphous.

As would be appreciated by one of skill in the art, spray drying may be done and is often done in the presence of an inert gas such as nitrogen. In certain embodiments, processes that involve spray drying may be done in the presence of a supercritical fluid involving carbon dioxide or a mixture including carbon dioxide.

In another embodiment, the process for preparing a solid dispersion of Compound 1, or a pharmaceutically acceptable salt thereof, comprises:

a) forming a mixture of Compound 1, or a pharmaceutically acceptable salt thereof, a polymer, and a solvent; and b) spray-drying the mixture to form a solid dispersion comprising Compound 1, or a pharmaceutically acceptable salt thereof, and the polymer.

Post-drying and/or polishing the wet spray dried dispersion to below ICH or given specifications for residual solvents can optionally be performed.

These processes may be used to prepare the pharmaceutical compositions disclosed herein. The amounts and the features of the components used in the processes may be as disclosed herein.

In some embodiments, the solvent comprises one or more volatile solvent(s) to dissolve or suspend Compound 1, or a pharmaceutically acceptable salt thereof, and the polymer(s). In some embodiments, the one or more solvent(s) completely dissolves Compound 1, or a pharmaceutically acceptable salt thereof, and the polymer(s).

In some embodiments, the one or more solvent(s) is a volatile solvent (e.g., methylene chloride, acetone, methanol, ethanol, chloroform, tetrahydrofuran (THF), or a mixture thereof). Examples of suitable volatile solvents include those that dissolve or suspend the therapeutically active compound either alone or in combination with another co-solvent. In some embodiments, the solvent(s) completely dissolves the therapeutically active compound. In some embodiments, the solvent is acetone. In some embodiments, the solvent is methanol.

In some embodiments, the solvent is a non-volatile solvent (e.g., organic acids such as glacial acetic acid, dimethyl sulfoxide (DMSO), dimethylformamide (DMF), or water). In some embodiments, a non-volatile solvent is a component in a solvent system. For example the non-volatile solvent is present as a component in a solvent from about 1% to about 20% w/w (e.g., from about 3% w/w to about 15% w/w, from about 4% w/w to about 12% w/w, or from about 5% w/w to about 10% w/w).

In some embodiments, the solvent is a mixture of solvents. For example, the solvent can include from about 0% to about 30% acetone and from about 70% to about 100% methanol, or the solvent can include from about 0% to about 40% acetone and from about 60% to about 100% methanol. Other exemplary ratios of methanol to acetone include 80:20, 75:25, 70:30, 60:40, 55:45, and 50:50.

In some embodiments, the solvent is a combination of solvents including at least one non-volatile solvent. For example, the solvent is a combination of components that includes both a volatile solvent and a non-volatile solvent. In some embodiments, the solvent system is a combination of a volatile solvent or combination of solvents such as methanol and acetone with a non-volatile solvent such as glacial acetic acid. For example, the solvent system comprises from about 40% to about 80% methanol, from about 20% to about 35% acetone, and from about 1% to about 15% glacial acetic acid (e.g., from about 50% to about 70% methanol, from about 25% to about 30% acetone, and from about 3% to about 12% glacial acetic acid).

In some embodiments, the solvent system is a combination of a volatile solvent or combination of solvents such as methanol and acetone with a non-volatile solvent such as water. For example, the solvent system comprises from about 40% to about 80% methanol, from about 20% to about 35% acetone, and from about 0.1% to about 15% water (e.g., from about 50% to about 70% methanol, from about 25% to about 30% acetone, and from about 1% to about 5% water).

Pharmaceutical Compositions

Pharmaceutical compositions of the solid dispersion may be made by a process described herein. For example, a solid dispersion of: (a) Compound 1, or a pharmaceutically acceptable salt thereof, and (b) one or more polymer(s), and optionally one or more surfactant(s) and optionally one or more additional excipient(s).

Provided herein are pharmaceutical compositions, comprising: (a) a solid dispersion, comprising Compound 1, or a pharmaceutically acceptable salt thereof, and a polymer; and (b) one or more pharmaceutically acceptable carrier(s). Examples of pharmaceutically acceptable carriers are fillers, disintegrants, wetting agents, glidants, and lubricants.

In some embodiments, the pharmaceutical compositions may be orally administered in any orally acceptable dosage form including, but not limited to, capsules, tablets, emulsions and aqueous suspensions, dispersions and solutions.

In some embodiments the pharmaceutical composition is a tablet.

In some embodiments the pharmaceutical composition comprises a directly compressed dosage form of Compound 1, or a pharmaceutically acceptable salt thereof.

In some embodiments, the pharmaceutical composition also includes a filler. The filler can be, for example, microcrystalline cellulose, lactose, mannitol, ethyl cellulose, sorbitol, starch, sucrose, calcium phosphate, powdered cellulose, silicified microcrystalline cellulose, isomalt, or mixtures thereof. In some embodiments, the filler is microcrystalline cellulose.

In some embodiments, the filler is present in the pharmaceutical composition in an amount of between about 10% w/w and 50% w/w (e.g., between about 15% w/w and about 45% w/w; between about 20% w/w and about 40% w/w; between about 25% w/w and about 35% w/w; or between about 28% w/w and about 32% w/w). In some embodiments, the filler is present in the pharmaceutical composition in an amount of from about 20% w/w to about 35% w/w, for example from about 25% w/w to about 34% w/w, or from about 26% w/w to about 33% w/w, or from about 27% w/w to about 32% w/w, for example, about 28% w/w, about 28.5% w/w, about 29% w/w, about 29.5% w/w about 30% w/w, about 30.5% w/w, about 31% w/w, or about 31.5% w/w. In some embodiments, the filler is present in the pharmaceutical composition in an amount of about 29% w/w, about 29.1% w/w, about 29.2% w/w, about 29.3% w/w, about 29.4% w/w, about 29.5% w/w, about 29.6% w/w, about 29.7% w/w, about 29.8% w/w, about 29.9% w/w, or about 30% w/w. In some embodiments, the filler is present in the pharmaceutical composition in an amount of between about 25% w/w and about 35% w/w. In some embodiments, the filler is present in the pharmaceutical composition in an amount of about 29.5% w/w.

In some embodiments, the pharmaceutical composition also includes a disintegrant. The disintegrant can be, for example, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, or mixtures thereof. In some embodiments, the disintegrant is croscarmellose sodium.

In some embodiments, the disintegrant is present in the pharmaceutical composition in an amount of between about 1% w/w and 15% w/w (e.g., between about 3% w/w and about 12% w/w; between about 4% w/w and about 10% w/w; between about 5% w/w and about 7% w/w; or between about 6% w/w and about 7% w/w). In some embodiments, the disintegrant is present in the pharmaceutical composition in an amount of about 3% w/w, about 3.5% w/w, about 4% w/w, about 49.5% w/w about 5% w/w, about 5.5% w/w, about 6% w/w, or about 6.5% w/w, about 7% w/w, about 7.5% w/w, about 8% w/w, about 8.5% w/w, about 9% w/w, about 9.5% w/w, or about 10% w/w. In some embodiments, the disintegrant is present in the pharmaceutical composition in an amount of between about 5% w/w and about 7% w/w. In some embodiments, the disintegrant is present in the pharmaceutical composition in an amount of about 6% w/w.

In some embodiments, the pharmaceutical composition also includes a wetting agent. The wetting agent can be, for example, sodium lauryl sulfate, sodium dodecyl sulfate, polysorbates (such as Tween 20 and Tween 80), poloxamers (such as Poloxamer 335 and Poloxamer 407), glyceryl monooleate, or mixtures thereof. In some embodiments, the wetting agent is sodium lauryl sulfate.

In some embodiments, the wetting agent is present in the pharmaceutical composition in an amount of between about 0.1% w/w and 2% w/w (e.g., between about 0.5% w/w and about 2% w/w; between about 0.5% w/w and about 1.5% w/w; or between about 1% w/w and about 1.5% w/w). In some embodiments, the wetting agent is present in the pharmaceutical composition in an amount of about 0.1% w/w, about 0.2% w/w, about 0.3% w/w, about 0.4% w/w about 0.5% w/w, about 0.6% w/w, about 0.7% w/w, or about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, or about 2% w/w. In some embodiments, the wetting agent is present in the pharmaceutical composition in an amount of between about 0.5% w/w and about 1.5% w/w. In some embodiments, the wetting agent is present in the pharmaceutical composition in an amount of about 1% w/w.

In some embodiments, the pharmaceutical composition also includes a glidant. The glidant can be, for example, silicon dioxide, colloidal silicon dioxide, tribasic calcium phosphate, magnesium stearate, magnesium trisilicate, powdered cellulose, talc, starch, and mixtures thereof. In some embodiments, the glidant is colloidal silicon dioxide.

In some embodiments, the glidant is present in the pharmaceutical composition in an amount of between about 0.1% w/w and 5% w/w (e.g., between about 1% w/w and about 4% w/w; between about 1% w/w and about 3% w/w; or between about 1.5% w/w and about 2.5% w/w). In some embodiments, the glidant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the glidant is present in the pharmaceutical composition in an amount of about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, about 2.5% w/w, about 2.6% w/w, about 2.7% w/w, about 2.8% w/w, about 2.9% w/w, or about 3% w/w. In some embodiments, the glidant is present in the pharmaceutical composition in an amount of between about 1% w/w and about 3% w/w. In some embodiments, the glidant is present in the pharmaceutical composition in an amount of about 2% w/w.

In some embodiments, the pharmaceutical composition also includes a lubricant. The lubricant can be, for example, magnesium stearate, talc, sodium stearyl fumarate, glyceryl behenate, hydrogenated vegetable oil, zinc stearate, calcium stearate, sucrose stearate, polyvinyl alcohol, magnesium lauryl sulfate, or mixtures thereof. In some embodiments, the lubricant is magnesium stearate.

In some embodiments, the lubricant is present in the pharmaceutical composition in an amount of between about 0.1% w/w and 5% w/w (e.g., between about 1% w/w and about 4% w/w; between about 1% w/w and about 3% w/w; or between about 1% w/w and about 2% w/w). In some embodiments, the lubricant is present in the pharmaceutical composition in an amount of about 0.5% w/w, about 1% w/w, about 1.5% w/w, about 2% w/w about 2.5% w/w, about 3% w/w, about 3.5% w/w, or about 4% w/w, about 4.5% w/w, or about 5% w/w. In some embodiments, the lubricant is present in the pharmaceutical composition in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, 2.1% w/w, about 2.2% w/w, about 2.3% w/w, about 2.4% w/w, or about 2.5% w/w. In some embodiments, the lubricant is present in the pharmaceutical composition in an amount of between about 0.5% w/w and about 2.5% w/w. In some embodiments, the lubricant is present in the pharmaceutical composition in an amount of about 1.5% w/w.

In some embodiments, the solid dispersion makes up about 25% to 85% by weight of the total weight of the pharmaceutical composition. In some embodiments, the solid dispersion makes up about 50% to about 70% by weight of the total weight of the pharmaceutical composition.

In some embodiments, the Compound 1, or a pharmaceutically acceptable salt thereof makes up about 15% to 45% of the total weight of the pharmaceutical composition, and the one or more polymer(s) makes up about 15% to 45% of the total weight of the pharmaceutical composition.

In some embodiments, the Compound 1, or a pharmaceutically acceptable salt thereof makes up about 20% w/w of the pharmaceutical composition, the one or more polymer(s) makes up about 40% w/w of the pharmaceutical composition.

In some embodiments, the Compound 1, or a pharmaceutically acceptable salt thereof makes up about 25% w/w of the pharmaceutical composition, the one or more polymer(s) makes up about 35% w/w of the pharmaceutical composition.

In some embodiments, the Compound 1, or a pharmaceutically acceptable salt thereof makes up about 30% w/w of the pharmaceutical composition, the one or more polymer(s) makes up about 30% w/w of the pharmaceutical composition.

In some embodiments, the Compound 1, or a pharmaceutically acceptable salt thereof makes up about 35% w/w of the pharmaceutical composition, the one or more polymer(s) makes up about 25% w/w of the pharmaceutical composition.

In some embodiments, the solid dispersion makes up from between about 50% w/w to about 70% w/w of the pharmaceutical composition, the filler makes up from between about 25% w/w to about 35% w/w of the pharmaceutical composition, the disintegrant makes up from between about 5% w/w to about 7% w/w of the pharmaceutical composition, the wetting agent makes up from between about 0.5% w/w to about 1.5% w/w of the pharmaceutical composition, the glidant makes up from between about 1% w/w to about 3% w/w of the pharmaceutical composition, the lubricant makes up from between about 0.5% w/w to about 2.5% w/w of the pharmaceutical composition thereby totaling 100% by weight of the composition.

In some embodiments, the solid dispersion makes up about 60% w/w of the pharmaceutical composition, the filler makes up about 29.5% w/w of the pharmaceutical composition, the disintegrant makes up about 6% w/w of the pharmaceutical composition, the wetting agent makes up about 1% w/w of the pharmaceutical composition, the glidant makes up about 2% w/w of the pharmaceutical composition, the lubricant makes up about 1.5% w/w of the pharmaceutical composition.

In some embodiments, the pharmaceutical composition comprises, from between about 25% w/w to about 35% w/w of Compound 1, or a pharmaceutically acceptable salt thereof, from between about 25% w/w to about 35% w/w of hypromellose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and rom between about 0.5% w/w to about 2.5% w/w of magnesium stearate, thereby totaling 100% by weight of the composition.

In some embodiments, the pharmaceutical composition comprises, about 30% w/w of Compound 1, or a pharmaceutically acceptable salt thereof, about 30% w/w of hypromellose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

In some embodiments, the solid dispersion, filler, disintegrant, wetting agent, glidant, and lubricant are added intragranularly. In some embodiments, an additional amount of the filler, disintegrant, glidant, and lubricant are added extragranularly.

In some embodiments, the pharmaceutical composition comprises, the following intragranularly added components: the solid dispersion makes up from about 50% w/w to about 70% w/w of the pharmaceutical composition, the filler makes up from about 18% w/w to about 26% w/w of the pharmaceutical composition, disintegrant makes up from about 2% w/w to about 6% w/w of the pharmaceutical composition, wetting agent makes up from about 0.5% w/w to about 1.5% w/w of the pharmaceutical composition, glidant makes up from about 0.5% w/w to about 1.5% w/w of the pharmaceutical composition, and lubricant makes up from about 0.25% w/w to about 1% w/w of the pharmaceutical composition.

In some embodiments, a the pharmaceutical composition comprises the following extragranularly added components: an additional amount of the filler makes up from about 4% w/w to about 12% w/w of the pharmaceutical composition, an additional amount of the disintegrant makes up from about 1% w/w to about 3% w/w of the pharmaceutical composition, an additional amount of the glidant makes up from about 0.5% w/w to about 1.5% w/w of the pharmaceutical composition, and an additional amount of the lubricant makes up from about 0.5% w/w to about 1.5% w/w of the pharmaceutical composition, and are added extragranularly.

In some embodiments, the pharmaceutical composition comprises, the following intragranularly added components: the solid dispersion makes up about 60% w/w of the pharmaceutical composition, the filler makes up about 21.5% w/w of the pharmaceutical composition, disintegrant makes up about 4% w/w of the pharmaceutical composition, wetting agent makes up about 1% w/w of the pharmaceutical composition, glidant makes up about 1% w/w of the pharmaceutical composition, and lubricant makes up about 0.5% w/w of the pharmaceutical composition.

In some embodiments, a the pharmaceutical composition comprises the following extragranularly added components: an additional amount of the filler makes up about 8% w/w of the pharmaceutical composition, an additional amount of the disintegrant makes up about 2% w/w of the pharmaceutical composition, an additional amount of the glidant makes up about 1% w/w of the pharmaceutical composition, and an additional amount of the lubricant makes up about 1% w/w of the pharmaceutical composition, and are added extragranularly.

In some embodiments, the pharmaceutical composition comprises, the following intragranularly added components: the solid dispersion comprising Compound 1, or a pharmaceutically acceptable salt thereof, and hypromellose acetate succinate (HPMCAS), makes up from about 50% w/w to about 70% w/w of the pharmaceutical composition, microcrystalline cellulose makes up from about 18% w/w to about 26% w/w of the pharmaceutical composition, croscarmellose sodium makes up from about 2% w/w to about 6% w/w of the pharmaceutical composition, sodium lauryl sulfate makes up from about 0.5% w/w to about 1.5% w/w of the pharmaceutical composition, colloidal silicon dioxide makes up from about 0.5% w/w to about 1.5% w/w of the pharmaceutical composition, and magnesium stearate makes up from about 0.25% w/w to about 1% w/w of the pharmaceutical composition.

In some embodiments, a the pharmaceutical composition comprises the following extragranularly added components: an additional amount of microcrystalline cellulose makes up from about 4% w/w to about 12% w/w of the pharmaceutical composition, an additional amount of croscarmellose sodium makes up from about 1% w/w to about 3% w/w of the pharmaceutical composition, an additional amount of colloidal silicon dioxide makes up from about 0.5% w/w to about 1.5% w/w of the pharmaceutical composition, and an additional amount of magnesium stearate makes up from about 0.5% w/w to about 1.5% w/w of the pharmaceutical composition, and are added extragranularly.

In some embodiments, the pharmaceutical composition comprises, the following intragranularly added components: the solid dispersion comprising Compound 1, or a pharmaceutically acceptable salt thereof, and hypromellose acetate succinate (HPMCAS), makes up about 60% w/w of the pharmaceutical composition, microcrystalline cellulose makes up about 21.5% w/w of the pharmaceutical composition, croscarmellose sodium makes up about 4% w/w of the pharmaceutical composition, sodium lauryl sulfate makes up about 1% w/w of the pharmaceutical composition, colloidal silicon dioxide makes up about 1% w/w of the pharmaceutical composition, and magnesium stearate makes up about 0.5% w/w of the pharmaceutical composition.

In some embodiments, a the pharmaceutical composition comprises the following extragranularly added components: an additional amount of microcrystalline cellulose makes up about 8% w/w of the pharmaceutical composition, an additional amount of croscarmellose sodium makes up about 2% w/w of the pharmaceutical composition, an additional amount of colloidal silicon dioxide makes up about 1% w/w of the pharmaceutical composition, and an additional amount of magnesium stearate makes up about 1% w/w of the pharmaceutical composition, and are added extragranularly.

A subject may be administered a dose of Compound 1, or a pharmaceutically acceptable salt thereof, as described in Example 5. Lower or higher doses than those recited above may be required. Specific dosage and treatment regimens for any particular subject will depend upon a variety of factors, including the activity of the specific compound, employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Use

The inhibitory activities of Compound 1, and pharmaceutically acceptable salts thereof provided herein against IDH1 mutants (e.g., IDH1R132H or IDH1R132C) can be tested by methods described in Example A of PCT Publication No. WO 2013/107291 and US Publication No. US 2013/0190249, hereby incorporated by reference in their entirety, or analogous methods.

Provided is a method for treating an advanced solid tumor, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1, comprising administering to a subject in need thereof a pharmaceutical composition comprising: (a) Compound 1, or a pharmaceutically acceptable salt thereof, as part of a solid dispersion, and optionally (b) one or more pharmaceutically acceptable carrier(s). In one embodiment, the advanced solid tumor, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), to be treated is characterized by a mutant allele of IDH1, wherein the IDH1 mutation results in a new ability of the enzyme to catalyze the NAPH-dependent reduction of α-ketoglutarate to R(−)-2-hydroxyglutarate in a patient. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

Advanced solid tumors, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation results in a new ability of the enzyme to catalyze the NAPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds, and methods of one aspect of this invention are useful to treat advanced solid tumors, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 imparting such activity and in particular an IDH1 R132H or R132C mutation.

In one embodiment, the efficacy of treatment of advanced hematologic malignancies, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 is monitored by measuring the levels of 2HG in the subject. Typically levels of 2HG are measured prior to treatment, wherein an elevated level is indicated for the use of Compound 1, or a pharmaceutically acceptable salt thereof, to treat the advanced hematologic malignancies, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, evaluation of bone marrow biopsies and/or aspirates, complete blood counts and examination of peripheral blood films, improvement in the general health of the subject, and alterations in other biomarkers that are associated with cancer treatment efficacy.

2HG can be detected in a sample by the methods of PCT Publication No. WO WO/2011/050210 and US Publication No. US2012/121515 hereby incorporated by reference in their entirety, or by analogous methods.

Methods of Evaluating Samples and/or Subjects

This section provides methods of obtaining and analyzing samples and of analyzing subjects.

Embodiments of the method comprise evaluation of one or more parameters related to IDH1, an alpha hydroxy neoactivity, e.g., 2HG neoactivity, e.g., to evaluate the IDH1 2HG neoactivity genotype or phenotype. The evaluation can be performed, e.g., to select, diagnose or prognose the subject, to select a therapeutic agent, e.g., an inhibitor, or to evaluate response to the treatment or progression of disease. In an embodiment the evaluation, which can be performed before and/or after treatment has begun, is based, at least in part, on analysis of a tumor sample, cancer cell sample, or precancerous cell sample, from the subject. E.g., a sample from the patient can be analyzed for the presence or level of an alpha hydroxy neoactivity product, e.g., 2HG, e.g., R-2HG, by evaluating a parameter correlated to the presence or level of an alpha hydroxy neoactivity product, e.g., 2HG, e.g., R-2HG. An alpha hydroxy neoactivity product, e.g., 2HG, e.g., R-2HG, in the sample can be determined by a chromatographic method, e.g., by LC-MS analysis. It can also be determined by contact with a specific binding agent, e.g., an antibody, which binds the alpha hydroxy neoactivity product, e.g., 2HG, e.g., R-2HG, and allows detection. In an embodiment the sample is analyzed for the level of neoactivity, e.g., an alpha hydroxy neoactivity, e.g., 2HG neoactivity. In an embodiment the sample is analysed for the presence of a mutant IDH1, protein having an alpha hydroxy neoactivity, e.g., 2HG neoactivity (or a corresponding RNA). E.g., a mutant protein specific reagent, e.g., an antibody that specifically binds an IDH1 mutant protein, e.g., an antibody that specifically binds an IDH1-R132H mutant protein, can be used to detect neoactive mutant enzymeIn an embodiment a nucleic acid from the sample is sequenced to determine if a selected allele or mutation of IDH1 disclosed herein is present. In an embodiment the analysis is other than directly determining the presence of a mutant IDH1 protein (or corresponding RNA) or sequencing of an IDH1 gene. In an embodiment the analysis is other than directly determining, e.g., it is other than sequencing genomic DNA or cDNA, the presence of a mutation at residue 132 of IDH1. E.g., the analysis can be the detection of an alpha hydroxy neoactivity product, e.g., 2HG, e.g., R-2HG, or the measurement of the mutation's an alpha hydroxy neoactivity, e.g., 2HG neoactivity. In an embodiment the sample is removed from the patient and analyzed. In an embodiment the evaluation can include one or more of performing the analysis of the sample, requesting analysis of the sample, requesting results from analysis of the sample, or receiving the results from analysis of the sample. (Generally herein, analysis can include one or both of performing the underlying method or receiving data from another who has performed the underlying method.)

In an embodiment the evaluation, which can be performed before and/or after treatment has begun, is based, at least in part, on analysis of a tissue (e.g., a tissue other than a tumor sample), or bodily fluid, or bodily product. Exemplary tissues include lymph node, skin, hair follicles and nails. Exemplary bodily fluids include blood, plasma, urine, lymph, tears, sweat, saliva, semen, and cerebrospinal fluid. Exemplary bodily products include exhaled breath. E.g., the tissue, fluid or product can be analyzed for the presence or level of an alpha hydroxy neoactivity product, e.g., 2HG, e.g., R-2HG, by evaluating a parameter correlated to the presence or level of an alpha hydroxy neoactivity product, e.g., 2HG, e.g., R-2HG. An alpha hydroxy neoactivity product, e.g., 2HG, e.g., R-2HG, in the sample can be determined by a chromatographic method, e.g., by LC-MS analysis. It can also be determend by contact with a specific binding agent, e.g., an antibody, which binds the alpha hydroxy neoactivity product, e.g., 2HG, e.g., R-2HG, and allows detection. In embodiments where sufficient levels are present, the tissue, fluid or product can be analyzed for the level of neoactivity, e.g., an alpha hydroxy neoactivity, e.g., the 2HG neoactivity. In an embodiment the sample is analysed for the presence of a mutant IDH1 protein having an alpha hydroxy neoactivity, e.g., 2HG neoactivity (or a corresponding RNA). E.g., a mutant protein specific reagent, e.g., an antibody that specifically binds an IDH1 protein, e.g., an antibody that specifically binds an IDH1-R132H mutant protein can be used to detect neoactive mutant enzyme. In an embodiment a nucleic acid from the sample is sequenced to determine if a selected allele or mutation of IDH1 disclosed herein is present. In an embodiment the analysis is other than directly determining the presence of a mutant IDH1 protein (or corresponding RNA) or sequencing of an IDH1 gene. E.g., the analysis can be the detection of an alpha hydroxy neoactivity product, e.g., 2HG, e.g., R-2HG, or the measurement of 2HG neoactivity. In an embodiment the tissue, fluid or product is removed from the patient and analyzed. In an embodiment the evaluation can include one or more of performing the analysis of the tissue, fluid or product, requesting analysis of the tissue, fluid or product, requesting results from analysis of the tissue, fluid or product, or receiving the results from analysis of the tissue, fluid or product.

In an embodiment the evaluation, which can be performed before and/or after treatment has begun, is based, at least in part, on alpha hydroxy neoactivity product, e.g., 2HG, e.g., R-2HG, imaging of the subject. In embodiments magnetic resonance methods are is used to evaluate the presence, distribution, or level of an alpha hydroxy neoactivity product, e.g., 2HG, e.g., R-2HG, in the subject. In an embodiment the subject is subjected to imaging and/or spectroscopic analysis, e.g., magnetic resonance-based analysis, e.g., MRI and/or MRS e.g., analysis, and optionally an image corresponding to the presence, distribution, or level of an alpha hydroxy neoactivity product, e.g., 2HG, e.g., R-2HG, or of the tumor, is formed. Optionally the image or a value related to the image is stored in a tangible medium and/or transmitted to a second site. In an embodiment the evaluation can include one or more of performing imaging analysis, requesting imaging analysis, requesting results from imaging analysis, or receiving the results from imaging analysis.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

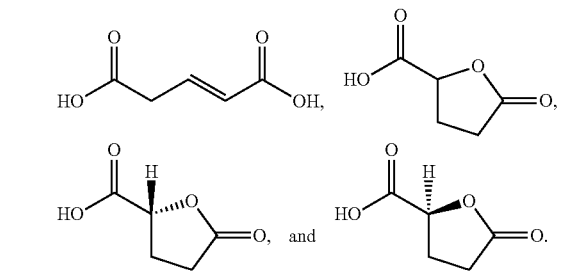

In one embodiment the advanced hematologic malignancy such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma) is a tumor wherein at least 30, 40, 50, 60, 70, 80 or 90% of the tumor cells carry an IDH1 mutation, and in particular an IDH1 R132H or R132C mutation, at the time of diagnosis or treatment.

In one embodiment, the advanced hematologic malignancy to be treated is AML, characterized by the presence of a mutant allele of IDH1. In some embodiments, the AML is relapsed and/or primary refractory. In some embodiments, the AML is relapsed. In some embodiments, the AML is primary refractory. In other embodiments, the AML is untreated.

In another embodiment, the advanced hematologic malignancy to be treated is MDS, characterized by the presence of a mutant allele of IDH1. In another embodiment, the advanced hematologic malignancy to be treated is MDS with refractory anemia with excess blasts (subtype RAEB-1 or RAEB-2). In other embodiments, the MDS is considered high-risk by the IPSS-R (Greenberg et al. *Blood.* 2012; 120(12):2454-65). In other embodiments, the MDS is recurrent. In other embodiments, the MDS is refractory. In other embodiments, the subject having MDS is intolerant to established therapy known to provide clinical benefit for their conditions, according to the treating physician.

In another embodiment, the advanced hematologic malignancy to be treated is CMML, characterized by the presence of a mutant allele of IDH1. In another embodiment, the CMML is relapsed and/or primary refractory. In another embodiment, the CMML is relapsed. In another embodiment, the CMML is primary refractory.

Treatment methods described herein can additionally comprise various evaluation steps prior to and/or following treatment with a pharmaceutical composition comprising: (a) Compound 1, or a pharmaceutically acceptable salt thereof, as part of a solid dispersion, and optionally (b) one or more pharmaceutically acceptable carrier(s).

In one embodiment, prior to and/or after treatment with a pharmaceutical composition comprising: (a) Compound 1, or a pharmaceutically acceptable salt thereof, as part of a solid dispersion, and optionally (b) one or more pharmaceutically acceptable carrier(s), the method further comprises evaluating the growth, size, weight, invasiveness, stage and/or other phenotype of the advanced hematologic malignancies, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1.

In one embodiment, prior to and/or after treatment with a pharmaceutical composition comprising: (a) Compound 1, or a pharmaceutically acceptable salt thereof, as part of a solid dispersion, and optionally (b) one or more pharmaceutically acceptable carrier(s), the method further comprises evaluating the IDH1 genotype of the advanced hematologic malignancies, such as acute myelogenous leukemia (AML), myelodysplastic syndrome (MDS), myeloproliferative neoplasms (MPN), myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1. This may be achieved by ordinary methods in the art, such as DNA sequencing, immuno analysis, and/or evaluation of the presence, distribution or level of 2HG.

In one embodiment, prior to and/or after treatment with a pharmaceutical composition comprising: (a) Compound 1, or a pharmaceutically acceptable salt thereof, as part of a solid dispersion, and optionally (b) one or more pharmaceutically acceptable carrier(s), the method further comprises determining the 2HG level in the subject. This may be achieved by spectroscopic analysis, e.g., magnetic resonance-based analysis, e.g., MRI and/or MRS measurement, sample analysis of bodily fluid, such as blood, plasma, urine, or spinal cord fluid analysis, or by analysis of surgical material, e.g., by mass-spectroscopy (e.g. LC-MS, GC-MS), or any of the methods described herein.

EXAMPLES

General Methods

In the following examples, reagents may be purchased from commercial sources (including Alfa, Acros, Sigma Aldrich, TCI and Shanghai Chemical Reagent Company), and used without further purification.

X-Ray Powder Diffraction (XRPD) Parameters:

XRPD analysis is performed using a PANalytical Empyrean X-ray powder diffractometer (XRPD) with a 12-auto sample stage. The XRPD parameters used are listed in Table 3.

TABLE 3

| Parameters for Reflection Mode | |
| --- | --- |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0170 |
| Scan speed (°/min) | About 10 |

Differential Scanning Calorimetry (DSC) Parameters:

DSC analysis is performed using a TA Q100, or Q200/Q2000 DSC from TA Instruments. The temperature is ramped from room temperature to the desired temperature at a heating rate of 10° C./min using $N_2$ as the purge gas, with pan crimped.

Thermogravimetric Analysis (TGA) Parameters:

TGA analysis is performed using a TA Q500/Q5000 TGA from TA Instruments. The temperature is ramped from room temperature to the desired temperature at a heating rate of 10° C./min or 20° C./min using $N_2$ as the purge gas.

Example 1

Compound 1 and various amounts of Hypromellose Acetate Succinate-MG (Hypromellose Acetate Succinate, MG grade, Shin-Etsu Chemical Co.) polymer may be used to generate the amorphous solid dispersion intermediate and formulation presented in this Example 1. Success criteria may include manufacturing the batches with reasonable yield (>60%), low residual solvents (≤3000 ppm), as well as meeting specifications for assay and purity.

Step 1: Preparation of Compound 1 Amorphous Solid Dispersion

Form 1 and hypromellose acetate succinate (HPMCAS) (50%/50%, w/w) are weighed and dissolved in methanol and spray-dried (Büchi B-290) to produce an amorphous Compound 1 and hypromellose acetate succinate (HPMCAS) solid dispersion. Spray drying processing parameters include nitrogen as the drying gas, an inlet temperature of about 85° C. to 95° C., an outlet temperature of about 37° C. to 40° C., spray solution concentration of about 5% w/w/, secondary drying of 12 to 18 hours at 40° C. The amorphous solid dispersion is further dried in a vacuum oven and then screened. The amorphous solid dispersion may be packaged in double polyethylene bags with twisted nylon tie and placed in a high density polyethylene (HDPE) container containing desiccant and stored at 2-8° C. until the next step of processing.

Step 2: Manufacture of Compound 1 Tablets

Compound 1 and hypromellose acetate succinate amorphous solid dispersion intermediate and all other excipients disclosed in Table 4 are weighed and sieved for blending.

Weighing and Screening Intragranular Ingredients

Compound 1 and hypromellose acetate succinate amorphous solid dispersion is mixed with microcrystalline cellulose, croscarmellose sodium, sodium lauryl sulfate, colloidal silicon dioxide, and magnesium stearate in a suitable blender.

TABLE 4

Batch formulation composition

| | Component | Function | Amount per batch (g) 50 mg tablet | Amount per batch (g) 200 mg tablet |
|---|---|---|---|---|
| Intragranular | Compound 1* | Therapeutically Active Compound | 241.75 | 1204.01 |
| | Hypromellose Acetate Succinate* | Stabilizer | 241.75 | 1204.01 |
| | Microcrystalline Cellulose | Filler | 173.26 | 862.87 |
| | Croscarmellose Sodium | Disintegrant | 32.23 | 160.53 |
| | Sodium Lauryl Sulfate | Wetting agent | 8.06 | 40.13 |
| | Colloidal Silicon Dioxide | Glidant | 8.06 | 40.13 |
| | Magnesium Stearate | Lubricant | 4.03 | 20.07 |
| Extragranular | Microcrystalline Cellulose | Filler | 64.47 | 321.07 |
| | Croscarmellose Sodium | Disintegrant | 16.12 | 80.27 |

TABLE 4-continued

Batch formulation composition

| Component | Function | Amount per batch (g) 50 mg tablet | Amount per batch (g) 200 mg tablet |
|---|---|---|---|
| Colloidal Silicon Dioxide | Glidant | 8.06 | 40.13 |
| Magnesium Stearate | Lubricant | 8.06 | 40.13 |
| Total | | 805.85 | 4013.36 |
| Theoretical number of tablets | | 4835 | 6020 |

*Compound 1 and Hypromellose Acetate Succinate amorphous solid dispersion intermediate Intragranule Blending The intra-granule blend is roller compacted and the compacted material is sized to produce granules.

Dry Granulation/Sizing

Extra-granular microcrystalline cellulose, croscarmellose sodium, colloidal silicon and magnesium stearate are weighed and sieved for blending.

Weighing and Screening Extragranular Ingredients

The screened granules and extra-granular excipients are added to a suitable blender and blended.

Extragranule Blending

The blend is compressed using a rotary tablet press set-up to manufacture tablets of the appropriate shape/size and required weight, thickness, and hardness.

Compression

Bulk Compound 1 tablets are packaged in double sealed polyethylene bags containing 30 g silica gel packs which are placed in foil lined drums and stored at 2-8° C. Tablets are subsequently packaged.

TABLE 5

Tablet composition

| | | 50 mg Tablet | | 200 mg Tablet | |
|---|---|---|---|---|---|
| Component | Function | Amount per Tablet (mg) | Content (%) | Amount per Tablet (mg) | Content (%) |
| Compound 1* | Therapeutically Active Compound | 50.0 | 30 | 200.0 | 30 |
| Hypromellose Acetate Succinate* | Stabilizer | 50.0 | 30 | 200.0 | 30 |
| Microcrystalline Cellulose | Filler | 49.2 | 29.5 | 196.7 | 29.5 |
| Croscarmellose Sodium | Disintegrant | 10.0 | 6 | 40.0 | 6 |
| Sodium Lauryl Sulfate | Wetting agent | 1.7 | 1 | 6.8 | 1 |
| Colloidal Silicon Dioxide | Glidant | 3.3 | 2 | 13.2 | 2 |
| Magnesium Stearate | Lubricant | 2.5 | 1.5 | 10.0 | 1.5 |
| Total | | 166.7 | 100.0 | 666.7 | 100.0 |

Example 2 Synthesis of Form 1

A mixture of Compound 1 (3.5 kg, 7.28 mol) in 1,4-dioxane (35 L) is degassed by $N_2$ bubbling for a maximum of 20 min. 2-chloro-4-cyanopyridine (1.21 kg, 8.73 mol), tris(dibenzylideneacetone)-dipalladium(0) (167 g, 0.18 mol), and 4,5-bis(diphenylphosphino)-9,9-dimethylxanthene (xantphos) (211 g, 0.36 mol) are added and the reaction mixture is degassed by $N_2$ bubbling for a maximum of 10 min. K2CO$_3$ (1.21 kg, 8.73 mol) is added and the reaction mixture is degassed by $N_2$ bubbling for a maximum of 30 min. The reaction mixture is heated at 90-100° C. for 4 to 24 hours until the reaction is complete. The reaction mixture is then cooled to 15-25° C. and filtered through Celite and is washed with ethyl acetate, and the combined filtrate and wash are concentrated.

The 1,4-dioxane is removed, and the residual solid is dissolved in ethyl acetate (77.5 L). The ethyl acetate solution is washed successively with a 5% aqueous solution of NaHSO₃, a 2% aqueous solution of EDTA disodium, and a 1% aqueous solution of EDTA disodium salt. The organic phase is treated with activated carbon at 55-65° C. for a maximum of 2 h, and is purified by silica gel chromatography. After chromatography, the resulting product is purified by two recrystallizations: first Compound 1 is dissolved in ethyl acetate and heated to 60-70° C. and heptane is added. The reaction mixture is cooled to 15-25° C. and stirred for 1-3 h. The product is filtered and is dissolved in dichloromethane, then is filtered and is precipitated with heptane, is filtered and dried to produce Form 1.

Example 3 Synthesis of Form 2

Method A:
About 100 mg of Compound 1 is mixed with 0.4 mL MeOH and stirred at room temperature for 12 h. The suspension is subsequently centrifuged, and the white solid is isolated.

Method B:
About 10 mg of Compound 1 in 0.2-0.4 mL of a mixture of MeOH:H₂O (9:1) in a 3-mL glass vial. The resulting visually clear solution is covered with a cap and subjected to slow evaporation to induce precipitation. The solid is isolated.

Method C:
About 15 mg of Compound 1 is dissolved in a mixture of EtOH:H₂O (8:7 volume/volume) or Methyl ethyl ketone (MEK) at 50° C. and stirred at 50° C. for 30 min. Then the solution is cooled slowly to 5° C. at 0.1° C./min, and is stirred at 5° C. overnight. The solid is isolated.

Example 4

The following three homogenous suspensions of Compound 1 are provided:

Form 2 in vehicle (1% d-alpha-tocopheryl polyethylene glycol 1000 succinate (TPGS):1% HPMCAS in water), an amorphous solid dispersion of 25% w/w Form 2 and 75% w/w HPMCAS-M (Solid Dispersion A) in vehicle, and an amorphous solid dispersion of 25% w/w Form 2 and 75% w/w PVAP (Solid Dispersion B) in vehicle (200 mg/kg in 10 mL/kg).

Each suspension is prepared on the day of dosing, and the Sprague Dawley rats are dosed orally. Serial plasma samples are taken at different time points following dosing. Compound 1 concentration in plasma is determined using a sensitive and specific LC/MS method. PK parameters, including $AUC_{0-72\ hr}$ and Cmax, are calculated using WinNonlin software.

For Form 2, the $C_{max}$ is 1600 ng/mL, and $AUC_{0-72\ hr}$ is 21700 hr*ng/mL. For solid dispersion A, the $C_{max}$=6820 ng/mL, and $AUC_{0-72\ hr}$ is 105635 hr*ng/mL. For solid dispersion B, the $C_{max}$ is 30467 ng/mL; $AUC_{0-72\ hr}$ is 406841 hr*ng/mL.

The $AUC_{0-72\ hr}$ ratio of Solid Dispersion B to Form 2 is 19. The $AUC_{0-72\ hr}$ ratio of Solid Dispersion A to Form 2 is 5.

Example 5. Phase 1 Clinical Trial Protocol

The safety, PK/PD, and clinical activity evaluation of Compound 1, or a pharmaceutically acceptable salt thereof, is evaluated in subjects with advanced hematologic malignancies, such as AML, MDS, MPN, or CMML), that harbor an IDH1 mutation. Primary study objectives include 1) assessment of the safety and tolerability of treatment with Compound 1, or a pharmaceutically acceptable salt thereof when administered continuously as a single agent dosed orally twice daily (approximately every 12 hours) on Days 1 to 28 of a 28-day cycle, and 2) determination of the maximum tolerated dose (MTD) and/or the recommended Phase 2 dose of Compound 1, or a pharmaceutically acceptable salt thereof in subjects.

Secondary study objectives include 1) description of the dose-limiting toxicities (DLTs) of Compound 1, or a pharmaceutically acceptable salt thereof in subjects with advanced hematologic malignancies, such as AML, MDS, MPN, or CMML, that harbor an IDH1 mutation, characterization of the pharmacokinetics (PK) of Compound 1, or a pharmaceutically acceptable salt thereof in subjects with advanced hematologic malignancies, such as AML, MDS, MPN, or CMML, that harbor an IDH1 mutation, 3) evaluation of the PK/pharmacodynamic (PD) relationship of Compound 1, or a pharmaceutically acceptable salt thereof, and 2-hydroxygluturate (2HG), and 4) characterization of the clinical activity associated with Compound 1, or a pharmaceutically acceptable salt thereof, in subjects with advanced hematologic malignancies, such as AML, MDS, MPN, or CMML, that harbor an IDH1 mutation.

Exploratory study objectives include 1) evaluation of changes in Ki67 levels in tumor samples, 2) characterization of the PD effects of Compound 1, or a pharmaceutically acceptable salt thereof, in subjects with advanced hematologic malignancies, such as AML, MDS, MPN, or CMML, that harbor an IDH1 mutation by the assessment of changes in the patterns of cellular differentiation of isocitrate dehydrogenase-1 (IDH1)-mutated tumor cells and changes in histone and deoxyribonucleic acid (DNA) methylation profiles in IDH1-mutated tumor cells, 3) evaluation of gene mutation status, global gene expression profiles, and other potential prognostic markers (cytogenetics) in IDH1-mutated tumor cells, as well as subclonal populations of non-IDH1 mutated tumor cells, to explore predictors of anti-tumor activity and/or resistance, and 4) monitoring plasma cholesterol and 4β-OH-cholesterol levels as a potential CYP3A4 induction marker.

Compound 1 will be administered orally twice daily (approximately every 12 hours) on Days 1 to 28 in 28-day cycles. If warranted based on the emerging data, an alternative dosing schedule (e.g., once daily or three times daily), including administration of the same total daily dose using different dosing schedules in concurrent cohorts, may be explored. Starting with C1D1, dosing is continuous; there are no inter-cycle rest periods.

Subjects who do not meet any of the standard clinical treatment withdrawal criteria may continue treatment beyond Cycle 1.

Subjects will be dispensed the appropriate number of tablets for 28 days of dosing (plus an additional 2-day supply to allow for scheduling of visits) on Day 1 of each cycle. Subjects are to return all unused tablets (or the empty bottles) on Day 1 of each treatment cycle. Subjects will be given a dosing diary for each treatment cycle. They should record relevant information regarding their study drug in the diary (e.g., confirmation that each daily dose was taken, reasons for missed doses). Treatment compliance will be assessed based on return of unused drug and the dosing diary.

Subjects should be instructed to take their daily dose at approximately the same time each day. Each dose should be taken with a glass of water and consumed over as short a time as possible. Subjects should be instructed to swallow tablets whole and to not chew the tablets. Subjects may take Compound 1, or a pharmaceutically acceptable salt thereof with or without food. If the subject forgets to take the daily morning (or evening) dose, then they should take Compound 1, or a pharmaceutically acceptable salt thereof within 6 hours after the missed dose. If more than 6 hours have elapsed, then that dose should be omitted, and the subject should resume treatment with the next scheduled dose.

The study includes a dose escalation phase to determine MTD followed by expansion cohorts to further evaluate the safety and tolerability of the MTD. The dose escalation phase will utilize a standard "3+3" design. During the dose escalation phase, consented eligible subjects will be enrolled into sequential cohorts of increasing doses of Compound 1, or a pharmaceutically acceptable salt thereof. Each dose cohort will plan to enroll a minimum of 3 subjects. The first 3 subjects enrolled in each dosing cohort during the dose escalation phase of the study will initially receive a single dose of study drug on Day −3 (i.e., 3 days prior to the start of daily dosing) and undergo PK/PD assessments over 72 hours to evaluate drug concentrations and 2HG levels. The next dose of study drug will be on Cycle 1 Day 1 (C1D1) at which time daily dosing will begin. The initial dosing regimen will be twice daily (approximately every 12 hours). If warranted based on the emerging data, an alternative dosing schedule (e.g., once daily or three times daily), including administration of the same total daily dose using different dosing schedules in concurrent cohorts, may be explored. If there are multiple subjects in the screening process at the time the third subject within a cohort begins treatment, up to 2 additional subjects may be enrolled with approval of the Medical Monitor. For these additional subjects, the Day −3 through Day 1 PK/PD assessments are optional following discussion with the Medical Monitor. The planned dose escalation scheme is illustrated in Table 1.

TABLE 1

Dose Escalation Scheme

| Cohort Level | Compound 1 Dose[1] | Number of Subjects |
|---|---|---|
| −1 | 50 mg[2] | 3 to 6 |
| 1 (Starting Dose) | 100 mg | 3 to 6 |
| 2 | 200 mg | 3 to 6 |
| 3 | 400 mg | 3 to 6 |
| 4, etc. | 800 mg[3] | 3 to 6 |
| Expansion | MTD[4] | 36[5] |

[1]Compound 1, or a pharmaceutically acceptable salt thereof, may be administered twice daily (approximately every 12 hours). If warranted based on the emerging data, an alternative dosing schedule (e.g., once daily or three times daily), including administration of the same total daily dose using different dosing schedules in concurrent cohorts, may be explored.
[2]If DLTs (are observed at Dose Level 1 (100 mg), the dose for the second cohort will be decreased to 50 mg (Dose Level −1).
[3]Continued doubling of the dose until Compound 1-related NCI CTCAE version 4.03 ≥Grade 2 toxicity is observed. Following evaluation of the event(s) by the Clinical Study Team, subsequent increases in dose will be guided by the observed toxicity, and potentially PK and PK/PD data until MTD is determined. The absolute percent increase in the dose will be determined by the Clinical Study Team predicated on the type and severity of any toxicity seen in the prior dose cohorts. Dose escalation will never exceed 100%.
[4]Defined as the highest dose that causes DLTs in <1 of 3 or <2 of 6 subjects. If no DLTs are identified, dosing will continue for at least 2 dose levels above the projected maximum biologically effective exposure, as determined by an ongoing assessment of PK/PD and any observed clinical activity to determine the recommended Phase 2 dose.
[5]To include 3 cohorts of approximately 12 subjects each.

Toxicity severity will be graded according to the National Cancer Institute Common Terminology Criteria for Adverse Events (NCI CTCAE) version 4.03. A DLT is defined as follows. Hematologic includes prolonged myelosuppression, defined as persistence of ≥3 Grade neutropenia or thrombocytopenia (by NCI CTCAE, version 4.03, leukemia-specific criteria, i.e., marrow cellularity <5% on Day 28 or later from the start of study drug without evidence of leukemia) at least 42 days after the initiation of Cycle 1 therapy. Leukemia-specific grading should be used for cytopenias (based on percentage decrease from baseline: 50 to 75%=Grade 3, >75%=Grade 4). All AEs that cannot clearly be determined to be unrelated to Compound 1, or a pharmaceutically acceptable salt thereof will be considered relevant to determining DLTs.

If, after the third subject completes the 28-day DLT evaluation period (i.e., Cycle 1), no DLTs are observed, the study will proceed with dose escalation to the next cohort following safety review by the Clinical Study Team. If 1 of 3 subjects experiences a DLT during the first cycle, 3 additional subjects will be enrolled in that cohort. If none of the additional 3 subjects experience a DLT, dose escalation may continue to the next cohort following safety review. If 2 or more subjects in a cohort experience DLTs during the first cycle, dose escalation will be halted and the next lower dose level will be declared the MTD. Alternatively, a dose level intermediate between the dose level exceeding MTD and the previous does level may be explored and declared MTD if <2 out of 6 patients experience a DLT at that dose. If the MTD cohort includes only 3 subjects, an additional 3 subjects will be enrolled at that dose level to confirm that <2 of 6 subjects experience a DLT at that dose.

Increases in the dose of Compound 1, or a pharmaceutically acceptable salt thereof, for each dose cohort will be guided by an accelerated titration design, where the dose will be doubled (100% increase) from one cohort to the next until Compound 1-related NCI CTCAE version 4.03 Grade 2 or greater toxicity is observed in any subject within the cohort. Subsequent increases in dose will be guided by the observed toxicity, and potentially PK and PK/PD data, until the MTD is determined. The absolute percent increase in the daily dose will be determined predicated on the type and severity of any toxicity seen in the prior dose cohorts (but will never exceed 100%). If warranted based on the emerging data, an alternative dosing schedule (e.g., once daily or three times daily) may be explored, including administration of the same total daily dose using different dosing schedules in concurrent cohorts. The MTD is the highest dose that causes DLTs in <2 of 6 subjects.

If no DLTs are identified during the dose escalation phase, dose escalation may continue for 2 dose levels above the projected maximum biologically effective dose, as determined by an ongoing assessment of PK/PD and any observed clinical activity, to determine the recommended Phase 2 dose.

To optimize the number of subjects treated at a potentially clinically relevant dose, intra-subject dose escalation will be permitted Following determination of the recommended Phase 2 dose, 3 or more expansion cohorts (with AML, MDS, MPN, or CMML) of approximately 12 subjects each will be treated at that dose. The purpose of the expansion cohorts is to evaluate and confirm the safety and tolerability of the recommended Phase 2 dose in specific disease indications. Subjects enrolled in these cohorts will undergo the same procedures as subjects in the dose escalation cohorts with the exception that the Day −3 through Day 1 PK/PD assessments will be optional.

Subjects will undergo screening procedures within 28 days prior to the start of study drug treatment to determine eligibility. Screening procedures include medical, surgical, and medication history, confirmation of IDH1 mutation via tumor biopsies or leukemic blasts (if not documented previously), physical examination, vital signs, Eastern Cooperative Oncology Group (ECOG) performance status (PS), 12-lead electrocardiogram (ECG), evaluation of left ventricular ejection fraction (LVEF), clinical laboratory assessments (hematology, chemistry, coagulation, urinalysis, and serum pregnancy test), bone marrow biopsy and aspirate, and blood and urine samples for 2HG measurement; and blood samples for determination of plasma cholesterol and 4β-OH-cholesterol levels.

Three days prior to starting the twice daily dosing of Compound 1, or a pharmaceutically acceptable salt thereof (Day −3), the first 3 subjects enrolled in each cohort in the dose escalation phase will receive a single dose of Compound 1, or a pharmaceutically acceptable salt thereof in clinic and have serial blood and urine samples obtained for determination of blood and urine concentrations of Compound 1, or a pharmaceutically acceptable salt thereof, its metabolite, and 2HG. A full 72-hour PK/PD profile will be conducted: subjects will be required to remain at the study site for 10 hours on Day −3 and return on Days −2, −1, and 1 for 24, 48, and 72 hour samples, respectively.

Daily treatment with Compound 1, or a pharmaceutically acceptable salt thereof, will begin on C1D1; subjects who did not undergo the Day −3 PK/PD assessments will be observed in the clinic for 4 hours following the C1D1 dose. The initial dosing regimen will be twice daily (approximately every 12 hours). Safety assessments conducted during the treatment period include physical examination, vital signs, ECOG PS, 12-lead ECGs, LVEF, and clinical laboratory assessments (hematology, chemistry, coagulation, and urinalysis).

All subjects will undergo PK/PD assessments over a 10-hour period on both C1D15 and C2D1. Additional pre-dose urine and/or blood sampling will be conducted on C1D8, C1D22, C2D15, C3D1, C3D15, and on Day 1 of all subsequent cycles. Available bone marrow biopsy samples also will be assessed for 2HG levels.

Subjects will undergo radiographic evaluations (CT/MRI), and assessment of bone marrow aspirates and biopsies and peripheral blood to assess the extent of disease, at screening, on Day 15, Day 29 and Day 57, and every 56 days thereafter while on study drug treatment, independent of dose delays and/or dose interruptions, and/or at any time when progression of disease is suspected. Two core tumor biopsies will be obtained at screening, at the time of the first assessment of response, and at the time of disease progression within a window of ±3 days around the planned assessment time point. For patients with acute myelogenous leukemia (AML), response to treatment will be determined by the Investigators based on modified International Working Group (IWG) response criteria.

Subjects may continue treatment with Compound 1, or a pharmaceutically acceptable salt thereof until disease progression, occurrence of a DLT, or development of other unacceptable toxicity. All subjects are to undergo an end of treatment assessment (within approximately 5 days of the last dose of study drug); in addition, a follow-up assessment is to be scheduled 28 days after the last dose.

It is estimated that approximately 51 subjects will be enrolled in the study. Assuming that identification of the MTD requires the evaluation of 4 dose levels of Compound 1, or a pharmaceutically acceptable salt thereof with only 3 subjects per dose level, with the exception that the MTD requires 6 subjects, then 15 subjects will be enrolled during the dose escalation part of the study. Three cohorts of approximately 12 additional subjects each in specific advanced hematologic malignancies (total 36 subjects) will be enrolled in the cohort expansion part of the study. Additional subjects may be needed for cohort expansion during dose escalation, for the replacement of non-evaluable subjects, or for evaluation of alternative dosing regimens other than the planned escalation scheme or the MTD, to optimize the recommended Phase 2 dose.

A patient must meet all of the following inclusion criteria to be enrolled in the clinical study. 1) Subject must be ≥18 years of age; 2) Subjects must have a) an advanced hematologic malignancy including: i) Relapsed and/or primary refractory AML as defined by World Health Organization (WHO) criteria, ii) untreated AML, ≥60 years of age and are not candidates for standard therapy due to age, performance status, and/or adverse risk factors, according to the treating physician and with approval of the Medical Monitor, iii) Myelodysplastic syndrome with refractory anemia with excess blasts (subtype RAEB-1 or RAEB-2), or considered high-risk by the Revised International Prognostic Scoring System (IPSS-R) (Greenberg et al. *Blood.* 2012; 120(12): 2454-65) that is recurrent or refractory, or the patient is intolerant to established therapy known to provide clinical benefit for their condition (i.e., patients must not be candidates for regimens known to provide clinical benefit), according to the treating physician and with approval of the Medical Monitor, and iv) Subjects with other relapsed and/or primary refractory hematologic cancers, for example CMML, who fulfill the inclusion/excluding criteria may be considered on a case-by case basis; 3) subjects must have documented IDH1 gene-mutated disease based on local evaluation. Analysis of leukemic blast cells for IDH1 gene mutation is to be evaluated at screening (if not evaluated previously) by the site's local laboratory to determine subject eligibility for the study. If the site does not have local laboratory access for IDH1 gene mutation analysis, central laboratory evaluation is acceptable. A pretreatment tumor sample (from blood and/or bone marrow) will be required for all screened subjects for central laboratory biomarker analysis. Gene mutation analysis of a tumor sample (from blood or bone marrow) is to be repeated at the End of Treatment visit and submitted to the central laboratory for biomarker analysis; 4) Subjects must be amenable to serial bone marrow biopsies, peripheral blood sampling, and urine sampling during the study. (The diagnosis and evaluation of AML or MDS can be made by bone marrow aspiration when a core biopsy is unobtainable and/or is not a part of the standard of care. A bone marrow biopsy is required in case of dry tap or failure (mainly dilution) with the aspiration); 5) Subjects or their legal representatives must be able to understand and sign an informed consent; 6) subjects must have ECOG PS of 0 to 2; 7) subjects must have a platelet count ≥20,000/μL (Transfusions to achieve this level are allowed.) Subjects with a baseline platelet count of <20,000/μL due to underlying malignancy are eligible with Medical Monitor approval; 8) Subjects must have adequate hepatic function as evidenced by: a) Serum total bilirubin ≤1.5× upper limit of normal (ULN), unless considered due to Gilbert's disease or leukemic organ involvement, and b) Aspartate aminotransferase, ALT, and alkaline phosphatase (ALP) ≤3.0×ULN, unless considered due to leukemic organ involvement; 9) Subjects must have adequate renal function as evidenced by a serum creatinine ≤2.0×ULN or Creatinine clearance >40 mL/min based on the Cockroft-Gault glomerular filtration rate (GFR) estimation: (140−Age)×(weight in kg)×(0.85 if female)/72×serum creatinine; 10) Subjects must be recovered from any clinically relevant toxic effects of any prior surgery, radiotherapy, or other therapy intended for the treatment of cancer. (Subjects with residual Grade 1 toxicity, for example Grade 1 peripheral neuropathy or residual alopecia, are allowed with approval of the Medical Monitor); and 11) Female subjects with reproductive potential must have a negative serum pregnancy test within 7 days prior to the start of therapy. Subjects with reproductive potential are defined as one who is biologically capable of becoming pregnant. Women of childbearing potential as well as fertile men and their partners must agree to abstain from sexual intercourse or to use an effective form of contraception during the study and for 90 days (females and males) following the last dose of Compound 1, or a pharmaceutically acceptable salt thereof.

Compound 1, or a pharmaceutically acceptable salt thereof, will be provided as 50 and 200 mg strength tablets to be administered orally, twice daily or once daily.

The first 3 subjects in each cohort in the dose escalation portion of the study will receive a single dose of study drug on Day −3; their next dose of study drug will be administered on C1D1 at which time subjects will start dosing twice daily (approximately every 12 hours) on Days 1 to 28 in 28-day cycles. Starting with C1D1, dosing is continuous; there are no inter-cycle rest periods. Subjects who are not required to undergo the Day −3 PK/PD assessments will initiate twice daily dosing (approximately every 12 hours) with Compound 1, or a pharmaceutically acceptable salt thereof on C1D1.

The dose of Compound 1, or a pharmaceutically acceptable salt thereof administered to a subject will be dependent upon which dose cohort is open for enrollment when the subject qualifies for the study. The starting dose of Compound 1, or a pharmaceutically acceptable salt thereof to be administered to the first cohort of subjects is 100 mg strength administered orally twice a day (200 mg/day).

Subjects may continue treatment with Compound 1, or a pharmaceutically acceptable salt thereof until disease progression, occurrence of a DLT, or development of other unacceptable toxicity.

Criteria for Evaluation
Safety:

AEs, including determination of DLTs, serious adverse events (SAEs), and AEs leading to discontinuation; safety laboratory parameters; physical examination findings; vital signs; 12-lead ECGs; LVEF; and ECOG PS will be monitored during the clinical study. The severity of AEs will be assessed by the NCI CTCAE, Version 4.03.

Compound 1, or a pharmaceutically acceptable salt thereof, may cause sensitivity to direct and indirect sunlight. The subjects should be warned to avoid direct sun exposure. When exposure to sunlight is anticipated for longer than 15 minutes, the subject should be instructed to apply factor 30 or higher sunscreen to exposed areas and wear protective clothing and sunglasses.

Pharmacokinetics and Pharmacodynamics:

Serial blood samples will be evaluated for determination of concentration-time profiles of Compound 1, or a pharmaceutically acceptable salt thereof. Urine samples will be evaluated for determination of urinary excretion of Compound 1, or a pharmaceutically acceptable salt thereof. Blood, bone marrow, and urine samples will be evaluated for determination of 2HG levels. Tumor biopsies will be taken for evaluation of 2HG and Compound 1, or a pharmaceutically acceptable salt thereof.

Pharmacokinetic Assessments:

Serial blood samples will be drawn before and after dosing with Compound 1, or a pharmaceutically acceptable salt thereof in order to determine circulating plasma concentrations of Compound 1, or a pharmaceutically acceptable salt thereof. The blood samples will also be used for the determination of 2HG concentrations and for evaluation of cholesterol and 4β-OH-cholesterol levels.

For the first 3 subjects enrolled in a cohort during the dose escalation phase, a single dose of Compound 1, or a pharmaceutically acceptable salt thereof will be administered on Day −3 (i.e., 3 days prior to their scheduled C1D1 dose). Blood samples will be drawn prior to the single-dose administration of Compound 1, or a pharmaceutically acceptable salt thereof and at the following time points after administration: 30 minutes and 1, 2, 3, 4, 6, 8, 10, 24, 48, and 72 hours. After 72 hours of blood sample collection, subjects will begin oral twice daily dosing of Compound 1, or a pharmaceutically acceptable salt thereof (i.e., C1D1). The PK/PD profile from Day −3 through Day 1 is optional for additional subjects enrolled in the dose escalation phase (i.e., for any subjects beyond the 3 initial subjects enrolled in a cohort) and is not required for subjects enrolled in the expansion cohorts.

All subjects will undergo 10-hour PK/PD sampling on C1D15 and C2D1 (i.e., on Days 15 and 29 of twice daily dosing). For this profile, one blood sample will be drawn immediately prior to that day's first dose of Compound 1, or a pharmaceutically acceptable salt thereof (i.e., dosing with Compound 1, or a pharmaceutically acceptable salt thereof will occur at the clinical site); subsequent blood samples will be drawn at the following time points after dosing: 30 minutes, and 1, 2, 3, 4, 6, 8, and 10 hours. Blood samples also will be drawn on Days 8 and 22 of Cycle 1, Day 15 of Cycle 2, Days 1 and 15 of Cycle 3, and Day 1 of each cycle thereafter; all samples will be obtained prior to dosing. Additionally, one blood sample will be drawn at the End of Treatment Visit.

The timing of blood samples drawn for Compound 1, or a pharmaceutically acceptable salt thereof concentration determination may be changed if the emerging data indicates that an alteration in the sampling scheme is needed to better characterize the PK profile of Compound 1, or a pharmaceutically acceptable salt thereof.

Pharmakodynamic Assessments:

Serial blood samples will be drawn before and after dosing with Compound 1, or a pharmaceutically acceptable salt thereof in order to determine circulating concentrations of 2HG. Samples collected for PK assessments also will be used to assess 2HG levels. In addition, subjects will have blood drawn for determination of 2HG levels at the screening assessment.

The timing of blood samples drawn for 2HG concentration determination may be changed if the emerging data indicate that an alteration in the sampling scheme is needed to better characterize the 2HG response to Compound 1, or a pharmaceutically acceptable salt thereof, treatment.

Urine will be collected for the determination of concentrations of 2HG levels at the screening assessment and prior to dosing on Day 15 of Cycle 1 and on Day 1 of Cycle 2 and every cycle thereafter. At least 20 mL of urine will be collected for each sample.

The volume of each collection will be measured and recorded and sent to a central laboratory for determination of urinary 2HG concentration. An aliquot from each collection will be analyzed for urinary creatinine concentration.

Tumor biopsy specimens will be collected and assessed for 2HG levels, at the screening assessment, at the time of the first disease assessment, and at any time disease progression is suspected. A window of ±3 days around the planned assessment time point is acceptable for all biopsy samples. Tumor biopsies are to be evaluated for morphology and for cellular differentiation via hematoxylin and eosin (H & E) staining and ICH for specific cell-type markers. Tumor samples may also be evaluated for 2HG levels, Ki67 levels, and, if feasible, intra-tumoral Compound 1, or a pharmaceutically acceptable salt thereof, levels.

Serial blood samples will be drawn to obtain plasma cholesterol and 4β-OH-cholesterol levels as a potential CYP3A4 induction marker. Samples are obtained on Day −3 (within 30 minutes), at 24, 48, and 72 hours (±1 hour), and on Days 8, 15 and 22 of Cycle 1, Days 1 and 15 of Cycles 2 and 3, and Day 1 of every cycle thereafter.

Clinical Activity:

Serial blood and bone marrow biopsies will be evaluated during the clinical study to determine response to Compound 1, or a pharmaceutically acceptable salt thereof treatment according to the 2006 modified IWG criteria for hematologic malignancies, such as MDS, MDS, MPN or AML (Cheson B D, et al. *Blood.* 2006; 108(2):419-25).

Disease response to treatment will be assessed through the evaluation of bone marrow biopsies and/or aspirates, along with complete blood counts and examination of peripheral blood films. Subjects will have the extent of their disease assessed and recorded at screening, on Days 15, 29, and 57, every 56 days thereafter while on study drug treatment, independent of dose-delays and/or dose interruptions, and/or at any time when progression of disease is suspected. An assessment also will be conducted at the End of Treatment visit for subjects who discontinue the study due to reasons other than disease progression.

Statistical Analysis

Statistical analyses will be primarily descriptive in nature since the goal of the study is to determine the MTD of Compound 1, or a pharmaceutically acceptable salt thereof. Tabulations will be produced for appropriate disposition, demographic, baseline, safety, PK, PD, and clinical activity parameters and will be presented by dose level and overall. Categorical variables will be summarized by frequency distributions (number and percentages of subjects) and continuous variables will be summarized by descriptive statistics (mean, standard deviation, median, minimum, and maximum).

Adverse events will be summarized by Medical Dictionary for Regulatory Activities (MedDRA) system organ class and preferred term. Separate tabulations will be produced for all treatment-emergent AEs (TEAEs), treatment-related AEs (those considered by the Investigator as at least possibly drug related), SAEs, discontinuations due to AEs, and AEs of at least Grade 3 severity. By-subject listings will be provided for deaths, SAEs, DLTs, and AEs leading to discontinuation of treatment.

Descriptive statistics will be provided for clinical laboratory, ECG interval, LVEF, and vital signs data, presented as both actual values and changes from baseline relative to each on-study evaluation and to the last evaluation on study. Shift analyses will be conducted for laboratory parameters and ECOG PS.

Descriptive statistics will be used to summarize PK parameters for each dose group and, where appropriate, for the entire population. The potential relationship between plasma levels of Compound 1, or a pharmaceutically acceptable salt thereof and blood, plasma or urine 2HG levels will be explored with descriptive and graphical methods.

Response to treatment as assessed by the site Investigators using modified IWG (for subjects with hematologic malignancies, such as MDS, MDS/MPN or AML). Two-sided 90% confidence intervals on the response rates will be calculated for each dose level and overall. Data will also be summarized by type of malignancy for subjects in the cohort expansion phase. Descriptive statistics will be used to summarize Ki67 levels from tumor biopsies.

Study Results

Figure 7A:
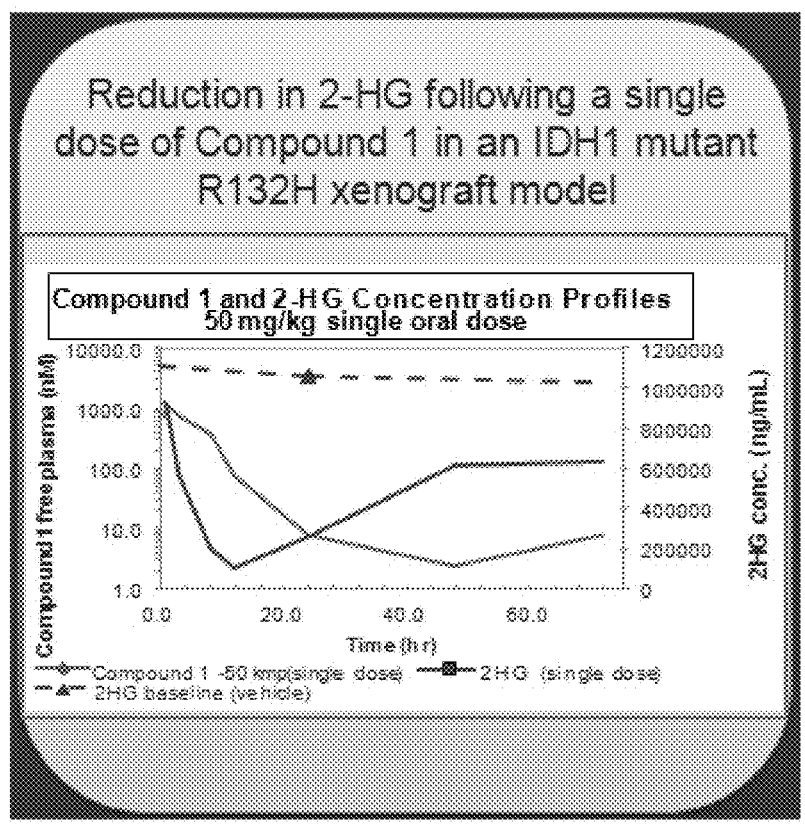
FIG. 7A depicts a line graph showing reduction in 2HG following a single dose (50 mg/kg) of a compound (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1) in an IDH1 mutant R132H xenograft model.
Figure 7B:
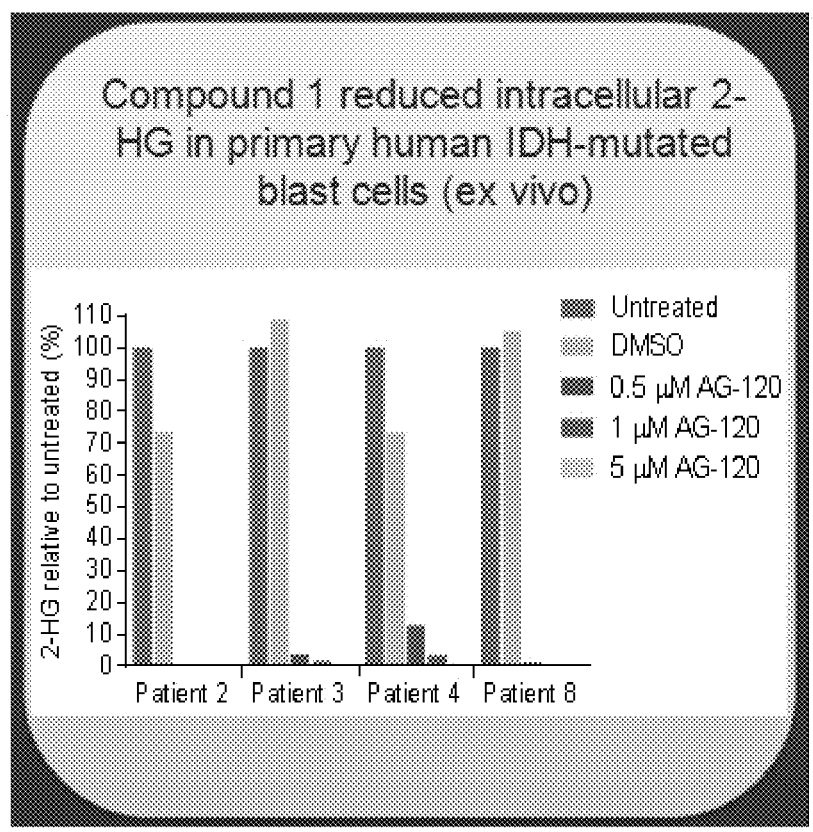
FIG. 7B depicts a bar graph showing Compound 1 (at 0.5 uM, 1 uM and 5 uM concentrations) reduced intracellular 2HG in primary human IDH-mutated blast cells (ex vivo).

Compound 1 had a cellular $IC_{50}$ value of 8-20 nM. Reduction in 2HG was observed following a single dose of Compound 1 in an IDH1 mutant R132H xenograft model (FIG. 7A). In addition, Compound 1 reduced intracellular 2HG in primary human IDH-mutated blast cells ex vivo (FIG. 7B).

TABLE 2

| | Cohort 1 100 mg BID* (n = 4) | Cohort 2 300 mg QD* (n = 4) | Cohort 3 500 mg QD (n = 4) | Cohort 4 800 mg QD (n = 5) | All patients (N = 17) |
|---|---|---|---|---|---|
| On therapy, n | 1 | 2 | 3 | 5 | 11 |
| Discontinued, n | 3 | 2 | 1 | — | 6 |
| due to PD* | 2 | 1 | 1 | — | 4 |
| due to AE* | 1** | — | — | — | 1** |
| due to Investigator Decision | — | 1 | — | — | 1 |
| Death ≤28 days after Compound 1 Discontinuation | 3 | 2 | 1 | — | 6 |

*AE, adverse event; PD, progressive disease; BID, twice daily; QD, once daily
**AE = intracranial hemorrhage. This patient presented with right extremity weakness (upper and lower). The patient was hospitalized with a platelet count of 11 on admission. The patient's status quickly deteriorated, a CT scan revealed left sided intraparenchymal hemorrhage.

The patient died 3 days later.

Patients in Table 2 have received median (range)=1.6 (0.4-5.7) of months of treatment.

TABLE 3

Demographic Characteristics of Patients of Table 2

| | All treated patients (N = 17) |
|---|---|
| Age in years, median (range) | 73 (42-87) |
| Men/women, n | 8/9 |
| Diagnosis, n | |
| R/R AML | 17 |
| ECOG performance status, n | |
| 0 | 6 |
| 1 | 9 |
| 2 | 2 |
| Number of prior chemotherapy regimens, median (range) | 2 (1-5) |
| Prior BMT, n | 2 |
| Abnormal cytogenetics, n | 10 |

One DLT (dose limiting toxicity) of grade 3 QT prolongation at 800 mg QD was observed. There were no associated cardiac symptoms, QTc returned to normal following 3-day drug hold. The patient's dose was reduced to 500 mg QD and remains on study with grade 1 QTc prolongation in complete remission (CR). Eight subjects experienced serious adverse events. At 100 mg BID, 1 subject discontinued study due to an intracranial bleed attributed to disease progression and resulted in death. At 300 mg QD, 1 subject experienced differentiation syndrome, recovered and was in CR. At 800 mg QD, 1 subject experienced tongue edema and QT prolongation (DLT described above), recovered and was in CR. All other SAEs related to disease progression resulted in death. For the patient that experienced differentiation syndrome, symptoms included fever and dyspnea. The patient was treated with steroids. Two events that led to PD are described as they are events that correlate to discontinuations due to AEs.

TABLE 4

Adverse Events
Notable grade ≥3 AEs include: hypotension 2 (12%), mental status changes 2 (12%), neutropenia 2 (12%). AEs appear typical for this patient population. Other QT prolongations observed: Grade 1 prolonged QT in 100 mg cohort (the patient had a history of right bundle branch block (R BBB) at study entry; Grade 1 intermittent prolonged QT in 300 mg cohort; and Grade 3 prolonged QT (DLT) in 800 mg cohort.

| AE | Grade ≥3, n (%) | All grades, n (%) |
|---|---|---|
| At least 1 adverse event | 11 (65) | 14 (82) |
| Nausea | 1 (6) | 5 (29) |
| Fatigue | 1 (6) | 5 (29) |
| Dyspnea | 2 (12) | 5 (29) |
| Vomiting | 0 | 4 (24) |
| Pyrexia | 1 (6) | 4 (24) |
| Cough | 0 | 4 (24) |
| Febrile neutropenia | 3 (18) | 3 (18) |
| Diarrhea | 0 | 3 (18) |
| Electrocardiogram QT prolonged | 1 (6) | 3 (18) |

Compound 1 Exposure and 2HG Inhibition

Figure 8A:
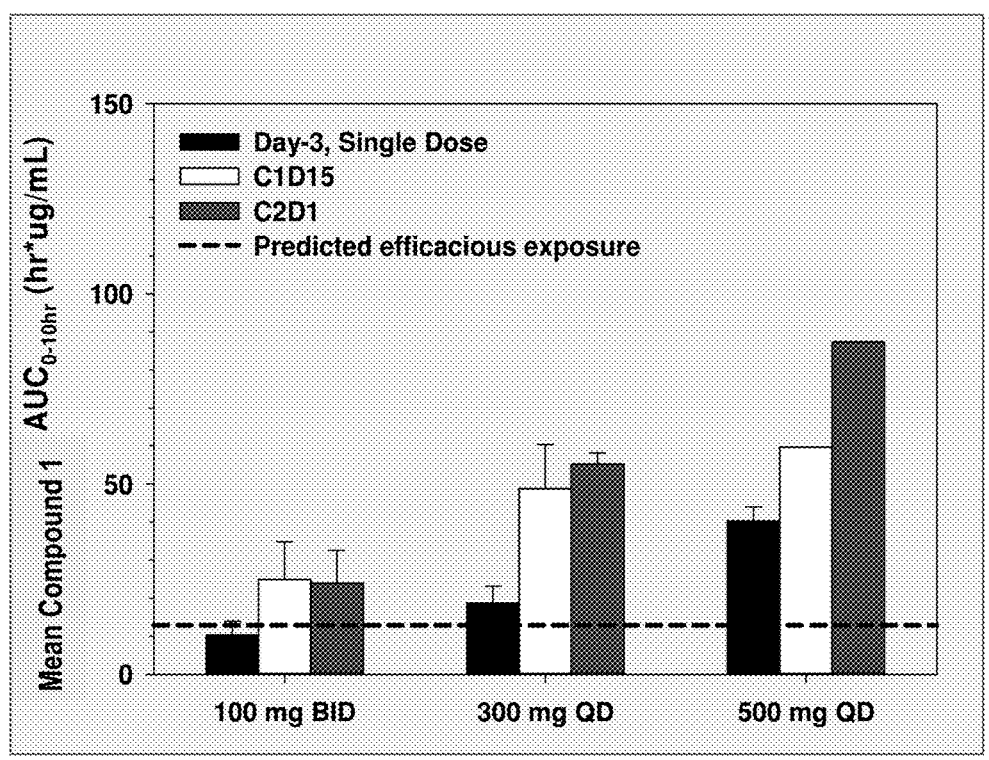
FIG. 8A depicts a bar graph showing the PK profile following oral administration of Compound 1 in patients treated at day −3 with a single dose, at day 15 of cycle 1, and at day 1 of cycle 2, each at doses of 100 mg BID, 300 mg QD or 500 mg QD.
Figure 8B:
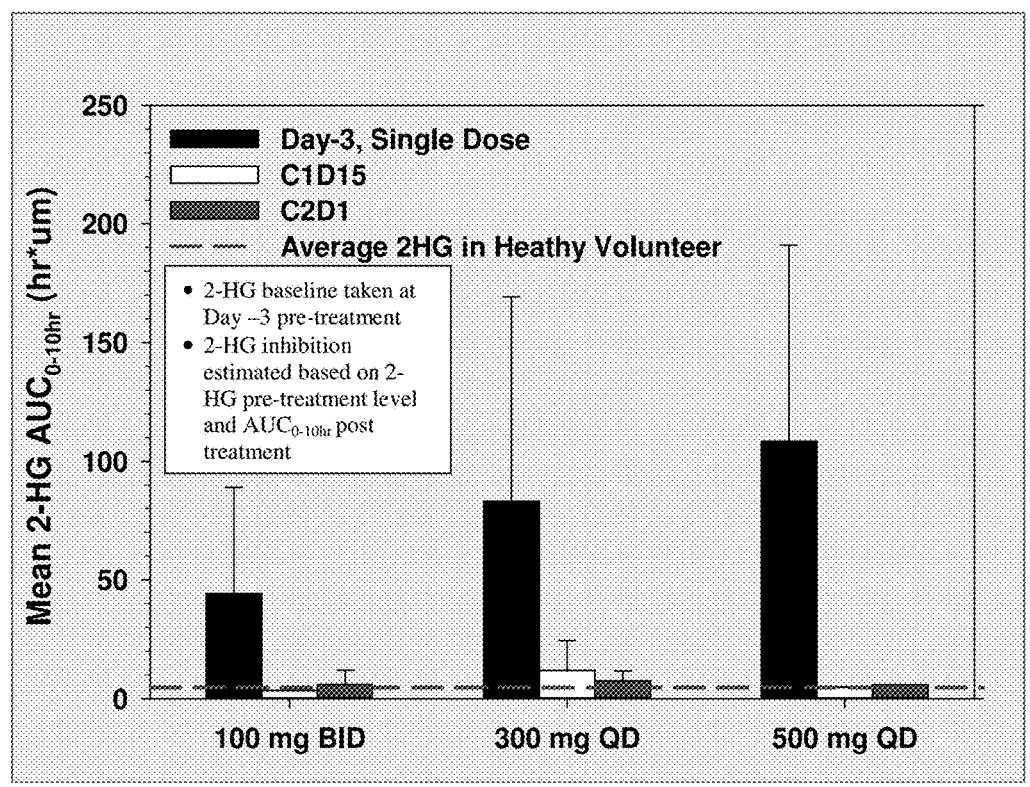
FIG. 8B depicts a bar graph showing that plasma concentrations of 2HG were reduced to normal ranges at day −3 with a single dose, at day 15 of cycle 1, and at day 1 of cycle 2, each at doses of 100 mg BID, 300 mg QD or 500 mg QD.

FIGS. 8A and 8B shows the PK profile of Compound 1 following oral administration. Compound 1 showed high plasma exposure, drug accumulation and half-life of 182 hours. The plasma levels of 2HG were reduced to a normal range at all dose levels (up to 98% inhibition). The 2HG baseline was taken at Day −3 pre-treatment 2HG inhibition estimated based on 2HG pre-treatment level and $AUC_{0-10\ hr}$ post treatment. For the 100 mg BID and 300 mg QD Cohorts, 3 to 4 patients were measured per time point and for the 500 mg QD Cohort, 1 to 3 patients were measured per time point.

TABLE 5

Clinical Activity Assessed by Investigator Using IWG AML and MDS Criteria

| | Cohort 1 100 mg BID (n = 4) | Cohort 2 300 mg QD (n = 4) | Cohort 3 500 mg QD (n = 4) | Cohort 4 800 mg QD (n = 2) | Total N = 14 |
|---|---|---|---|---|---|
| CR | 1 | 1 | 1 | 1 | 4 |
| Marrow CR | — | — | 2 | — | 2 |
| PR | — | — | — | 1 | 1 |
| SD | 3 | 2 | 1 | — | 6 |
| PD | — | 1 | — | — | 1 |
| Overall response rate (ORR) | 1/4 | 1/4 | 3/4 | 2/2 | 7/14 |

Figure 9A:
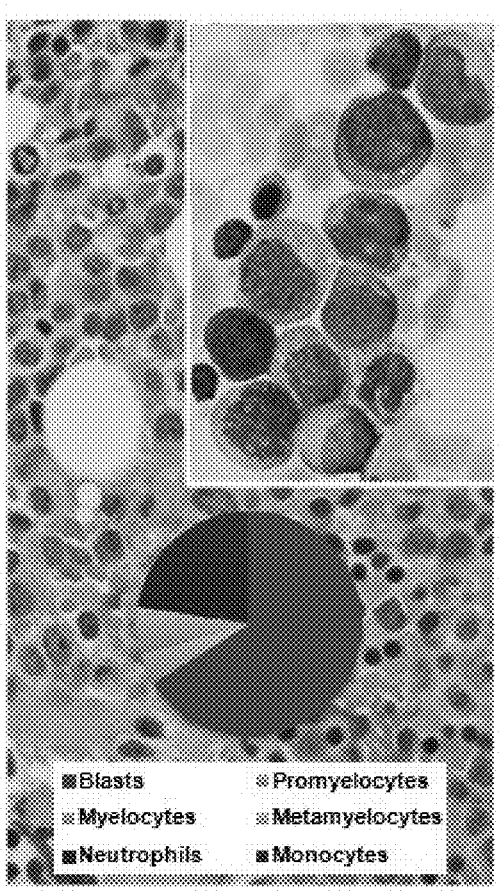
FIGS. 9A, 9B and 9C depict images of bone marrow aspirate showing blasts, myelocytes, neutrophils, promyelocytes, metamyelocytes and monocytes, in a patient at baseline, e.g., untreated, after cycle 1, day 15 and cycle 1, day 28, respectively.
Figure 9B:
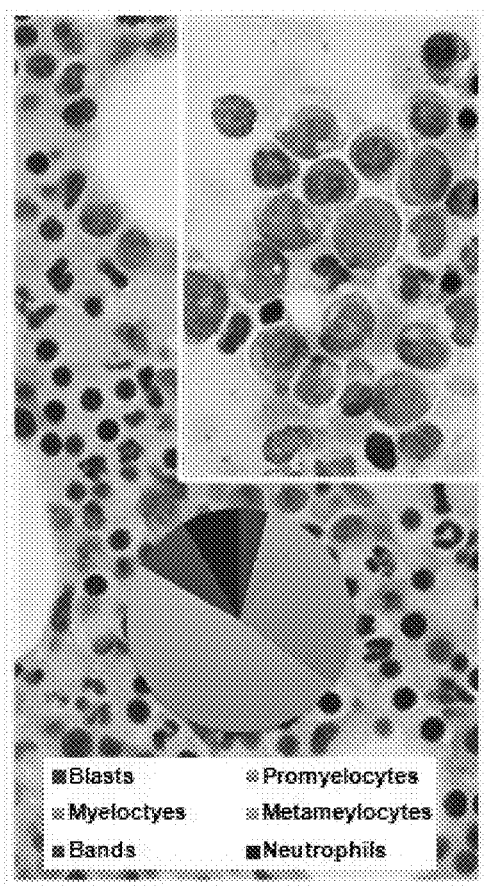
Figure 9C:
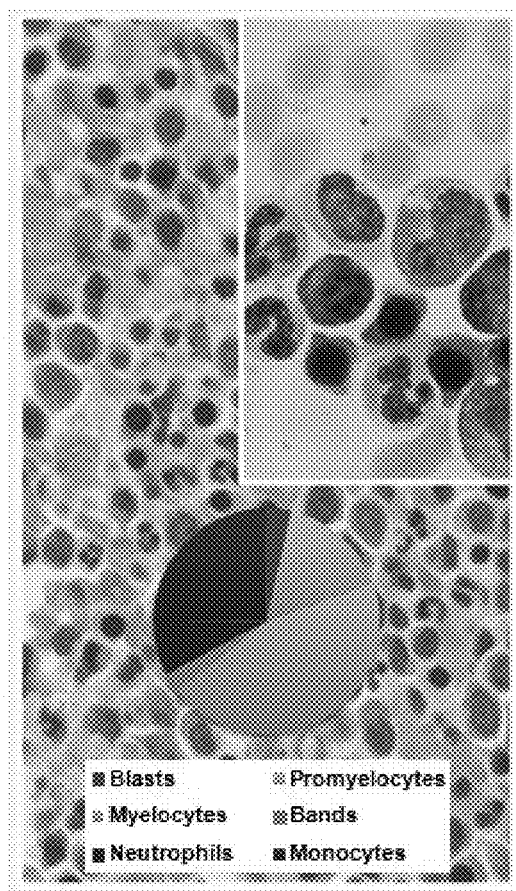

CR = complete response
Marrow CR = ≤5% blasts in BM; no hematological recovery
PR = partial response
SD = stable disease
PD = progressive disease
ORR = CR, Marrow CR and PR Differentiation Effect in the Bone Marrow FIGS. 9A-9C are images of aspirate from a 74 year old female patient who was refractory to induction with 7+3. At baseline (FIG. 9A), her bone marrow displayed monotonous cellularity, from the preponderance of blast cells. The inset shows the appearance of the blast cells on the aspirate. After 2 weeks of therapy (FIG. 9B), the core biopsy showed ongoing hypercellularity, but clear evidence of maturation, as determined by the cells that have varied sizes and shapes, approximating the "field of flowers" appearance of a normal marrow. In the inset the aspirate no longer shows blast cells, but instead mostly myelocytes, which is evidence of differentiation. At this timepoint, given the reduction in blasts to <5% and preservation of neutrophils and platelets, this patient met the criteria for a full CR. This was maintained at D28, which again showed hypercellularity, but with maturation and no increase in blast cells (FIG. 9C).

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

I claim:

1. A pharmaceutical composition for oral administration comprising (a) a solid dispersion comprising between 25-75% w/w of (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide (Compound 1) or a pharmaceutically acceptable salt thereof, and a polymer selected from hydroxypropylmethylcellulose acetate succinate (HPMCAS), polyvinyl acetate phthalate (PVAP), hydroxypropylmethylcellulose (HPMC) and hydroxypropylmethylcellulose phthalate (HPMCP) and optionally (b) one or more pharmaceutically acceptable carrier(s).

2. The pharmaceutical composition of claim 1 wherein the polymer is HPMCAS.

3. The pharmaceutical composition of claim 2 wherein the solid dispersion is a spray-dried dispersion.

4. The pharmaceutical composition of claim 3 wherein the solid dispersion comprises between about 30 and 70% w/w Compound 1.

5. The pharmaceutical composition of claim 4 wherein the solid dispersion comprises between about 40 and 60% compound 1.

6. The pharmaceutical composition of claim 4 wherein the solid dispersion comprises about 50% w/w Compound 1.

7. The pharmaceutical composition of claim 3 wherein the solid dispersion comprises about 25% Compound 1.

8. The pharmaceutical composition of claim 3 wherein the dispersion is an amorphous dispersion.

9. The pharmaceutical composition of claim 3 wherein the dispersion further comprises a surfactant or inert pharmaceutically acceptable substance.

10. The pharmaceutical composition of claim 9 wherein the surfactant is vitamin E or sodium lauryl sulfate (SLS).

11. The pharmaceutical composition of claim 3 wherein the composition further comprises a filler.

12. The pharmaceutical composition of claim 11 wherein the filler is microcrystalline cellulose.

13. The pharmaceutical composition of claim 3 wherein the composition further comprises a disintegrant.

14. The pharmaceutical composition of claim 13 wherein the disintegrant is croscarmellose sodium.

15. The pharmaceutical composition of claim 3 wherein the composition further comprises a wetting agent.

16. The pharmaceutical composition of claim 15 wherein the wetting agent is sodium lauryl sulfate.

17. The pharmaceutical composition of claim 3 wherein the composition further comprises a glidant.

18. The pharmaceutical composition of claim 17 wherein the glidant is colloidal silicon dioxide.

19. The pharmaceutical composition of claim 3 wherein the composition further comprises a lubricant.

20. The pharmaceutical composition of claim 19 wherein the lubricant is magnesium stearate.

21. The pharmaceutical composition of claim 3 wherein the pharmaceutical composition comprises from between about 25% w/w to about 35% w/w of Compound 1, or a pharmaceutically acceptable salt thereof, from between about 25% w/w to about 35% w/w of hydroxypropylmethylcellulose acetate succinate (HPMCAS), from between about 25% w/w to about 35% w/w of microcrystalline cellulose, from between about 5% w/w to about 7% w/w croscarmellose sodium, from between about 0.5% w/w to about 1.5% w/w sodium lauryl sulfate, about from between about 1% w/w to about 3% w/w colloidal silicon dioxide, and rom between about 0.5% w/w to about 2.5% w/w of magnesium stearate, thereby totaling 100% by weight of the composition.

22. The pharmaceutical composition of claim 3 wherein the pharmaceutical composition comprises, about 30% w/w of compound 1, or a pharmaceutically acceptable salt thereof, about 30% w/w of hydroxypropylmethylcellulose acetate succinate (HPMCAS), about 29.5% w/w of microcrystalline cellulose, about 6% w/w croscarmellose sodium, about 1% w/w sodium lauryl sulfate, about 2% w/w colloidal silicon dioxide, and about 1.5% w/w of magnesium stearate.

23. The pharmaceutical composition of claim 22 wherein the pharmaceutical composition is a tablet.

* * * * *

UNITED STATES PATENT AND TRADEMARK OFFICE
CERTIFICATE OF CORRECTION

PATENT NO. : 10,449,184 B2  
APPLICATION NO. : 15/949750  
DATED : October 22, 2019  
INVENTOR(S) : Chong-Hui Gu Page 1 of 1

It is certified that error appears in the above-identified patent and that said Letters Patent is hereby corrected as shown below:

In the Claims

Column 50, Claim 4, Lines 46-47: delete "30 and 70% w/w Compound 1" and replace with -- 30 and 70% w/w of Compound 1 --.

Column 50, Claim 5, Lines 49-50: delete "60% compound 1" and replace with -- 60% w/w of Compound 1 --.

Column 50, Claim 6, Line 52: delete "50% w/w Compound 1" and replace with -- 50% w/w of Compound 1 --.

Column 50, Claim 7, Line 54: delete "25% Compound 1" and replace with -- 25% w/w of Compound 1 --.

Column 52, Claim 21, Line 6: delete "and rom between" and replace with -- and from between --.

Column 52, Claim 22, Lines 10-11: delete "30% w/w of compound 1," and replace with -- 30% w/w of Compound 1, --.

Signed and Sealed this  
Third Day of December, 2019

Andrei Iancu  
*Director of the United States Patent and Trademark Office*